United States Patent
Zon et al.

(10) Patent No.: US 9,771,560 B2
(45) Date of Patent: Sep. 26, 2017

(54) HIGH-THROUGHPUT IMAGE-BASED CHEMICAL SCREENING IN ZEBRAFISH BLASTOMERE CELL CULTURE

(71) Applicants: CHILDREN'S MEDICAL CENTER CORPORATION, Boston, MA (US); PRESIDENT AND FELLOWS OF HARVARD COLLEGE, Cambridge, MA (US); JOSLIN DIABETES CENTER INC., Boston, MA (US)

(72) Inventors: Leonard I. Zon, Wellesley, MA (US); Cong Xu, Boston, MA (US); Amy J. Wagers, Cambridge, MA (US); C. Ronald Kahn, Newton, MA (US)

(73) Assignees: CHILDREN'S MEDICAL CENTER CORPORATION, Boston, MA (US); PRESIDENT AND FELLOWS OF HARVARD COLLEGE, Cambridge, MA (US); JOSLIN DIABETES CENTER INC., Boston, MA (US)

( * ) Notice: Subject to any disclaimer, the term of this patent is extended or adjusted under 35 U.S.C. 154(b) by 28 days.

(21) Appl. No.: 14/384,514

(22) PCT Filed: Mar. 14, 2013

(86) PCT No.: PCT/US2013/031504
§ 371 (c)(1),
(2) Date: Sep. 11, 2014

(87) PCT Pub. No.: WO2013/138623
PCT Pub. Date: Sep. 19, 2013

(65) Prior Publication Data
US 2015/0147807 A1 May 28, 2015

Related U.S. Application Data

(60) Provisional application No. 61/610,668, filed on Mar. 14, 2012, provisional application No. 61/720,713, filed on Oct. 31, 2012.

(51) Int. Cl.
| | | |
|---|---|---|
| *C12N 5/00* | (2006.01) | |
| *C12N 5/02* | (2006.01) | |
| *C12N 5/077* | (2010.01) | |
| *G01N 33/50* | (2006.01) | |
| *G01N 33/569* | (2006.01) | |
| *A61K 38/18* | (2006.01) | |
| *A61K 38/28* | (2006.01) | |
| *A61K 38/30* | (2006.01) | |
| *A61K 35/545* | (2015.01) | |

(52) U.S. Cl.
CPC .......... *C12N 5/0658* (2013.01); *A61K 35/545* (2013.01); *A61K 38/1808* (2013.01); *A61K 38/1825* (2013.01); *A61K 38/1841* (2013.01); *A61K 38/1858* (2013.01); *A61K 38/28* (2013.01); *A61K 38/30* (2013.01); *G01N 33/5044* (2013.01); *G01N 33/56983* (2013.01); *C12N 2501/01* (2013.01); *C12N 2501/115* (2013.01); *C12N 2501/16* (2013.01); *C12N 2501/999* (2013.01); *C12N 2506/02* (2013.01); *C12N 2506/45* (2013.01)

(58) Field of Classification Search
CPC .. C12N 5/068; C12N 2506/00; C12N 5/0606; C12N 5/0658
See application file for complete search history.

(56) References Cited

U.S. PATENT DOCUMENTS

2004/0247571 A1   12/2004   Meijer et al.

FOREIGN PATENT DOCUMENTS

| WO | 2008060792 A2 | 5/2008 |
| WO | 2009117439 A2 | 9/2009 |

OTHER PUBLICATIONS

Seamon, 1981, PNAS, 78:3363-3367.*
Wu, 2009, Trends in Biochemical Sciences 35:161-168.*
Wagers, 2002, 297:2256-2259.*
Liu, J Cell Biochem, 2003, 88:29-40.*
Ferrari, Science,1998, 279:1528-1530.*
Ornitz (2001, Genome Biology. 2:reviews3005.1-12).*
Mizuno et al. "Generation of skeletal muscle stem/progenitor cells from murine induced pluripotent stem cells." The FASEB Journal, Feb. 24, 2010, vol. 24, No. 7, pp. 2245-2253.
Zheng et al. "Skeletal myogenesis by human embryonic stem cells." Cell Research, Aug. 2006, vol. 16, No. 8, pp. 713-722.
Darabi et al. "Functional skeletal muscle regeneration from differentiating embryonic stem cells." Nature Medicine, Jan. 20, 2008, vol. 14, No. 2, pp. 134-143.
Barberi et al., "Derivation of engraftable skeletal myoblasts from human embryonic stem cells", Nat. Med. 13(5):642-648 (2007).
Cerletti et al., "Highly Efficient, Functional Engraftment of Skeletal Muscle Stem Cells in Dystrophic Muscles", Cell 134(1):37-47 (2008).
Darabi et al., "Functional skeletal muscle regeneration from differentiating embryonic stem cells", Nat. Med. 14(2):134-143 (2008).
Huang et al., "High-Throughput Screening for Bioactive Molecules Using Primary Cell Culture of Transgenic Zebrafish Embryos", Cell Rep. 2(3):695-704 (2012).
Lagord et al., "Stimulation of Rat Satellite Cell Myogenesis by Inhibitors of ser/thr Protein Kinases", Neuromus. Disord. 3(5/6):379-383 (1993).
Mizuno et al., "Generation of skeletal muscle stem/progenitor cells from murine induced pluripotent stem cells", FASEB J. 24(7):2245-2253 (2010).

(Continued)

Primary Examiner — Valarie Bertoglio
(74) Attorney, Agent, or Firm — Nixon Peabody LLP; David S. Resnick

(57) ABSTRACT

Disclosed are methods of inducing differentiation of stem into myogenic cells without gene manipulation and for inducing proliferation of satellite cells. The cells can be used as a source of cells for transplantation in a subject in need thereof. Also disclosed is a screening assay for screening test compounds using blastomere cultures.

3 Claims, 13 Drawing Sheets

(56) References Cited

OTHER PUBLICATIONS

Tseng et al., "The GSK-3 Inhibitor BIO Promotes Proliferation in Mammalian Cardiomyocytes", Chem. Biol. 13(9):957-963 (2006).
Wozniak et al., "Signaling Satellite-Cell Activation in Skeletal Muscle: Markers, Models, Stretch, and Potential Alternate Pathways", Muscle Nerve 31(3)283-300 (2005).
Xu et al., "A Zebrafish Embryo Culture System Defines Factors that Promote Vertebrate Myogenesis Across Species", Cell 155(4):909-921 (2013).
Yu et al., "Dorsomorphin inhibits BMP signals required for embryogenesis and iron metabolism", Nat. Chem. Biol. 4(1):33-41 (2008).
Zheng et al., "Skeletal myogenesis by human embryonic stem cells", Cell Res. 16(8):713-722 (2006).
Van Der Velden et al., "Inhibition of glycogen synthase kinase-3β activity is sufficient to stimulate myogenic differentiation", American Journal of Physiology-Cell Physiology 290:C453-C462 (2006).
Van Der Velden et al., "Glycogen Synthase Kinase 3β Suppresses Myogenic Differentiation through Negative Regulation of NFATc3", Journal of Biological Chemistry 283(1):358-366 (2008).

\* cited by examiner

A

B

C

HIGH-THROUGHPUT IMAGE-BASED CHEMICAL SCREENING IN ZEBRAFISH BLASTOMERE CELL CULTURE

CROSS REFERENCE TO RELATED APPLICATIONS

This application is a 35 U.S.C. §371 National Phase Entry Application of International Application No. PCT/US2013/031504 filed Mar. 14, 2013, which designates the U.S., and which claims benefit under 35 U.S.C. §119(e) of the U.S. Provisional Application No. 61/610,668, filed Mar. 14, 2012 and the U.S. Provisional Application No. 61/720,713, filed Oct. 31, 2012, content of both of which is incorporated herein by reference in their entirety.

GOVERNMENT SUPPORT

This invention was made with government support under grant nos. 5P30 DK49216-19, 5R01CA103846-10, DP2OD004345 and DK31036 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 15, 2014, is named 701039-073623-US_SL.txt and is 10,204 bytes in size.

TECHNICAL FIELD

The disclosure relates generally to compositions and methods for inducing differentiation of stem cells into myogenic cells and uses thereof. More specifically, the disclosure is concerned with compositions and methods of inducing differentiation of induced pluripotent stem cells (iPSCs and embryonic stem cells (ESCs) into myogenic cells. The present disclosure also provides methods for inducing proliferation of satellite cells and uses thereof. The present disclosure also provides screening assays for assaying modulators of organ development.

BACKGROUND

Skeletal muscle is a highly specialized tissue composed of non-dividing, multinucleated muscle fibers that contract to generate force in a controlled and directed manner. Skeletal muscle is formed during embryogenesis from a subset of muscle precursor cells found in a region of the embryo known as the myotome. In addition to generating differentiated muscle fibers, these cells also give rise to specialized muscle-forming stem cells, known as satellite cells, which remain associated with muscle fibers and are responsible for muscle growth and repair throughout life (Gros et al., 2006; Seale et al., 2000). Injury-induced satellite cell proliferation both replenishes the satellite cell pool and produces differentiated myoblasts which fuse with existing myofibers and with one another to regenerate muscle tissue.

Satellite cells are defined anatomically by their localization beneath the basal lamina of muscle fibers (Mauro, 1961) and molecularly by their expression of the paired-box transcription factor Pax7 (Seale et al., 2000). In resting muscle, satellite cells are maintained in a largely dormant state, but in response to muscle damage, these cells become activated, an event marked by their upregulation of MyoD, and enter the cell cycle (Seale et al., 2000). Transplantation-based studies in animal models have demonstrated the utility of engrafted satellite cells for regenerating diseased muscle (Cerletti et al., 2008; Sherwood et al., 2004) and analyses of mouse and human muscles indicate that their loss during aging contributes to age-associated muscle weakness (Cerletti et al., 2012). Thus, muscle satellite cells are promising targets for cell therapies involving either cell replacement or activation of endogenous repair mechanisms. However, realization of this promise has been hindered by the paucity of satellite cells that can be isolated from adult skeletal muscle and a lack of methods to support their ex vivo expansion.

In contrast to satellite cells, embryonic stem cells (ESCs) and, more recently, iPSCs process boundless expansion potential in culture and are theoretically capable of generating an unlimited supply of differentiated cell types, including myogenic cells. Although some success has been achieved in directing the myogenic differentiation of ESCs/IPSCs, largely through genetic manipulation and cell sorting approaches (Barberi et al., 2007; Darabi et al., 2008; Mizuno et al., 2010; Zheng et al., 2006), the generation of well differentiated muscle cells from human or murine pluripotent cells has proved very challenging. Thus, to realize the promise of stem cell approaches or muscle biology and regeneration, it is essential to uncover the molecular pathways that regulate the myogenic specification of these cells, and to develop systems that enable their robust and selective differentiation in ex vivo systems.

SUMMARY

The present disclosure relates to the differentiation of stem cells including embryonic stem cells and induced pluripotent stem cells. More specifically, the present disclosure is concerned with methods of inducing differentiation of stem cells into myogenic cells.

In one aspect, there is provided a method of inducing differentiation of stem cells in myogenic cells comprising, culturing the cells in a medium comprising at least two of: (i) a GSK3 pathway inhibitor; (ii) a compound that increases intracellular levels of 3',5'-cyclic adenosine monophosphate (cAMP); and (iii) a FGF pathway activator.

Also provided is a method of converting stem cells into multipotent stem cells capable of giving rise to myogenic cells, the method comprising culturing the stem cells in the presence of at least two of: (i) a GSK3 pathway inhibitor; (ii) a compound that increases intracellular levels cAMP; and (iii) a FGF pathway activator.

In another aspect, the present invention provides a method of conditioning stem cells for further differentiation into myogenic cells comprising culturing the cells in the presence of at least two of: (i) a GSK3 pathway inhibitor; (ii) a compound that increases intracellular levels of cAMP; and (iii) a FGF pathway activator.

In one embodiment, the myogenic cells are cells of the skeletal myogenic lineage.

In one embodiment, the myogenic cells are terminally differentiated skeletal muscle cells.

In a further aspect, the disclosure provides a myogenic cell prepared in accordance with the method disclosed herein. In an embodiment, the myogenic cell is for implantation into a subject for increasing muscle mass or preventing or treating a muscle disease, the stem cell having been subjected to a differentiation treatment according to the method disclosed herein prior to implantation to convert (i.e., transform/differentiate) the stem cell into a myogenic cell. The present invention also concerns a method of transplanting myogenic cells in a subject comprising implanting in the subject myogenic cells prepared in accordance with the method disclosed herein.

In another aspect, the disclosure provides a method of increasing muscle mass or of preventing or treating a muscle disease in a subject comprising implanting into the subject myogenic cells prepared in accordance with the method disclosed herein.

In another aspect, the disclosure provides a use of the myogenic cells prepared according to the method disclosed herein, for transplantation into a subject.

In another aspect, the disclosure provides a use of the myogenic cells prepared according to the method disclosed herein, for increasing muscle mass or preventing or treating a muscle disease in a subject.

In one aspect, there is provided a method of increasing satellite cell proliferation, the method comprising: culturing a satellite cell in the presence of a compound that increases intracellular levels of 3′,5′-cyclic adenosine monophosphate.

In a further aspect, the disclosure provides a satellite cell prepared in accordance with the method disclosed herein. In an embodiment, the satellite cell is for implantation into a subject for increasing muscle mass or preventing or treating a muscle disease, the satellite cell having been subjected to a proliferation treatment according to the method disclosed herein prior to implantation to convert (i.e., transform/differentiate). The present invention also concerns a method of transplanting satellite cells in a subject comprising implanting in the subject satellite cells prepared in accordance with the method disclosed herein.

In another aspect, the disclosure provides a method of increasing muscle mass or of preventing or treating a muscle disease in a subject comprising implanting into the subject satellite cells prepared in accordance with the method disclosed herein.

In another aspect, the disclosure provides a use of the satellite cells prepared according to the method disclosed herein, for transplantation into a subject.

In another aspect, the disclosure provides a use of the satellite cells prepared according to the method disclosed herein, for increasing muscle mass or preventing or treating a muscle disease in a subject.

In another aspect, the disclosure provides a composition for inducing differentiation of stem cells to myogenic cells, the composition comprising at least two of: (i) a GSK3 pathway inhibitor; (ii) a compound that increases intracellular levels of cAMP; and (iii) a FGF pathway activator.

The disclosure also provides a method of treating subject for damaged muscle tissue or increasing muscle mass, the method comprising co-administering to the subject in need thereof at least two of: (i) a GSK3 pathway inhibitor; (ii) a compound that increases intracellular levels of cAMP; and (iii) a FGF pathway activator.

In one aspect provided herein is a method for screening chemical compounds or compositions in zebrafish blastomere cells comprising the steps of culturing a population of zebrafish blastomere cells in presence of a test compound, wherein the blastomere cell comprises a cell lineage specific marker (CLSM) fused with a fluorescent protein (i.e., a CSLM:FP construct); and visualizing the FP. A change in level or amount of FP indicating that the test compound modulates the development of organ that expresses the cell lineage specific marker. The level or expression of FP can be determined relative to a reference or control.

BRIEF DESCRIPTION OF THE DRAWINGS

FIGS. 1A-1E show the chemical genetic screen to identify modifiers of skeletal muscle development. FIG. 1A shows that myf5-GFP; mylz2-mCherry double transgenic expression recapitulates endogenous expression of the genes respectively. myf5-GFP is first detected at the 11-somite stage in the newly formed somite. The yolk of the double transgenic embryo is mCherry positive, presumptively due to the maternal deposit of mCherry protein. mylz2-mCherry expression is not observed until 32 hpf. Its expression is first detected in anterior somites and then progressively spreads to posterior somites. FIG. 1B shows myf5-GFP; mylz2-mCherry embryos were disassociated at the oblong stage and cultured in zESC medium with or without bFGF. Images were taken 48 hours after plating. Scale bars represent 250 μM. FIG. 1C shows the expression of myogenic genes measured by quantitative RT-PCR. Blastomere cells from myf5-GFP; mylz2-mCherry embryos were cultured with or without bFGF and harvested at 24 hours. Results of bFGF treated cells are normalized to the expression of untreated cells. Error bars represent standard deviation (SD) from the triplicate quantitative RT-PCR reaction. All expressions are normalized to β-actin. FIG. 1D shows the expression of myogenic genes measured by quantitative RT-PCR. Blastomere cells from myf5-GFP; mylz2-mCherry embryos were cultured with bFGF and harvested at 24 hours. Different populations were isolated by FACS. Results are normalized to the expression of cells of the double negative population. Error bars represent standard deviation (SD) from the triplicate quantitative RT-PCR reaction. All expressions are normalized to β-actin. FIG. 1E shows that ATRA blocks muscle development in vitro. myf5-GFP; mylz2-mCherry embryos were disassociated at the oblong stage and cultured in zESC medium with bFGF. 0.1% DMSO or 100 nM ATRA was added immediately. Images were taken 48 hours after plating. Scale bars represent 250 μM.

FIG. 2A is a schematic of a high-throughput image-based chemical screening assay. Approximately 800 myf5-GFP; mylz2-mCherry double transgenic embryos were collected and disassociated at the oblong stage. The resulting blastomere cells were aliquoted into four 384-well plates with pre-added chemicals. We performed duplicates for each chemical to mitigate false positives. After 2 days, the 384-well plates were imaged using a Celigo cytometer. For each well, an image for each signal channel was captured. GFP and mCherry signals were determined by the Celigo cytometer's built-in software and confirmed by eye. FIG. 2B shows sample images from the modifier screening. Most of the hits could be grouped into three categories. Category I has only myf5-GFP expression, examples being TCPOBOP and CA-074-Me. The phenotype is presumptively due to inhibition of differentiation of muscle progenitors into mature muscle. Category II has a decreased amount of both fluorescent colors, examples being Ro 41-1049 and tyrphostin AG 879. This phenotype is presumptively due to the blocking of muscle progenitor commitment. Category III has an increased expression of both markers presumably due to accelerated muscle development. Scale bars represent 250 μM. FIG. 2C shows hits from a screen without supplementing bFGF to the culture medium. 6 chemicals were identified to increase the GFP and mCherry signals. Scale bars represent 250 μM.

FIG. 3A, satellite cells from C57BL/6J mice were cultured and treated with DMSO or forskolin in the absence or presence of basic fibroblast growth factor (bFGF). Total number of cells were counted after 5 days and are shown as fold changes compared to the DMSO treated cells in the absence of bFGF (mean+/−SEM, n=4). Forskolin expands satellite cells by ~2 or ~2.3 folds compared to the DMSO treated cells in the absence or presence of bFGF, respectively. FIG. 3B shows fold change of number of satellite cells from mdx mice after 5 days in culture and forskolin treatment as compared to the DMSO treated satellite cells. Forskolin expands mdx satellite cells by ~3.6 folds in culture (mean+/−SEM, n=4). FIG. 3C shows that concentration of cAMP in cultured satellite cells is increased by ~4.5, ~5.2 or ~5.7 fold after treatment with 25 µM, 50 µM or 100 µM of forskolin, respectively as compared to the DMSO treated cells. (mean+/−SD, n=5). FIG. 3D, satellite cells were isolated from C57BL/6J mice and a single cell was plated into each well of 96-well plates. Cells were cultured for 6 days and treated with DMSO or forskolin. Number of wells containing a myogenic colony and number of cells in each colony were counted after 6 days. FIG. 3E shows that in vitro clonal plating efficiency of satellite cells is not affected by forskolin treatment as compared to DMSO-treated cells (mean+/−SD, n=4). FIG. 3F shows that forskolin treatment increases the number of myogenic cells originated from a single satellite cell in each well, showing an increase in cell proliferation. ★: P<0.05, ★★: P<0.01 (mean+/−SD, n=4).

FIG. 4A, satellite cells from C57BL/6J mice were cultured in the presence of bFGF for 5 days. In order to test the effect of forskolin on in vitro differentiation of satellite cells, the cells were harvested on day 5 and equal numbers of cells were induced to differentiation in the presence of forskolin or DMSO. FIG. 4B shows pictures of satellite cells differentiated in the presence of DMSO (left) or forskolin (right) and stained for Myosin Heavy Chain (MHC, red) and nuclei (blue). Scale bar: 200 µm. FIG. 4C shows quantification of percentage of nuclei in myotubes after differentiation of satellite cells in the presence of forskolin or DMSO (mean+/−SEM, n=4). Differentiation potential of satellite cells is not affected by presence of forskolin in the medium as compared to DMSO. FIG. 4D, satellite cells from C57BL/6J mice were cultured in the presence of bFGF and forskolin/DMSO treatment for 5 days. In order to test differentiation potential of forskolin treated satellite cells, the cells were harvested on day 5 and equal numbers of cells were induced to differentiation in the absence of the compound. FIG. 4E shows pictures of DMSO (left) or forskolin (right) treated satellite cells differentiated in the absence of compound and stained for MHC (red) and nuclei (blue). Scale bar: 200 µm. FIG. 4F shows the quantification of percentage of nuclei in myotubes after differentiation of forskolin or DMSO treated cells (mean+/−SEM, n=5). Forskolin-treated satellite cells don't show any defect in in vitro myotube formation as compared to DMSO treated cells.

FIG. 5A shows representative FACS plots depicting CD45⁻ SCA-1⁻MAC1⁻ cells and show gating of CXCR4⁺ and β-1 Integrin⁺ cells for freshly isolated (left panel) and cultured satellite cells treated with DMSO (middle panel) or forskolin (right panel). FIG. 5B shows the average frequency (mean+/−SEM, n=6) of CXCR4⁺β-1 Integrin⁺ cells among cultured satellite cells treated with DMSO or forskolin was quantified by FACS. Results indicate that cultured satellite cells treated with either DMSO or forskolin retain expression of cell surface markers CXCR4 and β-1 Integrin by ~80%. FIG. 5C, GFP⁺ satellite cells were harvested from β-actin GFP mice and were transplanted into TA muscle of recipient mdx mice, injured 1 day previously by injection of cardiotoxin, either right after isolation or after five days in culture with DMSO or forskolin treatment. FIG. 5D shows the quantification of donor derived myofibers in mdx muscle transplanted with freshly isolated, cultured DMSO-treated or cultured forskolin-treated satellite cells (n=6). FIG. 5E shows transverse frozen section of TA muscle from mdx mice transplanted with 6000 freshly isolated satellite cells (left panel), cultured DMSO-treated satellite cells expanded from 6000 freshly isolated cells (middle panel) or cultured forskolin-treated satellite cells expanded from 6000 freshly isolated cells (right panel). Scale bars represent 200 µm.

FIGS. 6A and 6B show the gene expression analysis of EBs (FIG. 6A) and monolayer cells (FIG. 6B). Cells were harvested at the times indicated for RNA extraction. Ectodermal, endodermal and mesodermal genes were analyzed by quantitative RT-PCR using GAPDH as a housekeeping gene. Changes in gene expression levels are expressed relative to undifferentiated iPSCs (Day 0). Bars represent the standard deviation of three independent experiments (*p<0.05, <0.01, *<0.001). FIG. 6C shows the immunostaining of differentiated iPSCs. Under terminal differentiating procedures (day 36) most of the cells express Desmin (red) and Myogenin (green), forming multinucleated myofibers. Cells were also stained with Hoechst (blue). The number on each panel represents the percentage of cells expressing Desmin and Myogenin. Scale bars represent 100 µM. FIG. 6D shows representative electron microscopy image of differentiated BJ cells at day 36, magnification ×52700. FIG. 6E shows immuno-electron microscopy staining using skeletal muscle specific anti-myosin heavy and light chain. Black dots indicate gold cross-linked particles to secondary antibody, magnification ×52700.

FIG. 8A shows the higher magnification of myf5-GFP; mylz2-mCherry blastomere cells cultured in the zESC medium with bFGF. FIG. 8B shows myf5-GFP; mylz2-mCherry embryos injected with 400 pg con-MO or co-injected with 200 pg myf5-MO and 200 pg myoD-MO lack both myf5-GFP and mylz2-mCherry expression. Images were taken at 30 hpf. FIG. 8C shows myf5-GFP; mylz2-mCherry embryos injected with 400 pg con-MO or co-injected with 200 pg myf5-MO and 200 pg myoD-MO were disassociated at the oblong stage and cultured in zESC medium with bFGF. No myf5-GFP or mylz2-mCherry expression was detected in the culture of double morphants. Images were taken 26 hours after plating.

FIG. 9B, myf5-GFP; mylz2-mCherry embryos were collected at the oblong stage and disassociated. The resulting blastomere cells were aliquoted into a 96-well plate with pre-added chemicals. The culture medium contained 10 ng/ml bFGF to promote muscle development. Cells were treated with 50 µM tyrphostin AG 879, 50 µM tyrphostin AG 808, 50 µM tyrphostin AG 555, 50 µM PD 98059, 10 µM U0126, 10 µM LY-294002, 10 µM wortmannin, or 20 µM rapamycin. Cells were imaged after 2 days by the Celigo cytometer for GFP, mCherry, and bright-field signals. FIG. 9C, 1-cell-stage myf5-GFP; mylz2-mCherry embryos were injected with 250 pg fgf8-MO and 250 pg fgf24-MO and rescued by adding 10 forskolin at the dome stage.

FIG. 10A, satellite cells from C57BL/6J (wild type) or mdx mice were cultured and treated with DMSO or forskolin in the presence of bFGF. Cell numbers were counted at day 5 and are shown as fold change of wild type cells treated with DMSO. mdx satellite cells show defect in ex vivo expansion and forskolin treatment restores the number of cultured satellite cells (mean+/−SEM, n=4). FIG. 10B, shows transverse frozen section of mdx muscle transplanted with cultured forskolin-treated GFP$^+$ satellite cells showing GFP (left, green) and Dystrophin (right, red) in the engrafted fibers.

FIG. 11A shows the expression of nuclear NANOG, OCT4 and cytoplasmic SSEA3, SSEA4, TRA1-60 in undifferentiated 00409 and 05400 iPSCs. Images show merged colors between blue (Hoechst) and red (indicated protein). FIG. 11B shows bright-field images of BJ, 00409, 05400 iPSC colonies. FIG. 11C shows the gene expression analysis of undifferentiated 00409 and 05400 iPSCs. Indicated pluripotency genes were analyzed by quantitative RT-PCR using GAPDH as a housekeeping gene. Changes in gene expression levels are expressed relative to undifferentiated BJ iPSCs. Bars represent the standard deviation of three independent experiments. FIG. 11D shows the bright-field images showing EB formation of BJ, 00409 and 05400 iPSCs after 7 days of differentiation. Scale bars represent 100 µM.

FIGS. 12A and 12B show the gene expression analysis of EB (FIG. 12A) and monolayer cells (FIG. 12B). Cells were harvested at the times indicated for RNA extraction. Ectodermal, endodermal and mesodermal genes were analyzed by quantitative RT-PCR using GAPDH as housekeeping gene. Changes in gene expression levels are expressed relative to undifferentiated iPSCs (Day 0). Bars represent the standard deviation of three independent experiments, (*$p<0.05$, $<0.01$, *$<0.001$). FIG. 12C shows immunostaining of differentiated 05400 iPSCs. Under terminal differentiating procedures (day 36) most of the cells express Desmin (red) and Myogenin (green), forming multinucleated myofibers. Cells were also stained with Hoechst (blue). FIG. 12D shows representative electron microscopy images of differentiated 00409 and 05400 cells at day 36, magnification ×52700. FIG. 12E shows immuno-electron microscopy staining using skeletal muscle specific anti-Myosin heavy and light chain. Black dots indicate gold cross-linked particles to secondary antibody, magnification ×52700.

FIGS. 13A and 13B, BJ iPSC-derived EBs were stimulated with bFGF+BIO (FIG. 13A) and bFGF+forskolin (FIG. 13B). Cells were harvested at the times indicated for RNA extraction. Ectodermal, endodermal and mesodermal genes were analyzed by quantitative RT-PCR using GAPDH as a housekeeping gene. Changes in gene expression levels are expressed relative to undifferentiated BJ iPSCs (Day 0).

DETAILED DESCRIPTION

Figure 1:
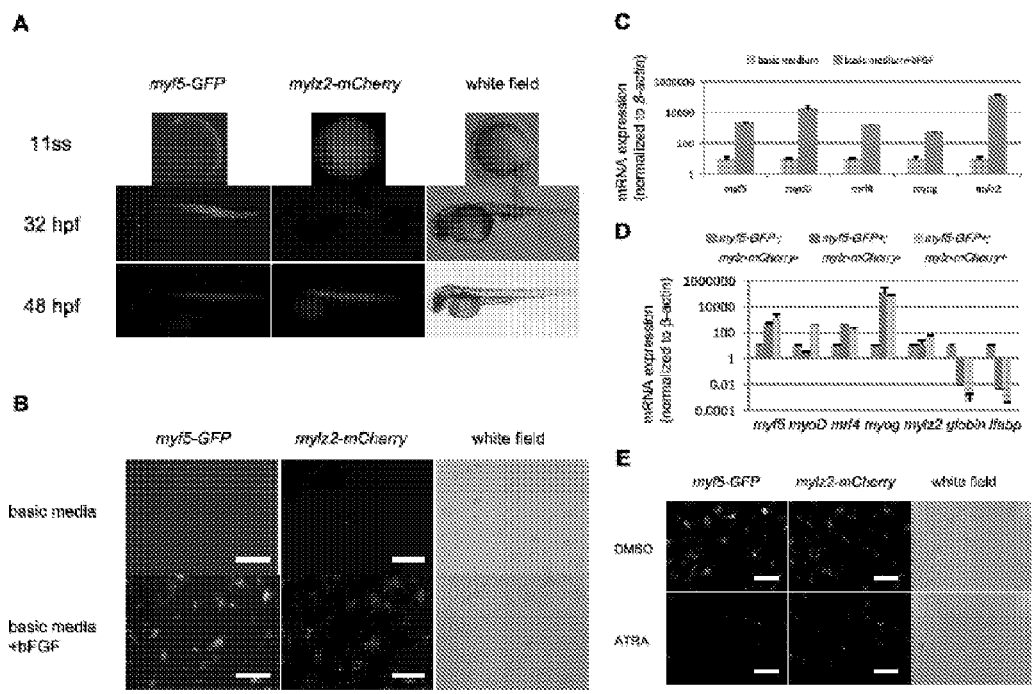

The present disclosure is based, in part, on the inventors' surprising and unexpected discovery that stem cells can be induced to differentiate into skeletal muscle cells without gene manipulation. Accordingly, in one aspect provided herein is a method for inducing differentiation of a stem cell into a myogenic cell. Generally, the method comprises contacting a stem cell with at least two of: (i) a GSK3 pathway inhibitor; (ii) a compound that increases intracellular levels of 3',5'-cyclic adenosine monophosphate (cAMP); and (iii) a FGF pathway activator. Without limitations, the stem cell to be contacted can be in vitro, ex vivo or in vivo.

In some embodiments, the contacting is with the FGF pathway activator and the GSK3 pathway inhibitor. In embodiments, the contacting is with the FGF pathway activator and the compound that increases intracellular levels of cAMP. In some embodiments, contacting is with the GSK3 pathway inhibitor and the compound that increases intracellular levels of cAMP.

In some embodiments, the method comprises contacting the stem cell with all three, i.e., contacting with a GSK3 pathway inhibitor, a compound that increases intracellular levels of 3',5'-cyclic adenosine monophosphate (cAMP), and a FGF pathway activator.

The stem cell can be contacted with the combination of the compounds that induce differentiation to a myogenic cell in a cell culture e.g., in vitro or ex vivo, or the compounds can be co-administrated to a subject, e.g., in vivo. In some embodiments, the combination of compounds that induces differentiation of the stem cell into a myogenic cell can be administrated to a subject for repairing or regenerating a damaged muscle tissue.

As used herein, the term "stem cells" refers to cells capable of differentiating into many cell types of an organism from which it arises and includes totipotent, pluripotent and multipotent cells (e.g., stem cells of embryonic origin (e.g., ESCs), induced stem cells (iPSCs) and multipotent progenitor cells).

In some embodiments, the stem cell expresses at least one of Rex-1, OCT4, SOX2, and Nanog. In some embodiments, the stem cell expresses CD73. In some embodiments, the stem cell expresses CD73 and at least one of Rex-1, OCT4, SOX2, and Nanog.

As used herein, the term "myogenic cells" refers to cells giving rise to or forming muscle tissue and includes cells expressing one or more of the following markers Pax3, Pax7, MyoD, Myf5, myogenin, GATA2, and MHC and low levels of embryogenic markers such as Rex-1. In some embodiments, the myogenic cells disclosed herein are capable of fusing and forming myotubes comprising at least 10 (e.g., 10, 15, 20, 25, or more) nuclei. In some embodiments, the myogenic cells disclosed herein are capable of fusing and forming myotubes comprising from 5 to 20 nuclei.

In some embodiments, the myogenic cells are cells of the skeletal myogenic lineage.

In some embodiments, the myogenic cell prepared in accordance with the method disclosed herein express at least one, at least two, at least three, at least 4, at least 5 and preferably all of the following myogenic markers: Pax3, Pax7, MyoD, Myf5, myogenin, GATA2, CD56, desmin and MHC. In some embodiments, the myogenic cell prepared in accordance with the method disclosed herein express at least Myogenin, MyoD and MHC. In some embodiments, the myogenic cells prepared in accordance with the method disclosed herein express at least MyoD1 and Myf5.

In some embodiments, the myogenic cells prepared in accordance with the method disclosed herein express at least MyoD1, Myf5, and Pax7.

In some embodiments, the myogenic cells prepared in accordance with the method disclosed herein express at least MyoD1, Myf5, Pax7, and GATA2.

In one embodiment, the myogenic cells disclosed herein express lower levels of Rex-1, OCT4, SOX2 and/or Nanog than stem cells which have not been treated in accordance with the method disclosed herein.

In some embodiments, the stem cell is a pluripotent cell. The term "pluripotent" as used herein refers to a cell with the capacity, under different conditions, to differentiate to cell types characteristic of all three germ cell layers (endoderm, mesoderm and ectoderm). Pluripotent cells are characterized primarily by their ability to differentiate to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. In some embodiments, a pluripotent cell is an undifferentiated cell.

Stem cells that can be used in accordance with the method disclosed herein include embryonic stem cells, pluripotent stem cells and multipotent progenitor cells. In some embodiments, the stem cells are mammalian stem cells. In one embodiment, the stem cells are human stem cells.

In some embodiments, the stem cell is an induced pluripotent stem cell. As used herein, the term "induced pluripotent stem cell" or "iPSC" or "iPS cell" refers to a cell derived from a complete reversion or reprogramming of the differentiation state of a differentiated cell (e.g. a somatic cell). As used herein, an iPSC is fully reprogrammed and is a cell which has undergone complete epigenetic reprogramming. As used herein, an iPSC is a cell which cannot be further reprogrammed (e.g., an iPSC cell is terminally reprogrammed). Human pluripotent cell lines exhibit a level of developmental plasticity that is similar to the early embryo, enabling in vitro differentiation into all three embryonic germ layers. At the same time it is possible to maintain these pluripotent cell lines for many passages in the undifferentiated. These unique characteristics render human embryonic stem (ES) and human induced pluripotent stem (iPS) cells a promising tool for biomedical research. ES cell lines have already been established as a model system for dissecting the cellular basis of monogenic human diseases. The discovery of defined reprogramming methods (Takahashi and Yamanaka, Cell, 2006, 126: 663-676) and their use in the derivation of patient-specific iPS cell lines (Dimos et al., Science, 2008, 321: 1218-1221; and Park et al., Cell, 2008, 1,34: 877-886) has further expanded the utility of pluripotent cells for monogenic disease modeling.

In one embodiment, the stem cells are iPSCs derived from a subject in need of treatment for muscle repair or damage.

In some embodiments, the stem cell is an embryonic stem cell. As used herein, the term "embryonic stem cell" refers to the pluripotent stem cells of the inner cell mass of the embryonic blastocyst (see U.S. Pat. Nos. 5,843,780, 6,200, 806, which are incorporated herein by reference). Such cells can similarly be obtained from the inner cell mass of blastocysts derived from somatic cell nuclear transfer (see, for example, U.S. Pat. Nos. 5,945,577, 5,994,619, 6,235, 970, which are incorporated herein by reference). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

In one embodiment, the stem cells are ESs derived from a subject in need of treatment for muscle repair or damage.

In some embodiments, the stem cell is a multipotent stem cell. The term "multipotent" when used in reference to a "multipotent cell" refers to a cell that is able to differentiate into some but not all of the cells derived from all three germ layers. Thus, a multipotent cell is a partially differentiated cell. Multipotent cells are well known in the art, and examples of multipotent cells include adult stem cells, such as for example, hematopoietic stem cells and neural stem cells. Multipotent means a stem cell may form many types of cells in a given lineage, but not cells of other lineages. For example, a multipotent blood stem cell can form the many different types of blood cells (red, white, platelets, etc. . . . ), but it cannot form neurons.

In one embodiment, the stem cells are multipotent stem cells derived from a subject in need of treatment for muscle repair or damage.

In some embodiments, the stem cell is present in an embryoid body or an embryoid body-analogous cellular aggregate. Accordingly, in some embodiments, the method comprises forming an embryoid body from the stem cell before contacting with the compounds and activators.

The term "embryoid bodies" (EBs) is a term of art synonymous with "aggregate bodies". The terms refer to aggregates of differentiated and undifferentiated cells that appear when ES cells overgrow in monolayer cultures, or are maintained in suspension cultures. Embryoid bodies are a mixture of different cell types, typically from several germ layers, distinguishable by morphological criteria; see also infra. As used herein, "embryoid body", "EB" or "EB cells" typically refers to a morphological structure comprised of a population of cells, the majority of which are derived from embryonic stem (ES) cells that have undergone differentiation. Under culture conditions suitable for EB formation (e.g., the removal of Leukemia inhibitory factor or other, similar blocking factors), ES cells proliferate and form small mass of cells that begin to differentiate. In the first phase of differentiation, usually corresponding to about days 1-4 of differentiation for humans, the small mass of cells forms a layer of endodermal cells on the outer layer, and is considered a "simple embryoid body". In the second phase, usually corresponding to about days 3-20 post-differentiation for humans, "complex embryoid bodies" are formed, which are characterized by extensive differentiation of ectodermal and mesodermal cells and derivative tissues. As used herein, the term "embryoid body" or "EB" encompasses both simple and complex embryoid bodies unless otherwise required by context. The determination of when embryoid bodies have formed in a culture of pluripotent cells is routinely made by persons of skill in the art by, for example, visual inspection of the morphology. Floating masses of about 20 cells or more are considered to be embryoid bodies; see. e.g., Schmitt et al., Genes Dev. 5 (1991), 728-740; Doetschman et al., J. Embryol. Exp. Morph. 87 (1985), 27-45. It is also understood that the term "embryoid body", "EB", or "EB cells" as used herein encompasses a population of cells, the majority of which being pluripotent cells capable of developing into different cellular lineages when cultured under appropriate conditions. As used herein, the term also refers to equivalent structures derived from primordial germ cells, which are primitive cells extracted from embryonic gonadal regions; see, e.g., Shamblott, et al. (1998), supra. Primordial germ cells, sometimes also referred to in the art as EG cells or embryonic germ cells, when treated with appropriate factors form pluripotent ES cells from which embryoid bodies can be derived; see, e.g., U.S. Pat. No. 5,670,372.

Differentiation of the stem cells into myogenic cells can be confirmed by, for example, analyzing the expression of one or more myogenic cell markers. Markers characteristic of myogenic cells include the expression of cell surface proteins or the encoding genes, the expression of intracellular proteins or the encoding genes, cell morphological characteristics, and the like. Those skilled in the art will recognize that known immunofluorescent, immunochemical, polymerase chain reaction, in situ hybridization, Northern blot analysis, chemical or radiochemical or biological methods can readily ascertain the presence or absence of satellite cell specific characteristics.

If desired, the type(s) of cells in a population of cells can be determined using techniques that are well known in the art. For example, the use of cell-type specific stains. Alternatively, one can perform immunofluorescence staining using antibodies directed to various satellite cell specific proteins. In addition, a cell type can be determined by its morphology using techniques such as, for example, light microscopy, or electron microscopy. Exemplary myogenic cell markers include, but are not limited to, Pax3, Pax7, MyoD, Myf5, myogenin and MHC The term "contacting" or "contact" as used herein in connection with contacting a stem cell (or population of stem cells) includes subjecting the stem cells to an appropriate culture media which comprises the indicated compounds. Where the stem cell is in vivo, "contacting" or "contact" includes co-administering the compounds in the same or different pharmaceutical compositions to a subject via an appropriate administration route such that the compounds contacts the stem cell in vivo.

Cell culture media for differentiation induction include, but are not limited to, serum-free minimal essential medium (MEM), Dulbecco's modified Eagle medium (DMEM), RPMI1640 medium, 199 medium, F12 medium, mixtures thereof, and media prepared by supplementing any one of the aforementioned media with appropriate concentrations of publicly known medium additives in common use [e.g., serum albumin, 2-mercaptoethanol, insulin, transferrin, sodium selenite, ethanolamine, antibiotics (e.g., penicillin, streptomycin) and the like] [e.g., S-Clone medium (e.g., SF-03, Sanko Junyaku)] and the like.

The stem cell can be contacted with the combination of the compounds for any desired period of time. For example, for inducing differentiation, said contacting can be for hours, days or weeks. In some embodiments, said contacting can be for at least one day, e.g., one day, two days, three days, four days, five days, six days, a week, two weeks, three weeks, four weeks or more.

Myogenic cells prepared in accordance with the method disclosed herein can be used for transplantation. In some embodiments, the myogenic cells prepared in accordance with the method are autologous to the subject which will receive the transplantation. Myogenic cells prepared in accordance with the method disclosed herein can be used for transplantation in a subject for repairing or regenerating a damaged muscle tissue or increasing muscle mass of the subject.

The present disclosure also provides myogenic cells and populations prepared according to the method described herein. The cell population can be a purified population of myogenic cells. The myogenic cells can be obtained by sorting out the cell culture obtained by the method disclosed herein. In some embodiments, one or more kind of cells other than the myogenic cells can be co-present in the cell population. The present disclosure further provides a composition comprising a myogenic cell prepared according to the method described herein and a pharmaceutically acceptable carrier.

The present disclosure also provides a method for repairing or regenerating a damaged muscle tissue or increasing muscle mass of a subject. The method comprising co-administering to the subject therapeutically effective amount of at least two of: (i) a GSK3 pathway inhibitor; (ii) a compound that increases intracellular levels of 3',5'-cyclic adenosine monophosphate (cAMP); and (iii) a FGF pathway activator.

GSK3 Pathway

As used herein, an "inhibitor of the GSK3 pathway" refers to compounds and compositions that can inhibit the activity of at least one component of the GSK3 pathway. The definition and details of the GSK3 pathway are disclosed in the art e.g., Biondi R. M. and Nebreda A. R. Biochem J. 372, 1-13 (2003); Jope R. S. and Johnson G. V. Trends Biochem Sci. 29, 95-102 (2004); and Polakis P. Curr. Biol. 12, R499-R501 (2002), content of all of which is incorporated herein by reference in its entirety.

In some embodiments, the GSK3 pathway inhibitor is a GSK inhibitor, e.g., a GSKβ inhibitor. GSK inhibitors are known widely in the art and can be grouped into different chemical classes such as pyrroloazepine, flavone, beruazepinone, bis-indole, pyrrolopyrazine, pyridyloxadiazole, pyrazolopyridine, pyrazolopyridazine, aminopyridine, pyrazoloquinoxaline, oxindole (indolinone), thiazole, bisindolylmaleimide, azainodolylmaleimide, arylindolemaleimide, aniliomaleimide, phenylaminopyridine, triazole, pyrrolopyrimidine, pyrazolopyrimidine, and chloromethyl thienyl ketone.

Exemplary GSK3 pathway inhibitors include, but are not limited to, 6-Bromoindirubin-3'-oxime (BIO), CHIR98014; CHIR99021; ARA014418; hymenialdisine; flavopiridol; aloisine A; aloisine B; CT20026; SU9516; staurosporine; GF109203x; RO318220; SB216763; SB415286; IS; CGP60474; kenpaullone (9-bromopaullone); alsterpaullone; 2-cyanoethyl-alsterpaullone; 1-aza-alsterpaullone; 1-aza-kenpaullone; 9-cyano-2,3-dimethoxypaullone; 2-iodopaullone; 2-bromo-9-nitropaullone; 2,3-dimethoxy-9-nitropaullone;

7-bromo-5-(4-nitrophenylhydrazono)-4,5-dihydro-1-H-[1]benzazepin2(3H)-one; 7,8-dimethoxy-5-(4-nitrophenylhydrazono)-4,5dihydro-1H-[1]benzazepin-2-(3H)-one; 9-cyanopaullone; 9-chloropaullone; 9-trifluoromethylpaullone; 2,3-dimethoxy-9-trifluoromethylpaullone; 9-bromo-12-methyloxycarbonylmethylpaullone; 9-fluoropaullone; 9-bromo-2,3-dimethoxypaullone; 9-bromo-2,3-dimethoxypaullone; 9-methylpaullone; 10-bromopaullone; 2-bromopaullone; 11-chloropaullone; 2-(3-hydroxy-1-propinyl)-9-trifluoromethylpaullone; 9-bromo-12-(2-hydroxyethyl)-paullone; kenpaullone; Alsterpaullone; 2-cyanoethyl-alsterpaullone; 1-aza-kenpaullone; 1-aza-alsterpaullone; 9-bromo-12-methylpaullone; 9-bromo-5-(methyloxycarbonylmethyl)paullone; 11-methylpaullone; paullone; 11-ethylpaullone; 9-bromo-7,12-dihydro-6-(hydroxyamino)-indolo[2-3-d][1]benzazepine; 2,9-dibromopaullone; 11-bromopaullone; 2,3-dimethoxypaullone; 9-bromo-7,12dihydro-6-methylthio-indolo[2-3-d][1]benzazepine; (E)-2(3-oxo-1-butenyl)-9-trifluoromethylpaullone; 9-bromo-12ethylpaullone; 9-bromo-7,12-dihydro-indolo[2-3-d][1]benzazepine-6(5H)-thione; 2-bromo-9-trifluoromethylpaullone; 2-[2-(1-hydroxycyclohexyl)ethinyl]-9-trifluoromethyl-paullone; 9-bromo-5methylpaullone; 9-methoxypaullone; 2-iodo-9-trifluoromethylpaullone; 9-bromo-12-(tert-butyloxycarbonyl)-paullone; 9-bromo-12-(2-propenyl) paullone; 9-bromo-4-hydroxypaullone; 8,10-dichloropaullone; 5-benzyl-9-bromopaullone; 9-bromo-4-methoxypaullone; 9-bromo-5-ethylpaullone; 9-bromo-5,7bis-(tert-butyloxycarbonyl)-paullone; 4-methoxypaullone; 9-bromo-5,6,7,12-tetrahydrobenzo[6-7]cyclohept[1,2.b]indole; 2-phenyl-4-(2-thienyl)-5H-pyrido[2-3-d][1]benzazepine-6(7H)-thione; 9-bromo-5,7,12-tri-(tert-butyloxycarbonyl)-paullone; 9-bromo-5,12-bis-(tert-butyloxycarbonyl)paullone; 4-(4-chlorophenyl)-2-(2-naphthyl)-5H-pyrido[23-d][1]benzazepine-6(7H)-thione; 5,6,7,12-tetrahydrobenzo[6-7]cyclohept[1,2-b]indole; N-Butyl-N'-(5-nitro-1,3-thiazol-2-yl) urea; N-(5-Nitro-1,3-thiazol-2-yl)pentanamide; 1-{4-Amino-2-[(4-methoxyphenyl)amino]-1,3-thiazol-5-yl}ethanone; N-Benzyl-N'-(5-nitro-1,3-thiazol-2-yl) urea; N-(4-methoxybenzyl)-N'-(5-nitro-1,3-thaizol-2-yl) urea; 3-(4-Methoxyphenyl)-N-(5-nitro-1,3-thiazol-2-yl) propanamide; 4-(4-Methoxyphenyl)-N-(5-nitro-1,3-thiazol-2-yl) butanamide; 2-(3-Methoxyphenyl)-N-(5-nitro-1, 3-thiazol-2yl)acetamide; 2-(4-Fluorophenyl)-N-(5-nitro-1,3-thiazol-2-yl) propanamide; 2-(3-Methylphenyl)-N-(5-nitro-1,3-thiazol-2-yl) acetamide; 1-benzyl-3-naphthalen-1-yl-urea or 1-benzyl[1,3]dioxol-5-yl-3-benzyl-urea.

Additional GSK3 pathway inhibitors, e.g., GSK-3beta inhibitors, amenable to the invention are described in U.S. Pat. Nos. 7,056,939, 7,045,519, 7,037,918, 6,989,382, 6,949,547, 6,872,737, 6,800,632, 6,780,625, 6,608,063, 6,489,344, 6,479,490, 6,441,053, 6,417,185, 6,323,029, 6,316,259, 7,232,814, 7,393,953, and 6,057,117; PCT Patent Application Publication Nos. WO07/017145, WO03/089419, WO 99/65910, and WO09/010298; and Leost at al., *Paullones Are Potent inhibitors of Glycogen Synthase Kinase-3B and Cyclin-dpendent Kinase 5/p25*, Eur. J. Biochem. (2000), 267, 5983-5994, content of all of which is incorporated herein by reference in their entirety of which each are incorporated herein by reference in their entirety.

In one embodiment, the GSK3 pathway inhibitor is BIO.

In some embodiments, the GSK3 pathway inhibitor activates Wnt signaling. The Wnt signaling pathway is known for its important role in the inductive interactions that regulate growth and differentiation, and likely also plays important roles in the homeostatic maintenance of post-embryonic tissue integrity. Wnt stabilizes cytoplasmic β-catenin, which stimulates the expression of genes including c-myc, c jun, fra-1, and cyclin Dl. In addition, misregulation of Wnt signaling can cause developmental defects and is implicated in the genesis of several human cancers. More recently, the Wnt pathway has been implicated in the maintenance of stem or progenitor cells in a growing list of adult tissues that now includes skin, blood, gut, prostate, muscle and the nervous system. Wnt signaling affects fundamental development pathways by regulating cell proliferation and differentiation. As such, the Wnt signaling pathway can be instrumental in the regulation of cell proliferation, differentiation and morphogenesis. Non-limiting examples of Wnt activators include β-catenin, APC, axin1, axin2, GSK3, GSK-3β inhibitors, Disheveled, LRP5, LRP6, Frizzled, Wnt proteins (e.g., Wnt-1, Wnt-3a, Wnt-5a, and Wnt-8a).

In some embodiments, concentration of the GSK3 pathway inhibitor for contacting with the stem cell is from about 0.05 µM to about 50 µM, from about 0.1 µM to about 25 µM, from about 0.2 µM to about 15 µM, from about 0.3 µM to about 5 µM, from about 0.1 µM to about 1 µM, or from about 0.25 µM to about 0.75 µM. In one embodiment, concentration of the GSK3 pathway inhibitor for contacting with the stem cell is about 0.5 µm.

cAMP

In some embodiments, the compound that increases intracellular levels of cAMP is an activator of adenylyl cyclase. Adenylyl cyclase catalyzes the conversion of ATP to 3',5'-cyclic AMP (cAMP) and pyrophosphate. Divalent cations (usually Mg) are generally required and appear to be closely involved in the enzymatic mechanism. The cAMP produced by adenylyl cyclase then serves as a regulatory signal via specific cAMP-binding proteins, either transcription factors or other enzymes (e.g., cAMP-dependent kinases).

An "activator" of an adenylyl cyclase is a compound or composition which causes the adenylyl cyclase to become more active, and thereby elevates the cAMP levels or signal of the cell. The mode of action of the activator can be direct, e.g., through binding the cyclase, or indirect, e.g., through binding another molecule which otherwise interacts with the cyclase.

Exemplary activators of adenylate cyclase, include, but are not limited to, forskolin; forskolin derivatives and analogues; non-hydrolyzable analogues of cAMP including 8-bromo-cAMP, 8-chloro-cAMP, or dibutyryl cAMP (db-cAMP); isoprotenol; vasoactive intestinal peptide; calcium ionophores; membrane depolarization; macrophage-derived factors that stimulate cAMP; agents that stimulate macrophage activation such as zymosan or IFN-γ; phosphodiesterase inhibitors such as pentoxifylline and theophylline; specific phosphodiesterase IV (PDE IV) inhibitors; pituitary adenylate cyclase activating peptide (PACAP); cholera toxin; prostaglandin compounds such as prostaglandin E2 (PGE2); and beta 2-adrenoreceptor agonists such as salbutamol.

In some embodiments, the compound that can increase intracellular cAMP is a G-coupled receptor activator, e.g., a GPCR ligand. The G protein-coupled receptors (GPCRs) form a vast superfamily of cell surface receptors which are characterized by an amino-terminal extracellular domain, a carboxyl-terminal intracellular domain, and a serpentine structure that passes through the cell membrane seven times. Hence, such receptors are sometimes also referred to as seven transmembrane (7TM) receptors. These seven transmembrane domains define three extracellular loops and three intracellular loops, in addition to the amino- and carboxy-terminal domains. The extracellular portions of the receptor have a role in recognizing and binding one or more extracellular binding partners (e.g., ligands), whereas the intracellular portions have a role in recognizing and communicating with downstream molecules in the signal transduction cascade.

As used herein, the term "GPCR ligand" refers to molecules that bind GPCRs. The G protein-coupled receptors bind a variety of ligands including calcium ions, hormones, chemokines, neuropeptides, neurotransmitters, nucleotides, lipids, odorants, and even photons, and are important in the normal (and sometimes the aberrant) function of many cell types. [See generally Strosberg, *Eur. J. Biochem.* 196:1-10 (1991) and Bohm et al, *Biochem J.* 322:1-18 (1997).] When a specific ligand binds to its corresponding receptor, the ligand typically stimulates the receptor to activate a specific heterotrimeric guanine-nucleotide-binding regulatory protein (G-protein) that is coupled to the intracellular portion of the receptor. The G protein in turn transmits a signal to an effector molecule within the cell, by either stimulating or inhibiting the activity of that effector molecule. These effector molecules include adenylate cyclase, phospholipases and ion channels. Adenylate cyclase and phospholipases are enzymes that are involved in the production of the second messenger molecules cAMP, inositol triphosphate and diacyglycerol. It is through this sequence of events that an extracellular ligand stimuli exerts intracellular changes through a G protein-coupled receptor. Each such receptor has its own characteristic primary structure, expression pattern, ligand-binding profile, and intracellular effector system.

GPCRs include receptors for sensory signal mediators (e.g., light and olfactory stimulatory molecules); adenosine, bombesin, bradykinin, endothelin, γ-aminobutyric acid (GABA), hepatocyte growth factor (HGF), melanocortins, neuropeptide Y, opioid peptides, opsins, somatostatin, GH, tachykinins, members of the vasoactive intestinal peptide family, and vasopres sin; biogenic amines (e.g., dopamine, epinephrine, norepinephrine, histamine, glutamate (metabotropic effect), glucagon, acetylcholine (muscarinic effect), and serotonin); chemokines; lipid mediators of inflammation (e.g., prostaglandins, prostanoids, platelet-activating factor, and leukotrienes); and peptide hormones (e.g., calcitonin, C5a anaphylatoxin, follicle-stimulating hormone (FSH), gonadotropin-releasing hormone (GnRH), neurokinin, thyrotropin-releasing hormone (TRH), cannabinoids, and oxytocin). GPCRs that act as receptors for stimuli that have not yet been identified are known as orphan receptors. Whereas, in other types of receptors that have been studied, wherein ligands bind externally to the membrane, the ligands of GPCRs typically bind within the transmembrane domain. However, protease-activated receptors are activated by cleavage of part of their extracellular domain.

Types of GPCR ligands include, but are not limited to: agonists which shift the equilibrium in favor of active states; inverse agonists which shift the equilibrium in favor of inactive states; and neutral antagonists which do not affect the equilibrium. When a GPCR in an active state encounters a G-protein, it can activate the G-protein. GPCRs are the target of about 40% of all prescription pharmaceuticals on the market. (Filmore, Modern Drug Discovery, November 2004, pp. 11). Examples of commonly prescribed GPCR-based drugs include Atenolol (TENORMIN®), Albuterol (VENTOLIN®), Ranitidine (ZANTAC®), Loratadine (CLARITIN®), Hydrocodone (VICODIN®) Theophylline (THEODUR®), and Fluoxetine (PROZAC®).

Exemplary GPCR activators include, but are not limited to, calcitonin, PGE2, corticotropin releasing factor (CRF), urocortin 1, urocortin 2, usorcortin 3, parathyroid hormone, PTH-related hormone, TIP39, amylin, CGRP (CALCA and CALCB), adrenomedullin, secretin, VIP, PACAP, glucagon, GHRH, GLP-1, GLP-2, Dynorphin A, Dynorphin A amide, Dynorphin A (1-6), Dynorphin A (1-13), Dynorphin A (2-13), Dynorphin A (2-17), MetEnk, Met-Enk-RF-amide, Met-Enk-Arg-Phe, Met-Enk-Glyleu, [D-pGlul, D-Phe2, D-Trp3,6]-LH-RH, gl-MSH amide, g2-MSH, [N-MePheI, D-Pro4]-Morphiceptin (PL017), ACTH (Human), Leu-Enk, Adrenomedullin (22-52), Adrenomedullin (26-52) (Human) (ADM antagonist), Agouti 1-40 Amide, Agouti Related Protein (87-132)-Amide, Alpha-MSH, Alpha-Neo-Endorphin, Amylin Amide, BAM(I-20), BAM(I-22), BAM(2-22), BAM(6-22), BAM(I-20), ANP (Atrial Natriuretic Peptide), Anti-inflammatory Peptide 1, Anti-inflammatory Peptide 2, (3-endorphin, Benzylureido-Met-Leu-Phe, Beta-ANP, Beta-Endorphin, Beta-MSH, Big Endothelin-1, Big Gastrin-1, BNP (Brain Natriuretic Peptide-32), BNP-45 (Cardiac Natriuretic Peptide, Bombesin, BAM(8-25), BAM(8-20), FLRF, Calcitonin Gene Related Peptide, NPFF, Calcitonin, Calcitonin Gene Related Peptide (8-37), CART (55-1,02), CART (55102)[Met(O)67, CART (61-102), CGRP (8-37), CGRP II, Cholecystokinin Octapeptide [CCK(26-33)], Cholecystokinin-33, CNP-22 (C-Type Natriuretic Peptide), Corticotropin Releasing Factor, Cortistatin-14, NPAF, SST, NPY, FMRFamide (SEQ ID NO: 39), OrpaninFQFMRF amide related peptide (SEQ ID NO: 40), YMRFamide (SEQ ID NO: 41), YLPLRFamide (SEQ ID NO: 42), YFMRFamide (SEQ ID NO: 43), LPLRFamide (SEQ ID NO: 44), dFMRFamide, W-Nle-R-F-amide, and ACEP. Polypeptide activstors of GPCRs include, but are not limited to, vasopressin, oxytocin, somatostatin, neuropeptide Y, GnRH, leutinizing hormone, follicle stimulating hormone, parathyroid hormone, orexins, urotensin II, endorphins, enkephalins, and the like. A list of GPCR modulators, including activators, is compiled on the web at pharminfo.pharm.kyoto-u.ac.jp/services/glida/ligand_classification.php.

In some embodiments, the G-coupled receptor activator is calcitonin or PGE2.

In some embodiments, the compound that can increase intracellular cAMP is forskolin.

In some embodiments, concentration of the compound that increases intracellular cAMP is from about 0.1 µM to about 500 µM, from about 1 µM to about 250 µM, from about 2.5 µM to about 150 µM, from about 5 µM to about 100 µM, from about 7.5 µM to about 75 µM, from about 10 µM to about 50 µM, or from about 15 µM to about 25 µM.

In one embodiment, concentration of the compound is about 20 µM.

FGF Pathway

As used herein, a "FGF pathway activator" refers to compounds and compositions that can increase or enhance the activity of at least one component of the FGF pathway. The definition and details of the FGF pathway are disclosed in the art e.g., Lee P. L. et al., Science. 245, 57-60 (1989); Mignatti P. et al., J. Cell Physiol. 151, 81-93 (1992); Miki T et al., Proc. Natl. Acad. Sci. USA. 89, 246-250 (1992); Gringel S. et al., J. Biol. Chem. 385, 1203-1208 (2004); Ornitz D. M. and Itoh, N. Genome Biol. 2, 1-12 (2001); Sorensen V. et al., Bioessays. 28, 504-514 (2006); Coulson E. J. *Prog. Brain Res.* 146, 41-62 (2004); Huang E. J. and Reichardt L. F. *Annu. Rev. Biochem.* 72, 609-642 (2003); Miller F. D. and Kaplan D. R. *Cell Mol. Life Sci.* 58, 1045-1053 (2001); and Rabizadeh S. and Bredesen D. E.

*Cytokine Growth Factor Rev.* 14, 225-239 (2003), content of all of which is incorporated herein by reference in their entirety.

In some embodiments, the FGF pathway activator is an activator of PI-3K pathway. PI3Ks interact with the IRS (Insulin receptor substrate) in order to regulate glucose uptake through a series of phosphorylation events. The phosphoinositol-3-kinase family is composed of Class I, II and Class III, with Class I the only ones able to convert PI(4,5)P2 to PI(3,4,5)P3 on the inner leaflet of the plasma membrane. Class I PI3K are heterodimeric molecules composed of a regulatory and a catalytic subunit; they are further divided between IA and IB subsets on sequence similarity. The PI3K pathway also recruits many other proteins downstream, including mTOR, GSK3β, and PSD-95. The PI3K-mTOR pathway leads to the phosphorylation of p70S6K, a kinase which facilitates translational activity.

In some embodiments, the activator of the PI-3K pathway activates phosphatidylinositide 3-kinase (PI3K), phosphoinositide dependent kinase (PDK) or protein kinase B (PKB, aka Akt). Phosphoinositide 3-kinases (PI 3-kinases or PI3Ks) are a family of related enzymes that are capable of phosphorylating the 3 position hydroxyl group of the inositol ring of phosphatidylinositol (PtdIns). They are also known as phosphatidylinositol-3-kinases. An "activator" of a PI3K is a compound or composition which causes the PI3K to become more active. The mode of action of the activator can be direct, e.g., through binding the cyclase, or indirect, e.g., through binding another molecule which otherwise interacts with the cyclase.

In some embodiments, the activator of the FGF pathway is a growth factor, e.g., a fibroblast growth factor (FGF), epidermal growth factor (EGF), nerve growth factor (NGF), or transforming growth factor (tumor growth factor, TGF).

Exemplary activators of the FGF pathway include, but are not limited to, basic fibroblast growth factor (bFGF, FGF2 or FGF-β); TGFα; TGFβ; EGF; NGF; Akt activators, such as Ro-31-8220 (Wen, H. et al., Cellular signaling, 15:37-45 (2003)); Nicotine (West, K. et al., J. Clinical Investigation, 111:81-90 (2003)); carbachol (Cui Q L, Fogle E & Almazan G Neurochem Int, 48:383-393 (2006)); 4-(methylnitrosamino)-1-(3-pyridyl)-1-butanone (NNK) (West, K. et al., J. Clinical Investigation, 111:81-90 (2003)); adrenomedullin (AM) (Nikitenko, L L et al, British J. Cancer, 94:1-7 (2006)); lysophosphatidic acid; platelet activating factor, macrophage simulating factor; sphingosine-1-phosphate; cAMP-elevating agents, such as forskolin, chlorophenylthio-cAMP, prostaglandin-El, and 8-bromo-cAMP (Song et al., J. Cell. Mol. Med., 9(1):59-71 (2005)), insulin and insulin growth factor-1 (Datta, S. R., et al., Cell, 91:231-241 (1997)), and platelet derived growth factor.

In one embodiment, activator of the FGF pathway is bFGF. Other exemplary FGF pathway include FGF1, FGF2, FGF3, FGF4, FGF5, FGF6, FGF7, FGF8, FGF9, FGF10, and the like.

In some embodiments, concentration of the FGF pathway activator for contacting with the stem cell is about 0.25 ng/ml to about 100 ng/ml, about 0.5 ng/ml to about 75 ng/ml, about 1 ng/ml to about 50 ng/ml, about 2.5 ng/ml to about 25 ng/ml, from about 5 ng/ml to about 15 ng/ml, or about 7.5 ng/ml to about 12.5 ng/ml. In one embodiment, concentration of the activator is about 10 ng/ml.

Proliferation of Satellite Cells

In one aspect, the present disclosure provides a method of inducing, enhancing or increasing satellite cell proliferation. The method comprising contacting a satellite cell with an compound that increases intracellular levels of 3',5'-cyclic adenosine monophosphate (cAMP). The satellite cell to be contacted can be in vitro, ex vivo or in vivo. Compounds that increase intracellular levels of cAMP are described elsewhere herein.

As used herein, the terms "proliferating" and "proliferation" refer to an increase in the number of cells in a population (growth) by means of cell division. Cell proliferation is generally understood to result from the coordinated activation of multiple signal transduction pathways in response to the environment, including growth factors and other mitogens. Cell proliferation can also be promoted by release from the actions of intra- or extracellular signals and mechanisms that block or negatively affect cell proliferation.

As used herein, "inducing,", "enhancing," or "increasing" satellite cell proliferation means that satellite cells replicate at a faster rate and/or more frequently. In some embodiments of this and other aspects described herein, satellite cell proliferation is increased by at least 5%, 10%, 20%, 30%, 40%, 50%, 50%, 70%, 80%, 90%, 1-fold, 1.1-fold, 1.5-fold, 2-fold, 3-fold, 4-fold, 5-fold, 10-fold, 50-fold, 100-fold or more higher relative to an untreated control. The % or fold increase in satellite cell proliferation can be determined by measuring number of replicating satellite cells while in contact with a compound described herein relative to a control where the satellite cells are not in contact with the compound. Increase in proliferation can also be based on ratios of replicating cells to total number of cells in the respective treated and untreated control. In some embodiments, total number of cells in the treated and untreated controls is used to determine the proliferation. Satellite cell proliferation can be determined using the BrdU incorporation method described in U.S. Patent Publication No. 2009/0136481, content of which is incorporated herein by reference.

Myosatellite cells or satellite cells are small mononuclear progenitor cells with virtually no cytoplasm found in mature muscle. They are found sandwiched between the basement membrane and sarcolemma (cell membrane) of individual muscle fibers, and can be difficult to distinguish from the sub-sarcolemmal nuclei of the fibers. Satellite cells are able to differentiate and fuse to augment existing muscle fibers and to form new fibers. These cells represent the oldest known adult stem cell niche, and are involved in the normal growth of muscle, as well as regeneration following injury or disease.

In undamaged muscle, the majority of satellite cells are quiescent; they neither differentiate nor undergo cell division. In response to mechanical strain, satellite cells become activated. Activated satellite cells initially proliferate as skeletal myoblasts before undergoing myogenic differentiation.

Markers characteristic of satellite cells include the expression of cell surface proteins or the encoding genes, the expression of intracellular proteins or the encoding genes, cell morphological characteristics, and the like. Those skilled in the art will recognize that known immunofluorescent, immunochemical, polymerase chain reaction, in situ hybridization, Northern blot analysis, chemical or radiochemical or biological methods can readily ascertain the presence or absence of satellite cell specific characteristics.

If desired, the type(s) of cells in a population of satellite can be determined using techniques that are well known in the art. For example, the use of cell-type specific stains. Alternatively, one can perform immunofluorescence staining using antibodies directed to various satellite cell specific proteins. In addition, a cell type can be determined by its morphology using techniques such as, for example, light microscopy, or electron microscopy.

Satellite cells express a number of distinctive genetic markers. For example, current thinking is that all satellite cells express PAX7 and PAX3 (F. Rlaix et al. Nature, 2005, 435(7044): 898-899). Activated satellite cells express myogenic transcription factors, such as Myf5 and MyoD. They also begin expressing muscle-specific filament proteins such as desmin as they differentiate. The data presented herein shows that CXCR4 and β-1 Integrins are also useful surrogate markers for satellite cells, especially engraftable myogenic cells.

Little is known of the regulation of satellite cells. Whilst together PAX3 and PAX7 currently form the definitive satellite markers, Pax genes can be poor transcriptional activators. The dynamics of activation and quiesence and the induction of the myogenic program through the myogenic regulatory factors, Myf5, MyoD, myogenin, and MRF4 remains to be determined. There is also some research indicating that satellite cells are negatively regulated by a protein called myostatin.

In some embodiments, the satellite cells are in a stabilized state, e.g., the cells were taken from a subject and treated in such a manner as to allow them to be stored for some period of time. For example, the cells can be frozen, e.g., using methods known in the art for freezing primary cells, such that the cells are viable when thawed. For example, methods known in the art to freeze and thaw embryos to generate live mammals can be adapted for use in the present methods. Such methods can include the use of liquid nitrogen, e.g., with one or more cryoprotectants, e.g., agents that prevent freeze-thaw damage to the cell.

The satellite cell population can be contacted with the compound that increases intracellular level of cAMP in a cell culture e.g., in vitro or ex vivo, or the compound can be administrated to a subject, e.g., in vivo. In some embodiments of the invention, a compound that increases intracellular level of cAMP can be administrated to a subject for repairing or regenerating a damaged muscle tissue.

The term "contacting" or "contact" as used herein in connection with contacting a population of satellite cells includes subjecting the satellite cells to an appropriate culture media which comprises the indicated compound. Where the satellite cell population is in vivo, "contacting" or "contact" includes administering the compound in a pharmaceutical composition to a subject via an appropriate administration route such that the compound contacts the satellite cell population in vivo.

For in vivo methods, a therapeutically effective amount of the indicated compound can be administered to a subject. Methods of administering compounds to a subject are known in the art and easily available to one of skill in the art. Promoting satellite cell proliferation in a subject can lead to treatment, prevention or amelioration of a number of diseases, disorders or conditions which are caused by a damaged muscle tissue.

Satellite cells suitable for use in ex vivo methods can be obtained from subject according to methods well known to those skilled in the art. The term "ex vivo" refers to cells which are removed from a living organism and cultured outside the organism (e.g., in a test tube). For ex vivo methods, satellite cells can include autologous satellite cells, i.e., a cell or cells taken from a subject who is in need of treatment for muscle damage or repair. Autologous satellite cells have the advantage of avoiding any immunologically-based rejection of the cells. Alternatively, the cells can be heterologous, e.g., taken from a donor. The second subject can be of the same or different species. Typically, when the cells come from a donor, they will be from a donor who is sufficiently immunologically compatible with the recipient, i.e., will not be subject to transplant rejection, to lessen or remove the need for immunosuppression. In some embodiments, the cells are taken from a xenogeneic source, i.e., a non-human mammal that has been genetically engineered to be sufficiently immunologically compatible with the recipient, or the recipient's species. Methods for determining immunological compatibility are known in the art, and include tissue typing to assess donor-recipient compatibility for HLA and ABO determinants. See, e.g., *Transplantation Immunology*, Bach and Auchincloss, Eds. (Wiley, John & Sons, Incorporated 1994).

Without wishing to be bound by theory any suitable cell culture media can be used for the in vitro or ex vivo methods described herein. After in vitro or ex vivo contact with a compound that increases intracellular level of cAMP, when the satellite cells have reached a desired population number or density, e.g., about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, or more cells, the cells can be transplanted in a subject who is in need of treatment for muscle repair or damage. The cells can be transplanted in a subject from whom the cells were originally obtained or in different subject.

Satellite cells prepared in accordance with the method disclosed herein can be used for transplantation. In some embodiments, the satellite cells prepared in accordance with the method are autologous to the subject which will receive the transplantation. Satellite cells prepared in accordance with the method disclosed herein can be used for transplantation in a subject for repairing or regenerating a damaged muscle tissue or increasing muscle mass of the subject.

The present disclosure also provides a cell population comprising satellite cells produced by the method disclosed herein. The cell population can be a purified population of satellite cells. The purified satellite cells can be obtained by sorting out the cell culture obtained by the method disclosed herein. In some embodiments, one or more kind of cells other than the satellite cells can be co-present in the cell population.

In another aspect, provided herein is a method for repairing or regenerating a damaged muscle tissue or increasing muscle mass of a subject of a subject. The method comprising administering to the subject a therapeutically effective amount of a compound that increases intracellular levels of cAMP.

Compositions

In one aspect provided herein is a composition for inducing differentiation of a stem cell into a myogenic cell, the composition comprising: at least two of: (i) a GSK3 pathway inhibitor; (ii) a compound that increases intracellular levels of 3',5'-cyclic adenosine monophosphate (cAMP); and (iii) a FGF pathway activator.

Without wishing to be bound by a theory, the components of the composition disclosed herein can have a synergistic effect on differentiation of stem cell into myogenic cells. The term "synergistic" as used herein is defined to mean a combination of components wherein the activity of the combination is greater than the additive of the individual activities of each component of the combination. In some embodiments, the activity of the combination is at least 5%, at least 10%, at least 15%, at least 20%, at least 25%, at least 30%, at least 40%, at least 50%, at least 60%, at least 70%, at least 80%, at least 90%, at least 1-fold, at least 2-fold, at least 3-fold, at least 4-fold, at least 5-fold, at least 10-fold, at least 50-fold, at least 100-fold or greater than the additive of the individual activities of each component of the combination.

Ratio of the components of the composition can be chosen to provide optimum activity. For example, when present, the GSK3 pathway inhibitor and the compound that increases intracellular levels of cAMP can be in a ratio from about 10:1 to about 1:1,000; from about 5:1 to about 1:500; from about 1:1 to about 1:250; from about 1:5 to about 1:200; from about 1:10 to about 1:100; from about 1:20 to about 1:75; or from about 1:25 to 1:75. In one embodiment, the GSK3 pathway inhibitor and the compound that increases intracellular levels of cAMP can be in a ratio of about 1:40. The ratio can be a molar ratio or mass ratio.

When present, FGF pathway activator and the GSK3 pathway inhibitor can be in a ratio from about 1:50 to about 1:2,000; from about 1:100 to about 1:1,750; from about 1:200 to about 1:1,500; from about 1:500 to about 1:1,250; or from about 1:750 to about 1:1,000. In one embodiment, the FGF pathway activator to the GSK3 pathway inhibitor can be in ratio of about 1:875. The ratio can be a molar ratio or mass ratio.

When present, FGF pathway activator and the compound that increases intracellular levels of cAMP can be in a ratio from about 1:10,000 to about 1:100,000, from about 1:15,000 to about 1:75,000; from about 1:20,000 to about 1:50,000; from about 1:25,000 to about 1:45,000, or from about 1:30,000 to about 1:40,000. In one embodiment, the FGF pathway activator to the compound that increases intracellular levels of cAMP can be in ratio of about 1:35,000. The ratio can be a molar ratio or mass ratio.

In some embodiments, the composition is formulated with a pharmaceutically acceptable carrier (additive), i.e., a pharmaceutically acceptable composition. In some embodiments, the pharmaceutically acceptable composition comprises therapeutically effective amount of at least two of: (i) a GSK3 pathway inhibitor; (ii) a compound that increases intracellular levels of 3',5'-cyclic adenosine monophosphate (cAMP); and (iii) a FGF pathway activator. The composition can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Kits

In one aspect provided herein is a reagent kit for inducing differentiation of a pluripotent stem cell into a skeletal muscle cell, the kit comprising: (i) at least two of: (a) a GSK3 pathway inhibitor; (b) a compound that increases intracellular levels of 3',5'-cyclic adenosine monophosphate (cAMP); and (c) a FGF pathway activator; and (ii) instructions for use. In some embodiments, the kit comprises a GSK3 pathway inhibitor; a compound that increases intracellular levels of 3',5'-cyclic adenosine monophosphate (cAMP); and a FGF pathway activator.

In some embodiments, the kit further comprises a stem cell.

Screening Assay

In one aspect provided herein is a method for screening chemical compounds or compositions in blastomere cells, e.g., zebrafish blastomeres. The embodiments of the disclosure provide a system for screening organ development modulators. More specifically, the present disclosure provides for screening, including high throughput screening, for modulators that effect organ development and function. In some embodiments, the screening assay utilizes zebrafish blastomeres.

Using the present invention, one can distinguish at least three different classes of compounds that increase, decrease or otherwise modulate organ development and function. Specificity is high in this well-defined novel assay, providing deeper and broader information including obtaining compounds that can induce differentiation of a pluripotent cell to a progenitor cell of a specific lineage; compounds that can inhibit differentiation of progenitor cells to fully differentiated cells; and compounds that induce differentiation of progenitor cells to fully differentiated cells. Thus, without wishing to be bound by a theory, the screening assay can be used to probe the pathway of a pluripotent cell to a fully differentiated cell and modulators of that pathway.

Generally, the method comprises the steps of culturing blastomere in presence of a test compound, wherein at least one cell in the cell culture comprises a reporter gene, wherein the reporter gene encodes a cell lineage specific marker and produces a detectable signal when expressed; and measuring/detecting the detectable signal. A change in level or amount of the detectable signal indicating that the test compound modulates the development of cell lineage and organs and tissue comprising cells that express the reporter gene. The level or amount of the detectable signal can be determined relative to a reference or control. In some embodiments, the reference or control can be a blastomere culture without the test compound.

As used herein, the term "reporter gene" refers to a gene that expresses a cell marker that is expressed in a cell lineage specific manner and produces a detectable response or signal. As used herein, the term "detectable" refers to a molecule or an element or functional group in a molecule that allows for the detection, imaging, and/or monitoring of the presence the molecule. The reporter gene can be an endogenous gene, an exogenous gene, or a transgene. A detectable response generally refers to a change in, or occurrence of, a signal that is detectable either by observation or instrumentally. Without limitations, the expressed molecule can be detected directly or the molecule can produce a detectable signal in the presence of a reagent. Further, any available method for determining the amount of the reporter in a culture can be employed. In some embodiments, detectable response is an optical signal, i.e., the reporter is an optical reporter. Suitable optical reporters include, but are not limited to, fluorescent reporters and chemiluminescent groups.

In some embodiments, the detectable response is fluorescence or a change in fluorescence, e.g., a change in fluorescence intensity, fluorescence excitation or emission wavelength distribution, fluorescence lifetime, and/or fluorescence polarization. In some embodiments, the reporter gene encodes a fusion protein comprising a cell lineage specific marker (CLSM) fused with a fluorescent protein (i.e., a CLSM:FP construct or fusion protein).

The cell lineage specific marker can be a marker that is expressed only in the progenitor cells of the lineage; expressed only in the terminally differentiated cells of the lineage; or expressed in both the progenitor cells and the terminally differentiated cells of the lineage.

Thus, in some embodiments, the blastomere cells can comprise two or more different reporter genes, each reporter gene encoding a different detectable cell lineage specific marker. One reporter gene can be expressed in the terminally differentiated cells, a second reporter gene can be expressed in the progenitor cells, and at least one of the two reporter genes is not expressed in both the progenitor cells and the terminally differentiated cells. In some embodiments, the blastomere cells comprise two different reporter genes, each encoding a fused protein comprising a cell lineage specific marker fused to a different fluorescent protein. For example, the cell can comprise a first reporter gene encoding a first CLSM:FP construct/fusion protein and a second reporter gene encoding a second CLSM:FP construct/fusion protein wherein the CLSM and FP in the first construct/fusion protein are different from the CLSM and FP in the second construct/fusion protein. In some further embodiments of this, one of the CLSM:FP construct can comprise a marker that is also expressed in a progenitor cell of the cell lineage, while the second CLSM:FP construct comprises a marker that is preferentially expressed in the terminally differentiated cells of the cell lineage. For example, the first reporter gene can encode a cell lineage progenitor cell specific marker (CLPCSM) fused with a fluorescent protein (i.e., a CLPCSM:FP construct) and the second reporter gene can encode a terminally differentiated cell lineage specific marker with a fluorescent protein (i.e., a DCSLM:FP construct). BY a "terminally differentiated cell lineage marker" is meant a cell marker that is present only in the terminally differentiated cells. Without limitations, cells comprising the two different reporter genes can be used to screen for compounds that modulate differentiation of pluripotent cells into progenitor cells; differentiation of progenitor cells into fully differentiated cells; or differentiation of pluripotent cells into fully differentiation cells.

In some embodiments, the cell lineage specific marker can be a marker of a myogenic cell. In some embodiments, the cell lineage specific marker is a marker of myogenic progenitor cells. In some embodiments, the cell lineage specific marker is a maker of mesodermal cells. Myogenic, myogenic progenitor, and mesodermal lineage markers are described elsewhere in the disclosure.

Examples of fluorescent proteins suitable for use include, but are not limited to, green fluorescent protein, red fluorescent protein (e.g., DsRed), yellow fluorescent protein, cyan fluorescent protein, blue fluorescent protein, and variants thereof (see, e.g., U.S. Pat. Nos. 6,403,374, 6,800,733, and 7,157,566). Specific examples of GFP variants include, but are not limited to, enhanced GFP (EGFP), destabilized EGFP, the GFP variants described in Doan et al, *Mol. Microbiol*, 55:1767-1781 (2005), the GFP variant described in Crameri et al, *Nat. Biotechnol.*, 14:315319 (1996), the cerulean fluorescent proteins described in Rizzo et al, *Nat. Biotechnol*, 22:445 (2004) and Tsien, *Annu. Rev. Biochem.*, 67:509 (1998), and the yellow fluorescent protein described in Nagal et al, *Nat. Biotechnol.*, 20:87-90 (2002). DsRed variants are described in, e.g., Shaner et al, *Nat. Biotechnol.*, 22:1567-1572 (2004), and include mStrawberry, mCherry, morange, mBanana, mHoneydew, and mTangerine. Additional DsRed variants are described in, e.g., Wang et al, *Proc. Natl. Acad. Sci. U.S.A.*, 101:16745-16749 (2004) and include mRaspberry and mPlum. Further examples of DsRed variants include mRFPmars described in Fischer et al, *FEBS Lett.*, 577:227-232 (2004) and mRFPruby described in Fischer et al, *FEBS Lett*, 580:2495-2502 (2006).

Other non-limiting list of fluorescent proteins includes AceGFP, AcGFP1, AmCyan1, AQ143, AsRed2, Azami-Green (mAG), Cerulean, Cerulean, Citrine, cOFP, CopGFP, Cyan, CyPet, Dronpa, DsRed/DsRed2/DsRed-Express, DsRed-Monomer, EBFP, ECFP, EGFP, Emerald, eqFP611, EYFP, GFPs, HcRed1, HcRed-tandem, J-Red, Kaede, KFP, KikGR, mBanana, mCFP, mCherry, mCitrine, mEosEP, mHoneydew, MiCy, mKO, mOrange, mPlum, mRaspberry, mRFP1, mStrawberry, mTangerine, mYFP, mYFP, mYFP, PA-GFP, PA-mRFP, PhiYFP, PS-CFP-2, Renilla, tdEosFP, tdTomato, T-Sapphire, TurboGFP, UV-T-Sapphire, Venus, YPet, ZsYellow1, and derivatives and analogs thereof. In one embodiment, the fluorescent protein is Green Fluorescent Protein (GFP).

One of skill in the art is well aware of methods for constructing reporter genes that encode fusion proteins comprising fluorescent proteins.

Specific devices or methods known in the art for the detection of fluorescence, e.g., from fluorophores or fluorescent proteins, include, but are not limited to, in vivo near-infrared fluorescence (see, e.g., Frangioni, *Curr. Opin. Chem. Biol,* 7:626-634 (2003)), the Maestro™ in vivo fluorescence imaging system (Cambridge Research & Instrumentation, Inc.; Woburn, Mass.), in vivo fluorescence imaging using a flying-spot scanner (see, e.g., Ramanujam et al, *IEEE Transactions on Biomedical Engineering,* 48:1034-1041 (2001), and the like. Other methods or devices for detecting an optical response include, without limitation, visual inspection, CCD cameras, video cameras, photographic film, laser-scanning devices, fluorometers, photodiodes, quantum counters, epifluorescence microscopes, scanning microscopes, flow cytometers, fluorescence microplate readers, or signal amplification using photomultiplier tubes.

In some embodiments, the FP can be Green fluorescent protein (GFP) or mCherry.

In some embodiments, the reporter gene encodes a fusion protein comprising Myf5 and GFP. In some embodiments, the reporter gene encodes a fusion protein comprising mylz2 and mCherry.

The term "blastomere" is used throughout to refer to at least one blastomere (e.g., 1, 2, 3, 4, etc. . . . ) obtained from an embryo. The term "cluster of two or more blastomeres" is used interchangeably with "blastomere-derived outgrowths" to refer to the cells generated during the in vitro culture of a blastomere. For example, after a blastomere is obtained from an embryo and initially cultured, it generally divides at least once to produce a cluster of two or more blastomeres (also known as a blastomere-derived outgrowth). The cluster can be further cultured with embryonic or fetal cells. Ultimately, the blastomere-derived outgrowths will continue to divide. From these structures, ES cells, TS cells, and partially differentiated cell types can develop over the course of the culture method.

The blastomere can be removed from an embryo at various developmental stages prior to implantation including but not limited to: before compaction of the morula, during compaction of the morula, right after compaction of the morula, before formation of the blastocoel or during the blastocyst stage. In some embodiments, a blastomere (one blastomere, two blastomeres, or more than two blastomeres) are from oblong-stage embryos. The oblong-stage embryos can be dissociated to obtain the blastomeres.

For the screening assay disclosed herein, the blastomere can be obtained from any source available to the practitioner or one of skill in the art. In some embodiments, the blastomere is from zebrafish. As used herein, the term "zebrafish" refers to any fish or strain of fish that is considered to be of the genus and species *Danio rerio*. In some embodiments, the blastomere can be from a transgenic species that expresses a cell lineage specific marker fused with a fluorescent protein. One of skill in the ordinary skill in the art is well aware of methods fro producing transgenic zebrafish and can easily use these methods for producing transgenic zebrafush from which the blastomeres for the screening assay can be obtained. See, for example, Gabriela, et al., BMC Developmental Biology 2007, 7:62 (doi:10.1186/1471-213X-7-62), content of which is incorporated herein by reference in its entirety.

Culture media for culturing the blastomere can be any suitable media available to one of skill in the art for culturing blastomeres. For example, one can use zESC medium, which is composed of 70% LDF medium and 30% RTS34st-conditioned medium, as discussed in the Examples section herein.

For the assay, blastomere can be optionally allowed to grow for a period time before contacting with the test compound. In some embodiments, a practitioner can obtain blastomeres that are already planted in the appropriate vessel and allowed to grow for a period of time. In other embodiments, the practitioner plates the blastomeres in the appropriate vessel and allow them to grow for a period time, e.g., at least one day, at least two days, at least three days, at least four days, at least five days, at least six days, at least seven days or more before contacting with the test compound.

After the test compound has been in contact with the cell for a sufficient period of time, amount of reporter (e.g., expression or activity) is measured and compared to a control or reference. For example, contact time can be from seconds to days or weeks. The practitioner can optimized the contact time for obtaining an optimal signal-to-noise ratio, time constraints, amount of test compound to be tested, number of cells, test volume, availability of reagents for the assay, and the like.

As used herein, the term "test compound" refers to compounds and/or compositions that are to be screened for their ability to stimulate and/or increase and/or promote motor neuron survival. The test compounds can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; an extract made from biological materials such as bacteria, plants, fungi, or animal cells; animal tissues; naturally occurring or synthetic compositions; and any combinations thereof. In some embodiments, the test compound is a small molecule.

The number of possible test compounds runs into millions. Methods for developing small molecule, polymeric and genome based libraries are described, for example, in Ding, et al. J Am. Chem. Soc. 124: 1594-1596 (2002) and Lynn, et al., J. Am. Chem. Soc. 123: 8155-8156 (2001). Commercially available compound libraries can be obtained from, e.g., ArQule, Pharmacopia, graffinity, Panvera, Vitas-M Lab, Biomol International and Oxford. These libraries can be screened using the screening devices and methods described herein. Chemical compound libraries such as those from NIH Roadmap, Molecular Libraries Screening Centers Network (MLSCN) can also be used. A comprehensive list of compound libraries can be found at www.broad.harvard.edu/chembio/platform/screening/compound_libraries/index.htm. A chemical library or compound library is a collection of stored chemicals usually used ultimately in high-throughput screening or industrial manufacture. The chemical library can consist in simple terms of a series of stored chemicals. Each chemical has associated information stored in some kind of database with information such as the chemical structure, purity, quantity, and physiochemical characteristics of the compound.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

Depending upon the particular embodiment being practiced, the test compounds can be provided free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds can be screened individually, or in groups. Group screening is particularly useful where hit rates for effective test compounds are expected to be low such that one would not expect more than one positive result for a given group. Group screening is also useful for determining hits that can act synergistically.

The test compound can be tested at any desired concentration. For example, the test compound can be tested at a final concentration of from 0.01 nm to about 10 mM. Further, the test can be tested at 2 or more (e.g., 2, 3, 4, 5, 6, 7, 8, 9, 10 or more) different concentrations. This can be helpful if the test compound is active only in a range of concentration. When the test compound is tested at 2 or more different concentrations, the concentration difference can range from 10-10,000 fold (e.g., 10-5000 fold, 10-1000 fold, 10-500 fold, or 10-250 fold).

The screening assay can be performed in any suitable container or apparatus available to one of skill in the art for cell culturing. For example, the assay can be performed in 24-, 96-, or 384-well plates. In one embodiment, the assay is performed in a 384-well plate.

In some embodiments, the screening method is a high-throughput screening. High-throughput screening (HTS) is a method for scientific experimentation that uses robotics, data processing and control software, liquid handling devices, and sensitive detectors. High-Throughput Screening or HTS allows a researcher to quickly conduct millions of biochemical, genetic or pharmacological tests. High-Throughput Screening are well known to one skilled in the art, for example, those described in U.S. Pat. Nos. 5,976,813; 6,472,144; 6,692,856; 6,824,982; and 7,091,048, and contents of each of which is herein incorporated by reference in its entirety.

HTS uses automation to run a screen of an assay against a library of candidate compounds. An assay is a test for specific activity: usually inhibition or stimulation of a biochemical or biological mechanism. Typical HTS screening libraries or "decks" can contain from 100,000 to more than 2,000,000 compounds.

The key labware or testing vessel of HTS is the microtiter plate: a small container, usually disposable and made of plastic, which features a grid of small, open divots called wells. Modern microplates for HTS generally have either 384, 1536, or 3456 wells. These are all multiples of 96, reflecting the original 96 well microplate with 8×12 9 mm spaced wells.

To prepare for an assay, the researcher fills each well of the plate with the appropriate reagents that he or she wishes to conduct the experiment with, such as a blastomere cell or population. After some incubation time has passed to allow the reagent to absorb, bind to, or otherwise react (or fail to react) with the compounds in the wells, measurements are taken across all the plate's wells, either manually or by a machine. Manual measurements are often necessary when the researcher is using microscopy to (for example) seek changes that a computer could not easily determine by itself. Otherwise, a specialized automated analysis machine can run a number of experiments on the wells such as colorimetric measurements, radioactivity counting, etc. In this case, the machine outputs the result of each experiment as a grid of numeric values, with each number mapping to the value obtained from a single well. A high-capacity analysis machine can measure dozens of plates in the space of a few minutes like this, generating thousands of experimental data points very quickly.

Screening using zebrafish embryos is useful for the study of development, disease, and stem cell biology. However, the required manual manipulation of zebrafish embryos prevents capitalizing on recent innovations in high-speed pipetting and imaging. Compared to screening using zebrafish embryos, the screening assay described herein is highly automatic, taking one sixth of the time, and consumes only one tenth of the embryo. Such throughput enables screening of larger chemical libraries and can be used for screening of a genetic mutant suppressor. For example, several zebrafish anemia mutants, including cia, edy, and weh, have defects in iron metabolism and lack benzidine staining, a marker for mature erythrocytes. The screening assay of the present disclosure can be designed to screen for chemicals that restore benzidine staining. Without wishing to be bound by a theory, the chemicals identified can be used to treat these iron metabolism defects.

Transgenic zebrafish with a fluorescent reporter that labels a cell or tissue of interest are widely used in the study of development and stem cell biology. Despite the pioneering of transgenic reporter lines for screening, readout by WISH is usually preferred. Compared to WISH, transgenic reporters are usually thought to be less sensitive to detect a difference. Moreover, transgenic embryos need to be fixed and scored immediately. However, the inventors surprising and unexpectedly found that transgenic reporters were useful for the screening assay described herein, mainly because transgenic reporters in a 2-dimensional culture are more sensitive than those in a 3-D embryo. Moreover, because images are automatically captured and stored by imaging cytometers, the cells do not need to be fixed or scored immediately. Further, the screening assay described herein enables combining reporters of different colors, allowing the determination of different developmental states or lineages simultaneously.

Since blastomere cells in culture lack spatial and temporal information, the screening assay described herein uses cellular markers, like transgenic fluorescent reporters. It can be beneficial to combine reporters with different colors to better define a lineage or state. Cell membrane markers, like F-actin and Membrane-GFP, and nuclear markers, like DAPI and H2B-Tomato, can also be used to acquire additional information regarding cellular morphology and cell number. The possibility that a transgenic reporter may behave differently in vitro requires researchers to confirm that the reporter line in culture recapitulates its in vivo expression pattern. Lastly, some lineages can be hard to derive from zebrafish blastomere cells. The inventors circumvented this problem by disassociating embryos at later stages. For example, to study erythrocyte differentiation, the inventors disassociated embryos at 24 hpf, 27 hpf, or 30 hpf, and stained the cells with benzidine. The inventors discovered that cells disassociated at these various stages showed increasing staining, indicating that they are in different stages of erythrocyte development (data not shown). Thus, without wishing to be bound by a theory, a chemical screen using the method disclosed in this disclosure to study erythrocyte development can be designed using benzidine staining.

The screening assay disclosed herein is also a substitute for the ESC/iPSC in studies of lineage differentiation and self-renewal of tissues. Because ESCs/iPSCs can theoretically be induced into any desired tissue for organ repair, they hold promise for treating diseases and injuries that are caused by cellular deficiencies. One major challenge is being able to differentiate ESCs/iPSCs into cells or tissues of interest efficiently. Knowledge gained in developmental biology has guided the design of protocols that differentiate ESCs/iPSCs in ways that recapitulate the progression of embryonic development. However, to obtain homogenous, functional, and transplantable cells or tissues of interest, a more precise understanding of lineage differentiation is needed. To this end, the screening assay described herein offers several major advantages. Firstly, zebrafish blastomere cells develop much faster than mouse and human ESCs/iPSCs, presumably because embryogenesis programs are accelerated in zebrafish. For example, zebrafish blastomere cells form skeletal muscle within 48 hours, while mouse ESCs/iPSCs need approximately 20 days. This allows for faster screening with less variability. Secondly, zebrafish blastomere cells are cultured at 28 degrees, a lower temperature at which chemicals are more stable. Thirdly, the screening assay does not require culture maintenance or sterile manipulation. The fact that a large number of cells can be easily derived from freshly spawned embryos makes the system very cost-efficient. Lastly, the transparent adult zebrafish casper mutant was developed for in vivo stem cell engraftment analysis. Cells or tissues of interest can be transplanted into casper to study engraftment of tissues in vivo.

The development of a robust chemical screening system using blastomere cells is an important complement to studies using embryos. Without wishing to be bound by a theory, other genetic tools like morpholino/siRNA knockdown and mRNA overexpression can be used to enable genome-wide loss-of-function and gain-of-function genetic screening using blastomere cells. A casper based transplantation system can be exploited for the study of engraftment and self-renewal of cells derived from the system. In summary, the data presented herein indicates that the system described herein enables screening using well-established fluorescent transgenic lines and capitalizes on advances in high-speed pipetting and imaging systems. This system can be modified for any cell lineage and can enhance our understanding of developmental biology and to provide insights into cell-based therapies for many diseases.

The disclosure also provides for a cell culture system comprising a population of dissociated blastomere cells that comprise two different fusion protein constructs, each construct comprising a cell lineage specific marker fused with a fluorescent protein.

The present disclosure also provides a compound selected by the screening assay disclosed in this disclosure.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% (e.g., ±4%, ±3%, ±2%, or ±1%) of the value being referred to.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, the term "herein" is used to refer to the whole disclosure and is not meant to be restricted to a specific section or subsection of the disclosure.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used herein, the term "treating" and "treatment" refers to administering to a subject an effective amount of a composition so that the subject as a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (e.g., not worsening) state of disease, delay or slowing of disease progression, amelioration or palliation of the disease state, and remission (whether partial or total), whether detectable or undetectable. In some embodiments, treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis. Alternatively, treatment is "effective" if the progression of a disease is reduced or halted. In some embodiments, the term "treatment" can also mean prolonging survival as compared to expected survival if not receiving treatment. Those in need of treatment include those already diagnosed with a disease or condition, as well as those likely to develop a disease or condition due to genetic susceptibility or other factors which contribute to the disease or condition, such as a non-limiting example, weight, diet and health of a subject are factors which may contribute to a subject likely to develop diabetes mellitus. Those in need of treatment also include subjects in need of medical or surgical attention, care, or management. The subject is usually ill or injured, or at an increased risk of becoming ill relative to an average member of the population and in need of such attention, care, or management.

As used herein, the terms "administering," "introducing" and "transplanting" are used interchangeably in the context of the placement of the cells, e.g., myogenic cells or satellite cells, as disclosed herein, or their differentiated progeny into a subject, by a method or route which results in at least partial localization of the cells, or their differentiated progeny at a desired site. The cells, or their differentiated progeny can be administered directly to a tissue of interest, or alternatively be administered by any appropriate route which results in delivery to a desired location in the subject where at least a portion of the cells or their progeny or components of the cells remain viable. The period of viability of the cells after administration to a subject can be as short as a few hours, e. g. twenty-four hours, to a few days, to as long as several years.

The term "transplantation" as used herein refers to introduction of new cells (e.g. myogenic cells or satellite cells), tissues (such as differentiated cells produced from the cells), or organs into a host (i.e. transplant recipient or transplant subject).

The term "cell culture medium" (also referred to herein as a "culture medium" or "medium") as referred to herein is a medium for culturing cells containing nutrients that maintain cell viability and support proliferation. The cell culture medium can contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

The term "cell line" refers to a population of largely or substantially identical cells that has typically been derived from a single ancestor cell or from a defined and/or substantially identical population of ancestor cells. The cell line may have been or may be capable of being maintained in culture for an extended period (e.g., months, years, for an unlimited period of time). It may have undergone a spontaneous or induced process of transformation conferring an unlimited culture lifespan on the cells. Cell lines include all those cell lines recognized in the art as such. It will be appreciated that cells acquire mutations and possibly epigenetic changes over time such that at least some properties of individual cells of a cell line may differ with respect to each other.

The term "lineages" as used herein describes a cell with a common ancestry or cells with a common developmental fate. By way of an example only, a cell that is of endoderm origin or is "endodermal lineage" means the cell was derived from an endodermal cell and can differentiate along the endodermal lineage restricted pathways, such as one or more developmental lineage pathways which give rise to definitive endoderm cells, which in turn can differentiate into liver cells, *thymus*, pancreas, lung and intestine. A cell that is of mesoderm origin or is "mesodermal lineage" means that the cell was derived from an myogenic cell and can differentiate along the mesodermal lineage restricted pathways, such as one or more myogenic lineage pathways, which give rise to muscle cells, e.g., skeletal muscle cells.

The term "differentiation" as used herein refers to the cellular development of a cell from a primitive stage towards a more mature (i.e. less primitive) cell. The term "directed differentiation" as used herein refers to forcing differentiation of a cell from an undifferentiated (e.g. more primitive cell) to a more mature cell type (i.e. less primitive cell) via non-genetic manipulation. In some embodiments, a stem cell is subject to directed differentiation into a myogenic cell.

The term "pluripotency" or a "pluripotent state" as used herein refers to a cell with the ability to differentiate into all three embryonic germ layers: endoderm (gut tissue), mesoderm (including blood, muscle, and vessels), and ectoderm (such as skin and nerve), and typically has the potential to divide in vitro for a long period of time, e.g., greater than one year or more than 30 passages.

The term "multipotency" refers to a cell with the degree of developmental versatility that is less than totipotent and pluripotent.

The term "totipotency" refers to a cell with the degree of differentiation describing a capacity to make all of the cells in the adult body as well as the extra-embryonic tissues including the placenta. The fertilized egg (zygote) is totipotent as are the early cleaved cells (blastomeres)

The term "differentiated cell" is meant any primary cell that is not, in its native form, pluripotent as that term is defined herein. The term a "differentiated cell" also encompasses cells that are partially differentiated, such as multipotent cells, or cells that are stable non-pluripotent partially reprogrammed cells. It should be noted that placing many primary cells in culture can lead to some loss of fully differentiated characteristics. Thus, simply culturing such cells are included in the term differentiated cells and does not render these cells non-differentiated cells (e.g. undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture. In some embodiments, the term "differentiated cell" also refers to a cell of a more specialized cell type derived from a cell of a less specialized cell type (e.g., from an undifferentiated cell or a reprogrammed cell) where the cell has undergone a cellular differentiation process.

As used herein, the term "somatic cell" refers to any cell other than a germ cell, a cell present in or obtained from a pre-implantation embryo, or a cell resulting from proliferation of such a cell in vitro. Stated another way, a somatic cell refers to any cells forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro.

As used herein, the term "adult cell" refers to a cell found throughout the body after embryonic development.

In the context of cell ontogeny, the term "differentiate", or "differentiating" is a relative term meaning a "differentiated cell" is a cell that has progressed further down the developmental pathway than its precursor cell. Thus in some embodiments, a reprogrammed cell as this term is defined herein, can differentiate to lineage-restricted precursor cells (such as a mesodermal stem cell), which in turn can differentiate into other types of precursor cells further down the pathway (such as an tissue specific precursor, for example, a cardiomyocyte precursor), and then to an end-stage differentiated cell, which plays a characteristic role in a certain tissue type, and may or may not retain the capacity to proliferate further.

The term "phenotype" refers to one or a number of total biological characteristics that define the cell or organism under a particular set of environmental conditions and factors, regardless of the actual genotype.

The term "exogenous" refers to a substance present in a cell other than its native source. The terms "exogenous" when used herein refers to a nucleic acid (e.g. a nucleic acid encoding a sox2 transcription factor) or a protein (e.g., a sox2 polypeptide) that has been introduced by a process involving the hand of man into a biological system such as a cell or organism in which it is not normally found or in which it is found in lower amounts. A substance (e.g. a nucleic acid encoding a sox2 transcription factor, or a protein, e.g., a sox2 polypeptide) will be considered exogenous if it is introduced into a cell or an ancestor of the cell that inherits the substance. In contrast, the term "endogenous" refers to a substance that is native to the biological system or cell (e.g. differentiated cell).

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated".

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched from. In some embodiments, the isolated population is an isolated population of reprogrammed cells which is a substantially pure population of reprogrammed cells as compared to a heterogeneous population of cells comprising reprogrammed cells and cells from which the reprogrammed cells were derived.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a population of reprogrammed cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not reprogrammed cells or their progeny as defined by the terms herein. In some embodiments, the present invention encompasses methods to expand a population of reprogrammed cells, wherein the expanded population of reprogrammed cells is a substantially pure population of reprogrammed cells.

As used herein, the tem "marker" describes the characteristics and/or phenotype of a cell. Markers can be used for selection of cells comprising characteristics of interests. Markers will vary with specific cells. Markers are characteristics, whether morphological, functional or biochemical (enzymatic) characteristics of the cell of a particular cell type, or molecules expressed by the cell type. Preferably, such markers are proteins, and more preferably, possess an epitope for antibodies or other binding molecules available in the art. However, a marker may consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers can be detected by any method available to one of skill in the art. Markers can also be the absence of a morphological characteristic or absence of proteins, lipids etc. Markers can be a combination of a panel of unique characteristics of the presence and absence of polypeptides and other morphological characteristics.

The term "selectable marker" refers to a gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. Proteins whose expression can be readily detected such as a fluorescent or luminescent protein or an enzyme that acts on a substrate to produce a colored, fluorescent, or luminescent substance ("detectable markers") constitute a subset of selectable markers. The presence of a selectable marker linked to expression control elements native to a gene that is normally expressed selectively or exclusively in pluripotent cells makes it possible to identify and select somatic cells that have been reprogrammed to a pluripotent state. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyltransferase (PAC), hygromycin resistance gene (hyg), multidrug resistance gene (mdr), thymidine kinase (TK), hypoxanthine-guanine phosphoribosyl-transferase (HPRT), and hisD gene. Detectable markers include green fluorescent protein (GFP) blue, sapphire, yellow, red, orange, and cyan fluorescent proteins and variants of any of these. Luminescent proteins such as luciferase (e.g., firefly or Renilla luciferase) are also of use. As will be evident to one of skill in the art, the term "selectable marker" as used herein can refer to a gene or to an expression product of the gene, e.g., an encoded protein.

In some embodiments the selectable marker confers a proliferation and/or survival advantage on cells that express it relative to cells that do not express it or that express it at significantly lower levels. Such proliferation and/or survival advantage typically occurs when the cells are maintained under certain conditions, e.g., "selective conditions". To ensure an effective selection, a population of cells can be maintained for a under conditions and for a sufficient period of time such that cells that do not express the marker do not proliferate and/or do not survive and are eliminated from the population or their number is reduced to only a very small fraction of the population. The process of selecting cells that express a marker that confers a proliferation and/or survival advantage by maintaining a population of cells under selective conditions so as to largely or completely eliminate cells that do not express the marker is referred to herein as "positive selection", and the marker is said to be "useful for positive selection". Negative selection and markers useful for negative selection are also of interest in certain of the methods described herein. Expression of such markers confers a proliferation and/or survival disadvantage on cells that express the marker relative to cells that do not express the marker or express it at significantly lower levels (or, considered another way, cells that do not express the marker have a proliferation and/or survival advantage relative to cells that express the marker). Cells that express the marker can therefore be largely or completely eliminated from a population of cells when maintained in selective conditions for a sufficient period of time.

The term "drug screening" as used herein refers to the use of cells and tissues in the laboratory to identify drugs with a specific function. In some embodiments, the present invention provides drug screening on myogenic cells or satellite cells produced by the method disclosed herein to identify compounds or drugs useful as therapies for diseases or illnesses (e.g. human diseases or illnesses).

The term "co-administering," "co-administration," or "co-administer" refers to the administration of two or more compounds to the subject, wherein the two or more compounds can be administered simultaneously, or at different times, as long as they work additively or synergistically. The compounds can be administered in the same formulation or in separate formulations. When administered in separate formulations, the compounds can be administered within any time of each other. For example, the compounds can be administered within 24 hours, 12 hours, 6 hours, 5 hours, 4 hours, 3 hours, 2 hours, 1 hours, 45 minutes, 30 minute, 25 minutes, 20 minutes, 15 minutes, 10 minutes, 5 minutes or less of each other. When administered in separate formulations, any compound can be administered first. Additionally, co-administration does not require the different compounds to be administered by the same route, i.e., the components of the combination can be administered to a subject by the same or different routes of administration. As such, each can be administered independently or as a common dosage form.

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1: A Zebrafish Embryo Culture System Defines Factors that Promote Vertebrate Myogenesis Across Species Ex vivo expansion of satellite cells and directed differentiation of pluripotent cells to mature skeletal muscle have proved difficult challenges for regenerative biology. Using a zebrafish embryo culture system with reporters of early and late skeletal muscle differentiation, we examined the influence of 2,400 chemicals on myogenesis and identified six that expanded muscle progenitors, including three GSKβ inhibitors, two calpain inhibitors and one adenylyl cyclase activator forskolin. Forskolin also enhanced proliferation of mouse satellite cells in culture and maintained their ability to engraft in vivo. A combination of bFGF, forskolin and the GSKβ inhibitor BIO induced skeletal muscle differentiation in human induced pluripotent stem cells (iPSCs) and produced engraftable myogenic progenitors that contributed to muscle repair in vivo. Definition of these approaches to expand satellite cells and differentiate iPSCs to muscle without genetic manipulation provides new insights into skeletal muscle biology and may lead to novel therapies for metabolic and neuromuscular diseases.

In this study, we have taken an interdisciplinary, cross-systems approach to identify evolutionarily conserved molecular pathways that regulate muscle specification and satellite cell expansion in three different vertebrate systems. Capitalizing on the powerful chemical genetics approaches available in the zebrafish, we first performed a high-throughput image-based chemical screen using zebrafish blastomere cells and identified 29 compounds that perturbed muscle development and six that promoted myogenesis. We then tested the muscle promoting compounds against mouse muscle satellite cells and human iPSCs to identify conserved activities. Forskolin, an adenylyl cyclase activator, significantly increased satellite cell proliferation in culture, with the majority of expanded cells retaining phenotypic and functional characteristics of freshly isolated satellite cells, including the capacity to regenerate dystrophic muscle upon transplantation. In addition, a combination of bFGF, the GSKβ inhibitor BIO and forskolin drove skeletal muscle specification of human iPSCs including spontaneous differentiation to mature myofibers and the production of myogenic progenitors that could engraft and contribute to mature muscle fibers when transplanted into immune-compromised recipient mice. Our studies using a zebrafish embryo culture system elucidated a combination of chemicals that promotes muscle development in fish, mouse and human cell populations. This work provides a novel and tractable system to generate and expand mammalian muscle stem cells for functional studies of normal muscle development and therapeutics development for musculoskeletal diseases.

Materials and Methods

Zebrafish Care and Transgenic Lines:

The myf5-GFP; mylz2-mCherry double transgenic line was bred and maintained using standard zebrafish husbandry (Westerfield, 1995). All zebrafish experiments and procedures were performed as approved by the Children's Hospital Boston Institutional Animal Care and Use Committee.

Culture of Disassociated Blastomere Cells:

Disassociated blastomere cells were grown in zESC medium, which is composed of 70% LDF medium and 30% RTS34st-conditioned medium. The LDF medium contains 50% Leibowitz's L-15 (Invitrogen), 35% DMEM (Invitrogen), and 15% Ham's F-12 (Invitrogen), supplemented with 0.18 g/l sodium bicarbonate, 15 mM HEPES (Invitrogen), 1% L-Glutamine (Invitrogen), 10 μg/ml ciprofloxacin (Sigma-Aldrich), 100 μg/ml piperacillin (Sigma-Aldrich), 10 μg/ml amphotericin B (Sigma-Aldrich), 10 nM sodium selenite (Sigma-Aldrich), 1% N2 (Invitrogen), and 2% B27 (Invitrogen). The RTS34st conditioned medium was prepared by incubating fresh medium (Leibowitz's L-15 plus 15% FBS) on a confluent culture of RTS34st cells for 3 days.

High-Throughput Screen:

Four 384-well plates were coated with 0.1% gelatin. Chemicals from the CHB library were diluted 150 times with zESC medium containing 1 ng/ml bFGF and were aliquoted 30 μl per well. Males and females of the myf5-GFP; mylz2-mCherry transgenic line were set up overnight and kept separated until morning when they were mixed for mate. Approximately 800 oblong-stage embryos were washed three times with E3 embryo water and were treated with pronase to remove chorions. Dechorionated embryos were washed with E3 embryo water three times and collected into a 50 ml falcon tube with 25 ml zESC medium containing 1 ng/ml bFGF. Embryos were disassociated by shaking approximately 20 times and were filtered through a 70 μm nylon mesh filter. The resulting single cells were diluted to 60 ml with zESC medium containing 1 ng/ml bFGF and aliquoted 30 μl per well into the four 384-well plates with pre-added chemicals. The cells were cultured in a 28-degree incubator without $CO_2$. Cells were imaged by a Celigo cytometer (Cyntellect) under channels of GFP, mCherry, and transmitted light. The images were analyzed by the built-in software and confirmed eye.

Whole-Mount In Situ Hybridization:

Whole mount in situ hybridizations were performed as previously described (Belting et al., 2001).

SMP Isolation and Culture:

SMP isolation was performed as previously described (Cerletti et al., 2008; Sherwood et al., 2004). Briefly, MFA cells were prepared from intact skeletal muscles (EDL, gastrocnemius, quadriceps, soleus, TA, triceps brachii, abdominal) by digesting the muscles with collagenase type II and then dispase enzymes. MFA cells were stained for isolation of $CD45^-Sca-1^-Mac-1^-CXCR4^+$ b1-integrin$^+$ cell population by FACS. For in vitro expansion experiments, SMPs were seeded on collagen/laminin-coated plates in F10 (Gibco) containing 20% horse serum (Atlanta Biologics), 1% penicillin-streptomycin (Invitrogen) and 1% glutamax (Invitrogen). In experiments that cells were treated with bFGF, 5 ng/ml bFGF (Sigma) was added to the medium daily. 50 μM forskolin (Santa Cruz) or 0.1% DMSO was added to the wells 24 hours after plating, medium was changed with fresh medium containing the compound 48 hour after plating and the treatment continued for 36 more hours, after which medium was changed with fresh medium without the compound. Cells were counted or used for transplantation after 5 days in culture. For Myogenic colony formation assay cells were fixed and counted after 6 days in culture. For the differentiation experiments cells were cultured for 5 days with or without compound treatment, on day 5 cells were harvested and equal numbers of cells (8,000 cells) were re-plated in each well of a 96-well plate in growth medium. Medium was changed to DMEM (gibco), containing 2% horse serum (Atlanta Biologics), 1% penicillin-streptomycin (Invitrogen) and with or without 50 μM Forskolin or 0.1% DMSO after 4 hours. Cells were fixed after 60 hours in differentiation medium.

Immunofluorescence and Imaging:

Cultured SMPs were fixed in 4% paraformaldehyde (PFA) and stained with 10 μg/ml Hoechst (Invitrogen). Pictures from the whole well were taken using Celigo cytometer (Cyntellect) under the UV channel. The images were analyzed and numbers of cells were counted by the built-in software. Differentiated cells were stained for myosin heavy chain (Primary antibody: anti-skeletal myosin type II (fast-twitch) 1:200 and anti-skeletal myosin type I (slow-twitch) 1:100, Sigma. Secondary: goat anti-mouse IgG Alexa-555 conjugate (Molecular Probes) 1:250) and 10 μg/ml Hoechst (Invitrogen) and pictures from the whole well were taken using Celigo cytometer (Cyntellect) under UV and red channels. The images were analyzed and percentage of nuclei in myotubes was calculated using a modified ImageJ macro developed in-house. Sections of the transplanted muscles were stained for GFP (rabbit anti-GFP Alexa 488 conjugate (Invitrogen) 1:250) and for dystrophin (Primary: rabbit anti-dystrophin (Abcam) 1:50. Secondary: goat anti-rabbit IgG Alexa-555 conjugate (Molecular probes) 1:250) and imaged using an upright Zesis fluorescent microscope.

cAMP Assay:

cAMP assay was performed using the cAMP-Glo™ Assay kit (Promega) according to the manufacturer's protocol.

Flow Cytometry:

Flow cytometry analysis was performed using a BD LSR II, provided through the Harvard Stem Cell Institute Flow Cytometry Core Facility. Flow cytometry data were collected using DIVA (Becton Dickinson (BD), Franklin Lakes, N.J.) software and analyzed offline using Flowjo software (Tree Star, Inc., Macintosh version 8.1.1, Ashland, Oreg.). Antibodies used for flow cytometry included: APC/Cy7 anti-mouse Ter119, clone Ter119 (1:200, Biolegend 116223), APC/Cy7 anti-mouse CD45, clone 30-F11 (1:200, Biolegend 103116), APC/Cy7 anti-mouse CD11b, clone M1/70 (1:200, Biolegend 101226), APC Anti-mouse Ly-6A/E (Sca-1), clone D7 (1:200, Biolegend 108112), Biotin anti-mouse CD184 (CXCR4, Fusin) (1:100, BD Biosciences 551968), Streptavidin PE-Cy7 (1:100, eBioscience 25-4317-82), PE anti-mouse/rat CD29 Antibody (1:100, Biolegend 102208). Live cells were identified by positive staining with calcein blue (1:1000) (Invitrogen, Carlsbad, Calif.) and negative staining for propidium iodide (PI, 1 µg/mL). Antibody incubations were performed in staining medium (SM=Hank's Buffered Saline Solution (HBSS, (Gibco))+2% donor horse serum), on ice for 15 min.

Tissue Injury and Mouse Satellite Cell Transplantation:

mdx mice were anesthetized and 25 µl (0.03 mg/ml) of Naja mossambica mossambica cardiotoxin (Sigma) was injected in their TA muscle 1 day before cell transplantation. The next day, 6,000 freshly isolated double-sorted GFP+ SMPs or total number of cells expanded from 6,000 SMPs after 5 days in culture and compound treatment, were injected directly into these pre-injured muscles in 20 µl PBS. The contralateral TA was injected with PBS only as the negative control. 3-4 weeks after transplantation, transplanted muscles were harvested and analyzed by cryosectioning and microscopy.

Human iPSCs Lines Generation and Maintenance:

BJ iPSCs were obtained from Chad Cowan (Harvard Stem Cell Institute, Cambridge, Mass.), 05400 and 00409 human iPSCs lines were generated from adult skin fibroblasts by retroviral transduction of KLF4, SOX2, OCT4 and c-MYC reprogramming factors as previously described (Takahashi et al. 2007, Park et al. 2008). Pluripotency was assessed by morphology, immunestaining for NANOG, OCT4, SSEA3-4 and Tra1-60, gene expression of NANOG, OCT4, SOX2, REX1, TERT, DNm3b pluripotency genes and EB formation. iPSCs were grown on matrigel-coated dishes (BD) and maintained in mTeSR1 medium (STEMCELL technologies).

Skeletal Muscle Differentiation of iPSCs:

Cells were differentiated by generating EBs in suspension culture 7 days and then transferred to matrigel-coated plates for additional 29 days. During the suspension culture the cells received the differentiation medium STEMDiff Apel medium (STEMCELL technologies) supplied with 10 ng/ml bFGF (Invitrogen), 0.5 µM BIO (Santa Cruz Biotechnologies) and 20 µM forskolin (Santa Cruz Biotechnologies). Two-three days after plating EBs, the medium was switched to DMEM complemented with 2% horse serum for the remaining differentiation.

Gene Expression Analysis:

Total RNA was extracted from iPSCs using RNeasy Mini kits (Qiagen, Mississagua, ON). RNA (1 µg) was reverse-transcribed using a high-capacity reverse transcription kit (Applied Biosystems) according to the manufacturer's instructions. Real-time PCR was performed using the SYBR green PCR master mix (Bio-Rad). Fluorescence was detected by a multicolor real-time detection system (Cycler IQ; Bio-Rad). All reactions were performed in duplicate and GAPDH was used as a housekeeping control. Primers used in the study are shown in Table 3:

TABLE 3

Primers used in this study.

| Gene | Location | SEQ ID NO: | Sequence (5' → 3') |
|---|---|---|---|
| NCAM | Primer Forward | 1 | ATGGAAACTCTATTAAAGTGAACCTG |
|  | Primer Reverse | 2 | TAGACCTCATACTCAGCATTCCAGT |
| PAX6 | Primer Forward | 3 | TCTAATCGAAGGGCCAAATG |
|  | Primer Reverse | 4 | TGTGAGGGCTGTGTCTGTTC |
| AFP | Primer Forward | 5 | AGCTTGGTGGTGGATGAAAC |
|  | Primer Reverse | 6 | CCCTCTTCAGCAAAGCAGAC |
| GATA4 | Primer Forward | 7 | CTAGACCGTGGGTTTTGCAT |
|  | Primer Reverse | 8 | TGGGTTAAGTGCCCCTGTAG |
| FLK1 | Primer Forward | 9 | AGTGATCGGAAATGACACTGGA |
|  | Primer Reverse | 10 | GCACAAAGTGACACGTTGAGAT |
| GATA2 | Primer Forward | 11 | GCAACCCCTACTATGCCAACC |
|  | Primer Reverse | 12 | CAGTGGCGTCTTGGAGAAG |
| VECAD | Primer Forward | 13 | CAGCCCAAAGTGTGTGAGAA |
|  | Primer Reverse | 14 | TGTGATGTTGGCCGTGTTAT |
| GAPDH | Primer Forward | 15 | TGGTATCGTGGAAGGACTCA |
|  | Primer Reverse | 16 | TTCAGCTCAGGGATGACCTT |
| PAX7 | Primer Forward | 17 | CGTGCTCAGAATCAAGTTCG |
|  | Primer Reverse | 18 | GTCAGGTTCCGACTCCACAT |
| MYF5 | Primer Forward | 19 | GCCTGAAGAAGGTCAACCAG |
|  | Primer Reverse | 20 | CCATCAGAGCAGTTGGAGGT |
| MYOD1 | Primer Forward | 21 | TGCCACAACGGACGACTT |
|  | Primer Reverse | 22 | CGGGTCCAGGCTTCGAA |
| Myogenin | Primer Forward | 23 | AGATGTGTCTGTGGCCTTCC |
|  | Primer Reverse | 24 | AGCTGGCTTCCTAGCATCAG |
| MYHC | Primer Forward | 25 | TTCATTGGGGTCTTGGACAT |
|  | Primer Reverse | 26 | AACGTCCACTCAATGCCTTC |
| DNMT3B | Primer Forward | 27 | ATAAGTCGAAGGTGCGTCGT |
|  | Primer Reverse | 28 | GGCAACATCTGAAGCCATTT |

TABLE 3-continued

Primers used in this study.

| Gene | Location | SEQ ID NO: | Sequence (5' → 3') |
|---|---|---|---|
| HTERT | Primer Forward | 29 | TGTGCACCAACATCTACAAG |
|  | Primer Reverse | 30 | GCGTTCTTGGCTTTCAGGAT |
| NANOG | Primer Forward | 31 | TCCAACATCCTGAACCTCAG |
|  | Primer Reverse | 32 | GACTGGATGTTCTGGGTCTG |
| OCT4 | Primer Forward | 33 | GTGGAGGAAGCTGACAACAA |
|  | Primer Reverse | 34 | CAGGTTTTCTTTCCCTAGCT |
| REXI | Primer Forward | 35 | TGGACACGTCTGTGCTCTTC |
|  | Primer Reverse | 36 | GTCTTGGCGTCTTCTCGAAC |
| SOX2 | Primer Forward | 37 | TTGTCGGAGACGGAGAAGCG |
|  | Primer Reverse | 38 | TTGTCGGAGACGGAGAAGCG |

Immunofluorescence:

iPSCs were fixed in 4% paraformaldehyde and permeabilized for 15 min with PBS containing 0.1% Triton. Cells were then blocked for 1 hour with PBS containing 5% bovine serum albumin (BSA) and incubated overnight at 4° C. with anti-Desmin (Dako), -Myogenin, -MYOD1 (Santa Cruz Biotechnologies), and -PAX7 (DSHB, university of Iowa) primary antibodies. Alexa488- and Alexa594-conjugated secondary antibodies (Invitrogen) were used for detection as appropriate.

Transplantation Studies of iPSC-Derived Muscle Progenitors:

For the in vivo study of transplantation, 5-6 week old NSG mice from Jackson Laboratories (stock number 002378) were used. One day before intramuscular cell transplantation, TA muscle were pre-injured with 0.3 mg/ml cardiotoxin. After 24 hours, myogenic progenitors (1×10$^5$ cells/25 µl PBS) were injected into the left TA muscle, whereas the right leg of each mouse received the same amount of PBS, as a negative control. One month after transplantation, mice were sacrificed and muscles were harvested and frozen in iso-pentane cooled in liquid nitrogen. Serial cryosections were fixed with 4% PFA and stained with anti-δ-Sarcoglycan antibodies (Leica).

Electron Microscopy and Immune-Gold Staining:

For electron microscopy, samples were fixed in a solution of 2.5% glutaraldehyde in a 0.1 M phosphate buffer for 3 hours at room temperature, washed several times with a 0.1 M phosphate buffer and then post-fixed with a solution of 2% osmium tetroxide in a 0.1 M phosphate buffer at room temperature for one hour. Subsequently, samples were dehydrated and embedded in araldite resin blocks and sectioned at 80 nanometers using an LKB Nova ultra-microtome with a diatome diamond knife. The grids were stained with uranyl acetate and reynolds lead citrate before being observed on the Philips EM-301 Transmission Electron Microscope.

For electron immune-gold staining, sample were fixed in 2% paraformaldehyde, 1% glutaraldehyde, in a 0.1M phosphate buffer for 3 hours at room temperature, washed and directly embedded in araldite resin blocks. Section of 80 nanometers were stained with primary anti-skeletal myosin heavy and light chain antibodies (AbCam) followed by a gold-conjugated secondary antibody. The samples were then stained with uranyl acetate and lead citrate for contrast and then observed in the Philips 301 Transmission Electron Microscope.

Results

A Zebrafish Embryo Culture System to Examine Skeletal Muscle Development:

To develop a platform for screening for factors involved in myogenic specification, we sought to establish fluorescent "reporter fish" in which different developmental states of skeletal myogenesis could be distinguished. During zebrafish gastrulation, mesoderm progenitors undergo involution and convergence extension movements and begin myogenesis. Myogenic commitment is signified by expression of myoD and myf5 (Weinberg et al., 1996), which are functionally redundant and exhibit overlapping expression in the earliest myogenic precursors (Hinits et al., 2009). Terminal differentiation of these progenitors produces cells expressing genes encoding muscle-specific structural proteins like myosin light polypeptide 2 (mylz2), found in fast skeletal muscle (Ju et al., 2003). To label different developmental states of skeletal muscle cells in zebrafish embryos, we generated a myf5-GFP; mylz2-mCherry double transgenic zebrafish line. At the 11-somite stage, myf5-GFP expression was restricted to the newly formed somite, while no mylz2-mCherry expression was detected (FIG. 1A). Expression of mylz2-mCherry was first detected at 30 hours post fertilization (hpf) in the anterior somites and later spread to the posterior somites (FIG. 1A). These data indicate that expression of myf5-GFP and mylz2-mCherry recapitulate the expression patterns of their corresponding endogenous genes (Thisse et al., 2001), and thus provide a useful surrogate to track myogenic specification and progression during embryonic development. To test whether zebrafish blastomere cells could form muscle in vitro, we disassociated myf5-GFP; mylz2-mCherry embryos at the oblong stage and plated them on gelatin-coated dishes. When cells were cultured in zebrafish ESC (zESC) medium (Fan and Collodi, 2006), 1-10% became GFP-positive, indicating upregulation of myf5 expression. Among the GFP-positive cells, 1-5% were also mCherry (mylz2) positive, suggesting that myogenic specification and differentiation had occurred in our in vitro system (FIG. 1B).

Figure 8:
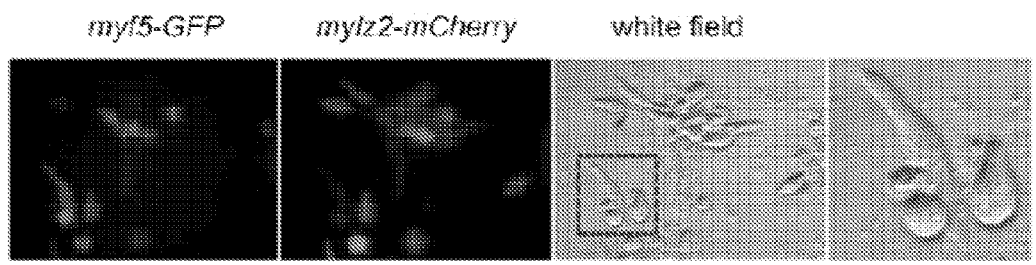
FIGS. 8A-8C show that myogenesis suppressors identified in vitro also affect muscle development in vivo (related to FIG. 1).
Figure 8:
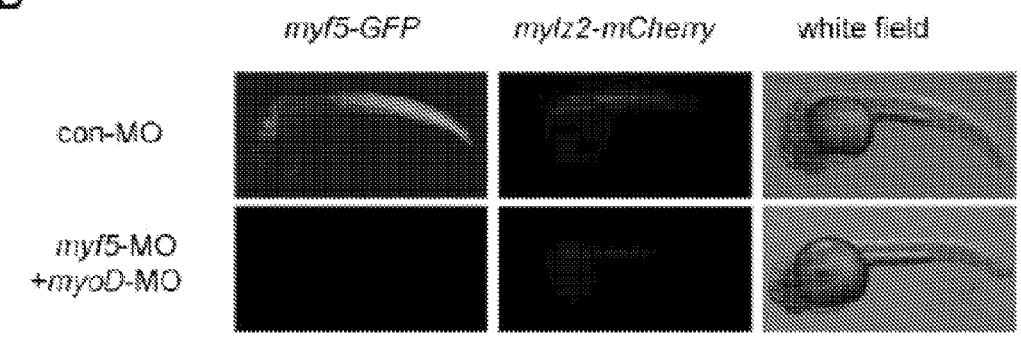
Figure 8:
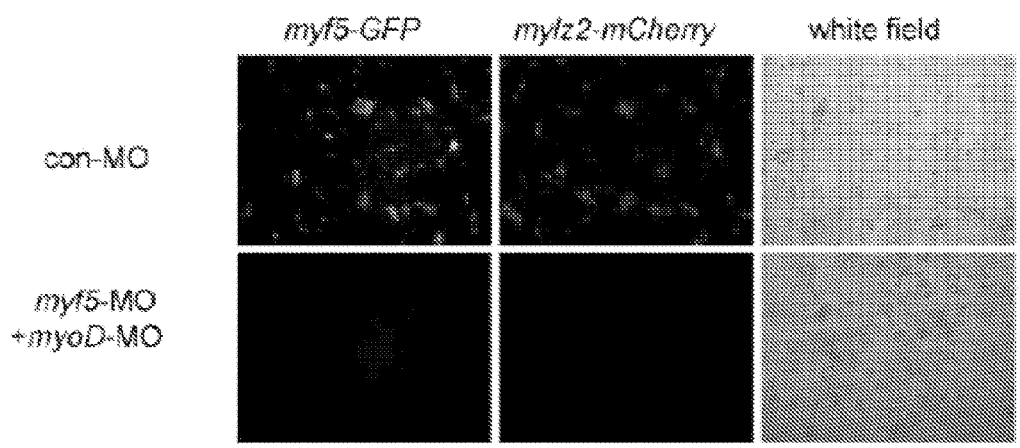

FGF signaling appears to be required for muscle development in early zebrafish embryos, as myogenesis is essentially blocked in fgf24 and fgf8 double deficient embryos (Draper et al., 2003). FGF signals directly activate myoD expression in Xenopus (Fisher et al., 2002) and are important for fast skeletal muscle induction (Groves et al., 2005). Based on these data, we added bFGF to the embryo cultures and found that the majority of cells became GFP and mCherry double positive, indicating a potent muscle-promoting effect (FIGS. 1B and 8A). Other myogenic genes, including myoD, mrf4, and myog, were also highly expressed by blastomere cells cultured with bFGF (FIG. 1C). To confirm that the in vitro generated cells labeled by GFP and mCherry corresponded to the expected stages of muscle development, we isolated each population by fluorescence-activated cell sorting (FACS) and analyzed its gene expression. Compared to the GFP/mCherry double negative population, both myf5-GFP+; mylz2-mCherry- and double positive populations were enriched for myogenic gene expression and exhibited lower expression of blood (embryonic globin) and liver (ifabp) genes. Double positive cells also expressed higher levels of myoD and mylz2 than the myf5-GFP+; mylz2-mCherry-population, suggesting that, similar to the in vivo situation (FIG. 1A), myf5-GFP and mylz2-mCherry faithfully label stage-specific myogenic populations within these in vitro cultures (FIG. 1D).

To further validate this in vitro myogenesis system, we next determined whether genes required for muscle development in vivo were also required in culture. Zebrafish embryos injected with myf5 and myoD double morpholinos are immobile, presumably due to defective muscle development (Schnapp et al., 2009). Expression of key myogenic regulatory factors (mrfs), like myogenin and mrf4, and genes encoding structural proteins, like myosin heavy chain (mhc) and mylz2, are absent in the double morphant (Schnapp et al., 2009). Consistent with these prior observations, embryos injected with double morpholinos lack myf5-GFP and mylz2-mCherry expression at 30 hpf (FIG. 8B). In addition, cultured blastomere cells from the double morphant showed dramatically decreased expression of myf5-GFP and mylz2-mCherry, indicating that Myf5 and MyoD are likewise essential for muscle development in vitro as well (FIG. 8C). The embryonic myogensis program appears to be conserved during in vitro differentiation of zebrafish blastomeres.

A Chemical Genetic Screen Identifies Modifiers of Skeletal Muscle Development:

To evaluate the sensitivity of the embryo culture system to a modifier screen, we treated cells in FGF with all-trans retinoic acid (ATRA). ATRA was previously added to murine ESC culture to promote neural lineage differentiation (Lu et al., 2009), and ATRA treatment inhibits posterior mesoderm formation in zebrafish (de Jong et al., 2010). Consistent with these prior studies, ATRA treatment blocked skeletal muscle development in cultures of zebrafish blastomere cells (FIG. 1E).

Figure 2:
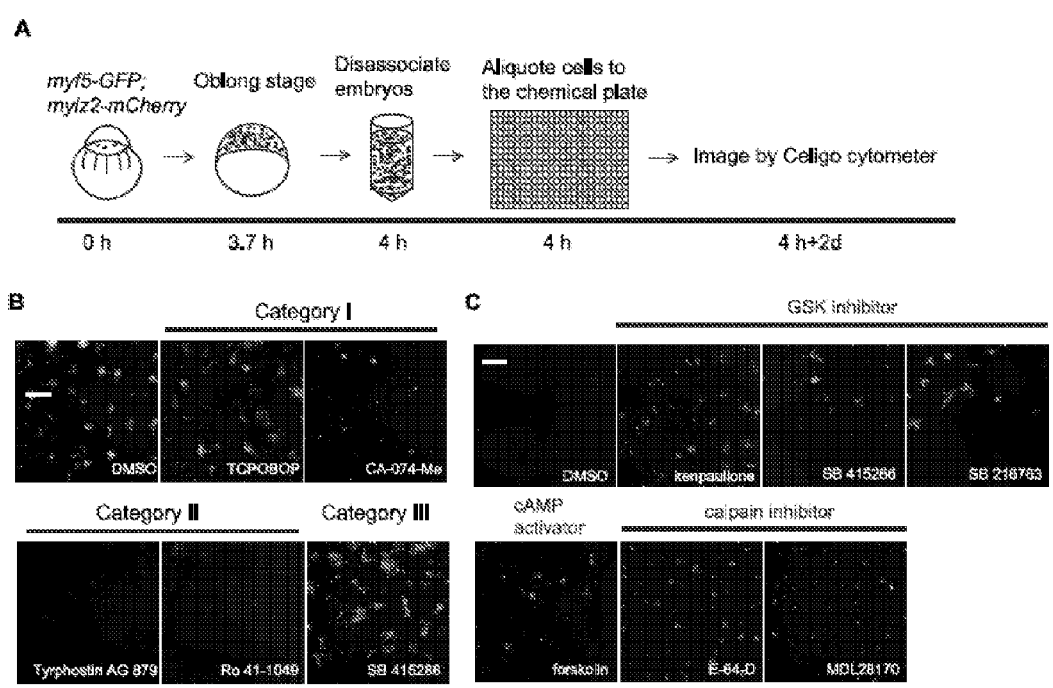
FIGS. 2A-2C show the chemical genetic screens to identify modifiers of skeletal muscle development.

To enable a higher throughput analysis of candidate modifiers of skeletal myogenesis, the embryo culture system was adapted to a semi-automated chemical screening platform. myf5-GFP; mylz2-mCherry embryos were collected from double transgenic parents and disassociated at the oblong stage. The resulting individual blastomere cells were aliquoted into four 384-well plates with pre-added chemicals, and culture medium was supplemented with bFGF to promote muscle development. After one day, the cells were automatically imaged and analyzed using a Celigo cytometer for GFP, mCherry, and bright-field signals, and image analysis was confirmed by visual inspection (FIG. 2A).

We screened 2,400 chemicals and identified 29 that perturbed the GFP or mCherry signals with undetectable toxicity. Based on the changes of GFP (Myf5) and mCherry (Mylz2) signals, these 29 hits could be divided into three categories. Category I compounds produced cultures with only myf5-GFP-positive cells, a phenotype likely caused by blocking differentiation of muscle progenitors into mature muscle cells (FIG. 2B and Table 1). Eleven chemicals, including inhibitors of the p38 pathway, which previously was shown to be required for muscle formation (Cuenda and Cohen, 1999; Wu et al., 2000; Zetser et al., 1999), fell into this category. Category II included 17 chemicals, and resulted in fewer cells expressing either fluorescent color, likely because these chemicals block commitment of mesoderm progenitors to the muscle progenitor fate (FIG. 2B and Table 2). Category III held only one compound (SB415286, a GSKβ inhibitor), which induced increased expression of both markers, presumably by accelerating muscle development (FIG. 2B).

TABLE 1

Exemplary chemicals and their targeting pathway that block mature muscle differentiation.

| Chemical | Pathway |
| --- | --- |
| CHIR 99021 | GSK inhibitor |
| Purmorphamine | Hedgehog Activator |
| TMB-8 | ion channel or pump |
| Propafenone | K+ channel or pump |
| Ouabain | K+ channel or pump |
| TCPOBOP | Nuclear Receptor Ligand |
| Ouabain | other |
| CA-o74-Me | Protease Inhibitor |
| SB 202190 | p38 inhibitor |
| LY-3 67265 | Serotonin |

Table 1 lists chemicals that are identified specifically by their reduction of mylz2-mCherry expression. The phenotype is presumptively due to the blocking of muscle progenitor differentiation. We used a chemical library with biologically known chemicals. The pathway that a chemical targets is listed on the right.

TABLE 2

Chemicals and their targeting pathway that block skeletal muscle progenitor formation.

| Chemical Name | Pathway | myoD expression |
| --- | --- | --- |
| (-)-Scopolamine, n-Butyl-, bromide | acetylcholine | Level 1 |
| Miberfradil dihydrochloride | $Ca^{2+}$ channel or pump | Level 2 |
| Methotrexate | Cell cycle | No change |
| Ro 41-1049 hydrochloride | COMT/MAO | Level 4 |
| (±)-6-Chloro-PB hydrochloride | dopamine | Level 1 |
| Spermidine trihydrochloride | glutamate | Level 1 |
| Tyrphostin AG 527 | HER/EGF-R Inhibitor | No Change |
| Tyrphostin AG 527 | HER/EGF-R Inhibitor | Level 1 |
| Tyrphostin AG 879 | HER2R/Trka inhibitor | Toxic |
| Geldanamycin | Hsp90 inhibitor | No change |
| ATRA | Nuclear Receptor Ligand | Level 4 |
| 1-Acyl-PAF | PAF | Level 3 |
| LY-294,002 hydrochloride | PI3K/mTOR inhibitor | Level 2 |
| Rapamycin | PI3K/mTOR inhibitor | Level 2 |
| SB-431542 | TGFbR/ALKR inhibitor | No change |
| Helenalin | TNFa/IKK/NFkB | Toxic |
| Tyrphosfin AG 808 | tyrosine kinase | Level 1 |

Figure 9:
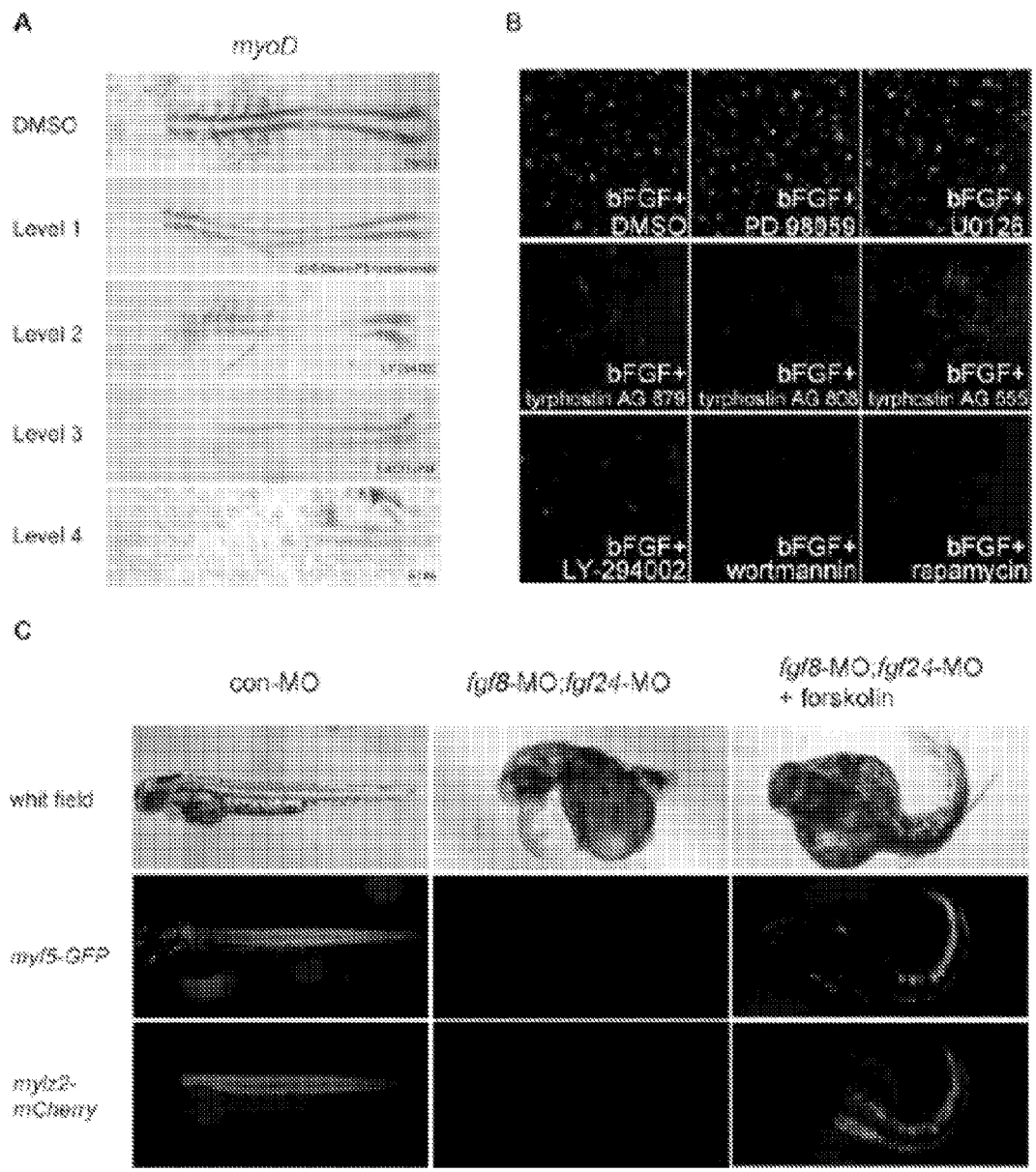
FIGS. 9A-9C show the chemical genetics screens to identify modifiers of skeletal muscle development (related to FIG. 2) FIG. 9A, Embryos were treated with hits at the sphere stage. Once the control embryos reached the 6-somite stage, they were collected for whole-mount in situ hybridization with the myoD riboprobe. Examples of hits verified to perturb muscle development in vivo. Flat mounted embryos stained with the myoD riboprobe at the 6-somite stage are shown with anterior to the left. Embryos were treated with (±)-6-Chloro-PB hydrobromide, LY-294002, 1-ACYL-PAF, or ATRA. All chemicals were from the CHB library and were diluted 300-fold. The level of myoD reduction was determined by comparing the intensity of myoD expression in these embryos with that in control embryos treated with DMSO.

Table 2 lists chemicals that are identified by their reduction of both myf5-GFP and mylz2-mCherrz expression. This phenotype is presumptively due to the blocking of skeletal muscle progenitor formation. We used a chemical library with biologically known chemicals. The pathway that a chemical targets is listed in the middle. To test if the hits function in vivo, developing embryos were treated with individual chemicals and assayed for myoD expression. Two thirds of the hits showed decreased myoD staining at different levels, which are indicated in FIG. 9A. The staining results are listed in the third column.

To test whether these chemicals might also modulate myogenesis in vivo, we treated zebrafish embryos with each of the Category II chemicals, which blocked myogenesis in vitro, and evaluated the effect on expression of myoD at the 6-somite stage. Among the 17 compounds tested, 11 caused decreased myoD expression in vivo. Two chemicals induced non-specific toxicity and four produced no apparent effect (FIG. 9A and Table 2). Thus, 65% of the hits identified in our initial in vitro screen also perturbed muscle development in vivo, suggesting that the in vitro screening system is valid and effective for revealing muscle biology in vivo.

bFGF induces muscle development by activating the FGF receptor tyrosine kinase. In support of this concept, we identified three receptor tyrosine kinase (RTK) inhibitors that block the muscle-promoting effect of bFGF (FIG. 9B). bFGF activates several intracellular pathways, including those involving MEK/ERK and phosphoinositide-3-kinase (PI3K)-AKT signaling. No MEK/ERK inhibitor was found to inhibit muscle development (FIG. 9B). In contrast, the muscle-promoting effect of bFGF could be blocked completely by the PI3K inhibitor LY-294002 (FIG. 9B). Another PI3K inhibitor, wortmannin, had a similar effect (FIG. 9B). Treatment with rapamycin, an mTOR inhibitor, also blocked muscle development induced by bFGF (FIG. 9B). These results suggest that bFGF promotes myogenesis through the PI3K-mTOR signaling pathway, rather than the MEK/ERK pathway.

A Sensitized Chemical Genetic Screen Identifies Enhancers of Skeletal Muscle Development:

The strong muscle promoting effect of bFGF made it difficult to identify enhancers of skeletal muscle development in our original system. Only one out of 2,400 chemicals was identified to promote muscle development. To sensitize the system for identifying enhancers of skeletal muscle development, we repeated the screen in the absence of bFGF. In this sensitized screen, six chemicals out of 2,400 were identified to increase the GFP and mCherry signals (FIG. 2C). Among the six hits were three GSKβ inhibitor (kenpaullone, SB415286, and SB216763), two calpain inhibitors (E-64-D and MDL28170) and one cAMP activator forskolin.

To examine the ability of these chemicals to induce myogenesis in vivo, embryos were incubated with each of the chemicals and the impact on myoD expression was assessed. None of the six chemicals increased myoD expression in wild-type embryos, presumably due to a masking effect by the strong endogenous muscle development program (data not shown). We next evaluated the interaction of these chemicals with the FGF pathway. Embryos were injected with morpholinos targeted to fgf8 and fgf24, which led to a defect in myogenesis as previously reported (Draper et al., 2003), and each chemical was added to the double fgf8; fgf24 morphant to evaluate its ability to rescue myogenesis. Of the six compounds tested, only forskolin rescued the myogenesis defect, indicating a unique activity of forskolin compared to the other compounds (FIG. 9C).

Figure 3:
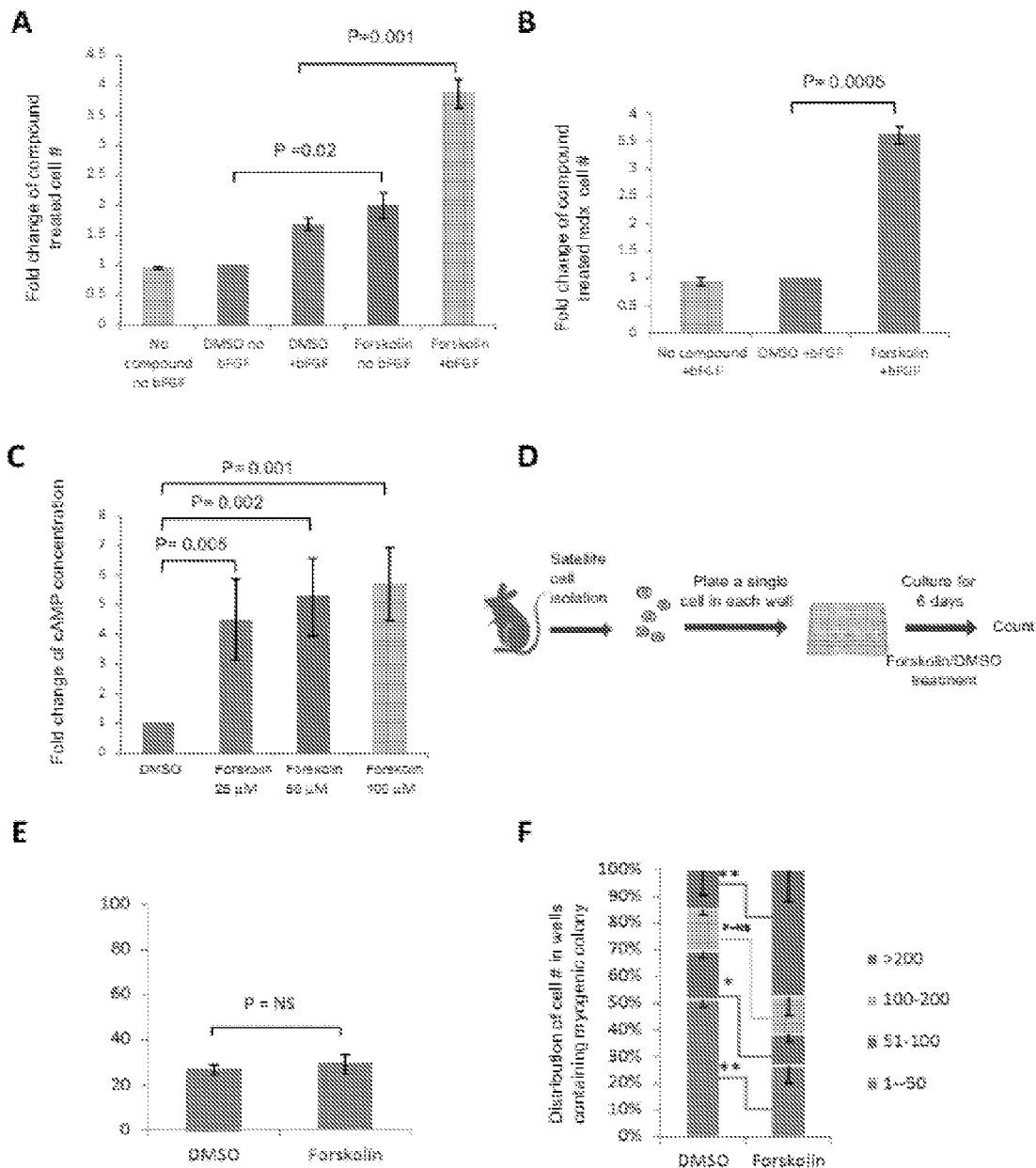
FIGS. 3A-3F show that forskolin treatment elevates cAMP level and increases proliferation of satellite cells from both healthy and dystrophic mice.
Figure 10:
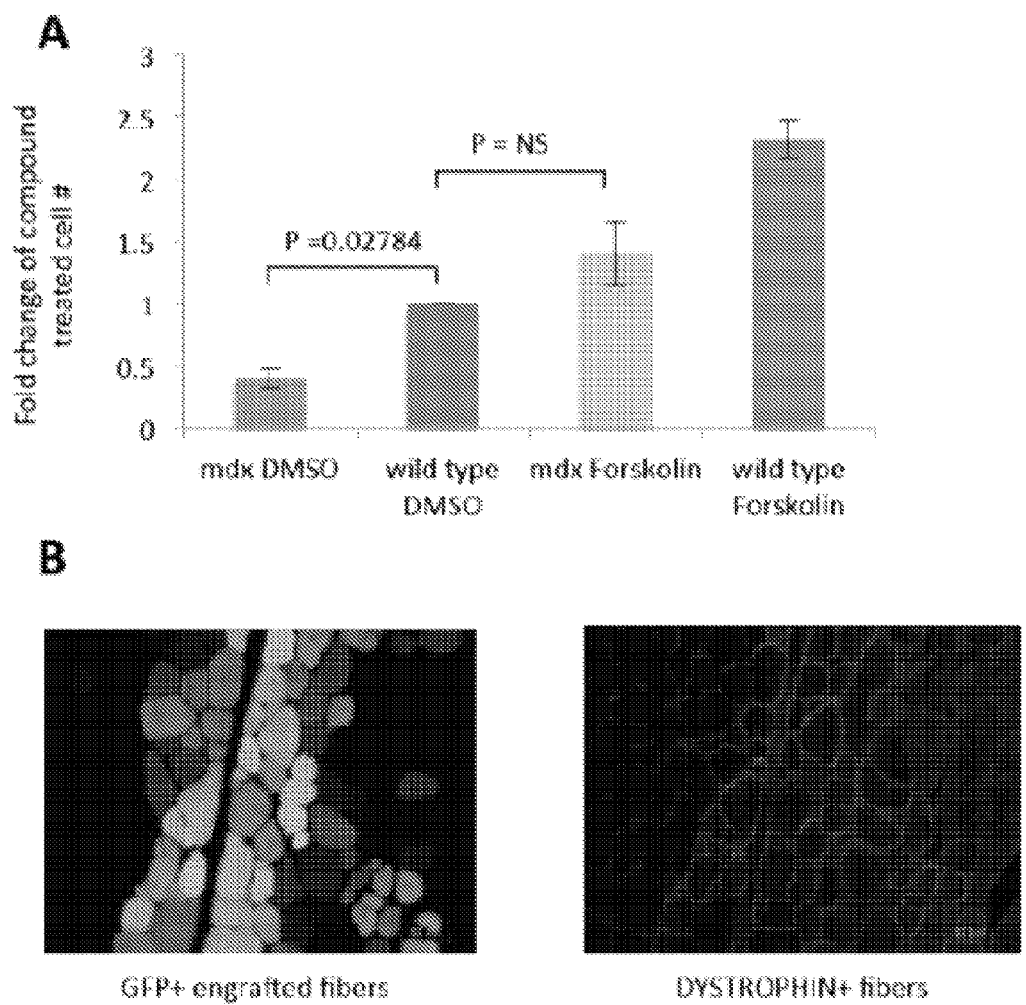
FIGS. 10A and 10B show that forskolin treatment restores proliferation of mdx satellite cells and transplant of forskolin-treated satellite cells restores Dystrophin expression to dystrophic mdx muscle (related to FIG. 3).

Forskolin Treatment Elevates cAMP Levels and Expands Mouse Satellite Cells in Vitro:

We hypothesized that the chemical hits enhancing skeletal muscle development in zebrafish blastomeres may likewise promote muscle precursor cell formation and/or expansion in other species. To test this hypothesis, we first tested the effects of these compounds on satellite cells purified from adult mouse skeletal muscle. Mouse satellite cells were isolated by FACS, as described in (Cerletti et al., 2008; Sherwood et al., 2004) and seeded into culture in the presence of different concentrations of each of the (Cerletti et al., 2008; Sherwood et al., 2004) myogenesis promoting chemicals. Cell number in the resulting colonies was determined after 5 days in culture. Of the six chemicals tested, only forskolin triggered dose-dependent expansion of mouse satellite cell cultures (data not shown). The number of cells in these cultures was significantly increased by forskolin treatment both in the presence and absence of bFGF (FIG. 3A). Forskolin treatment also increased cell number in satellite cell cultures seeded from mdx mice, a mouse model of Duchenne muscular dystrophy (DMD) (Sicinski et al., 1989). Satellite cells from mdx mice typically exhibit defective ex vivo expansion under control conditions, and forskolin treatment restored their proliferation to levels seen normally in cultures of untreated wild-type satellite cells (FIGS. 3B and 10A).

To evaluate the mechanism by which forskolin drives increased cell number in satellite cell cultures, we assayed cAMP production and performed cell survival and proliferation assays in forskolin-treated cultures. Consistent with forskolin's known role as an activator of adenylate cyclase (Metzger and Lindner, 1981; Seamon et al., 1981), forskolin treatment induced a dose dependent increase in cAMP levels in mouse satellite cell cultures (FIG. 3C). To test forskolin's effect on satellite cell survival and proliferation, single cells were plated at one cell per well in 96-well plates and treated with forskolin or DMSO. After six days in vitro culture, we quantified the number of wells containing any number of myogenic cells (a measure of cell survival) and the number of cells in those wells (a measure of cell proliferation) (FIG. 3D). The frequency of myogenic colony formation did not differ between forskolin and DMSO treated cells (FIG. 3E), indicating that forskolin treatment does not affect cell survival. Consistent with previous observations (FIG. 3A), myogenic colonies formed in the presence of forskolin contained more cells as compared to DMSO treated cells (FIG. 3F), most likely reflecting an effect of the compound on myogenic cell proliferation.

Figure 4:
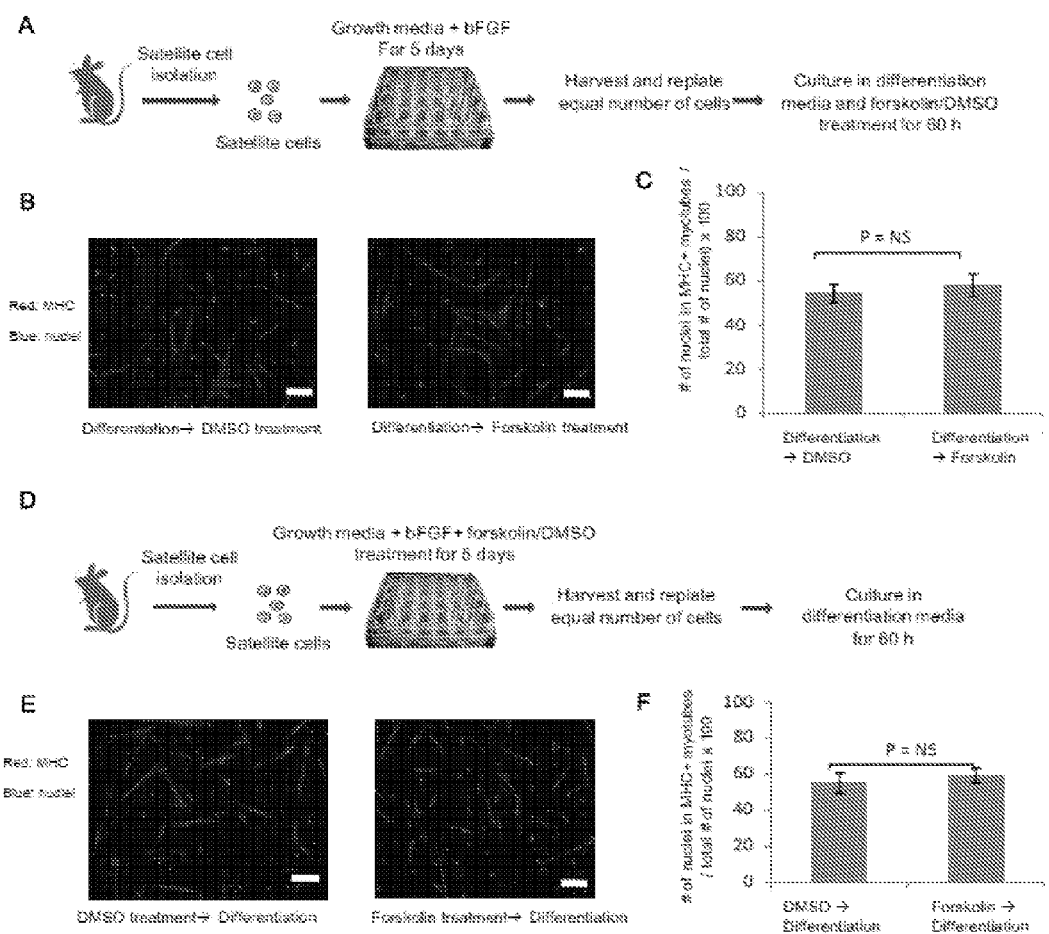
FIGS. 4A-4F show that forskolin-treated satellite cells do not exhibit defective differentiation in vitro, regardless of the timing of compound exposure.

To test if the increase in cell proliferation was caused by an inhibitory effect of forskolin on satellite cell differentiation, we expanded cultured satellite cells under control conditions and then induced them to differentiate in the presence or absence of forskolin. The percentage of nuclei in myotubes in each culture was quantified as an indication of myogenic differentiation (FIG. 4A). Under these conditions, myotube formation from satellite cells was not different between the forskolin and DMSO-treated groups (FIGS. 4B and 4C). Similarly, satellite cells that were exposed to forskolin during growth and then induced to differentiate after removal of the compound (FIG. 4D), formed myotubes with the same efficiency as control treated cells (FIGS. 4E and 4F). Thus, forskolin-treated satellite cells exhibit unperturbed differentiation in vitro, regardless of the timing of compound exposure.

Figure 5:
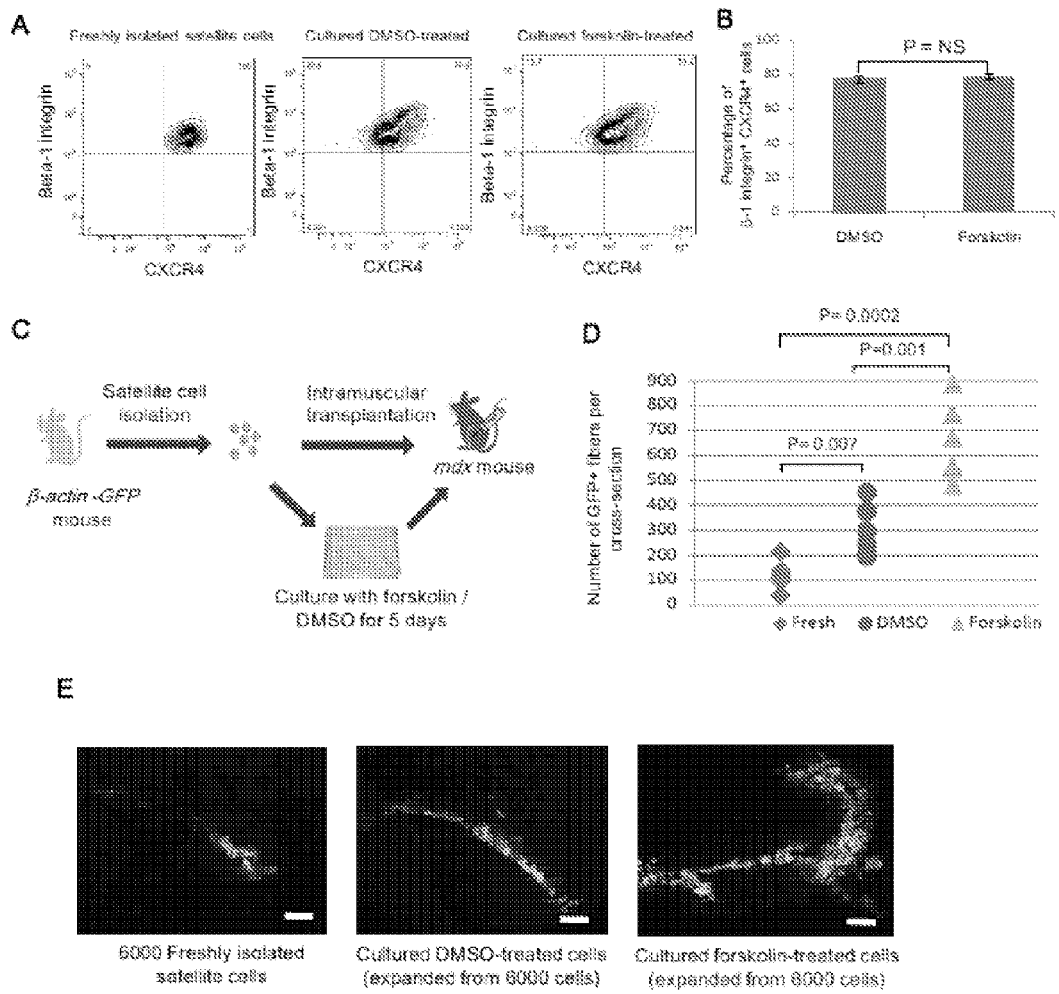
FIGS. 5A-5E shows that forskolin-treated cultured satellite cells retain immunophenotypic characteristics of freshly isolated satellite cells and engraft into skeletal muscle in vivo.

Forskolin-Treated Cells Retain Phenotypic Characteristics of Satellite Cells and Engraft into Dystrophic Skeletal Muscle In Vivo:

Muscle satellite cells are highly enriched within the subset of myofiber associated cells that co-expresses Cxcr4 and β-1 Integrin markers (Sherwood et al., 2004). Myogenic cells lacking CXCR4 and β-1 Integrin fail to engraft into mdx muscle (Cerletti et al., 2008). High levels of Cxcr4 expression also predict high levels of Pax7 expression, which identifies a subset of serially transplantable satellite cells with muscle-stem-cell-like properties (Rocheteau et al., 2012). These data suggest that CXCR4 and β-1 Integrin are useful surrogate markers for engraftable myogenic cells. Flow cytometric analysis revealed that 78.9%+/−1.52% of forskolin-expanded cells maintained co-expression of both CXCR4 and β-1 Integrin after 5 days in culture (FIGS. 5A and 5B). Thus, a high percentage of satellite cells cultured in forskolin retain phenotypic characteristics of freshly isolated engraftable muscle stem cells.

To assess directly the engraftment potential of cultured forskolin-treated satellite cells, we isolated cells from β-actin-GFP transgenic mice (Wright et al., 2001) for transplantation experiments. 6,000 GFP-expressing satellite cells were cultured for 5 days with forskolin, and the resulting cells were transplanted into the pre-injured muscle of mdx mice (FIG. 5C). Recipient muscles were harvested 3-4 weeks after transplantation and analyzed for the presence of donor-engrafted, GFP-expressing myofibers. Consistent with the ability of forskolin to expand a primitive and engraftable myogenic cell population, the number of GFP$^+$ fibers was significantly higher in animals receiving expanded forskolin-treated cells, as compared to those receiving the original number of freshly isolated satellite cells or those receiving expanded DMSO-treated cells (FIGS. 5D and 5E). Furthermore, myofibers engrafted by forskolin-treated cells stained for Dystrophin, which normally is not present in mdx muscle (FIG. 10B). Thus, exposure to forskolin expands engraftable myogenic cells from cultured satellite cells.

A Combination of bFGF, BIO and Forskolin Activates Skeletal Muscle Program in iPSCs:

To examine further the conservation of muscle-inducing potential of chemicals identified in our zebrafish screen, we next evaluated their impact on the differentiation of human pluripotent cells. It is currently difficult to differentiate human iPSCs or ESCs to the skeletal muscle lineage, with the only major success involving ectopic introduction and overexpression of muscle-specific transcription factor genes (Darabi et al., 2012; Tedesco et al., 2012) Strategies to reproducibly drive myogenic differentiation in the absence of genome modification have thus far been elusive.

Figure 6:
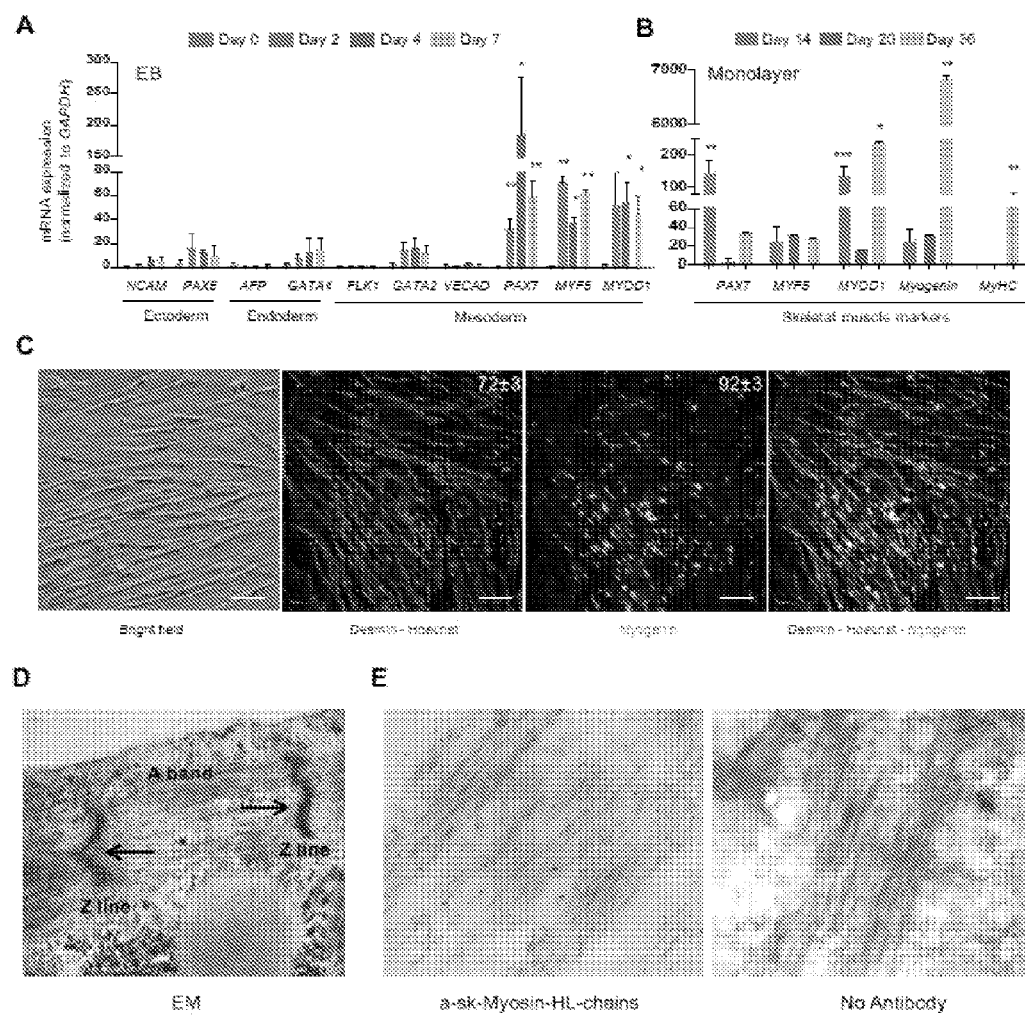
FIGS. 6A-6E shows that treatment of human iPSCs with muscle promoting cocktail induces skeletal muscle differentiation.
Figure 11:
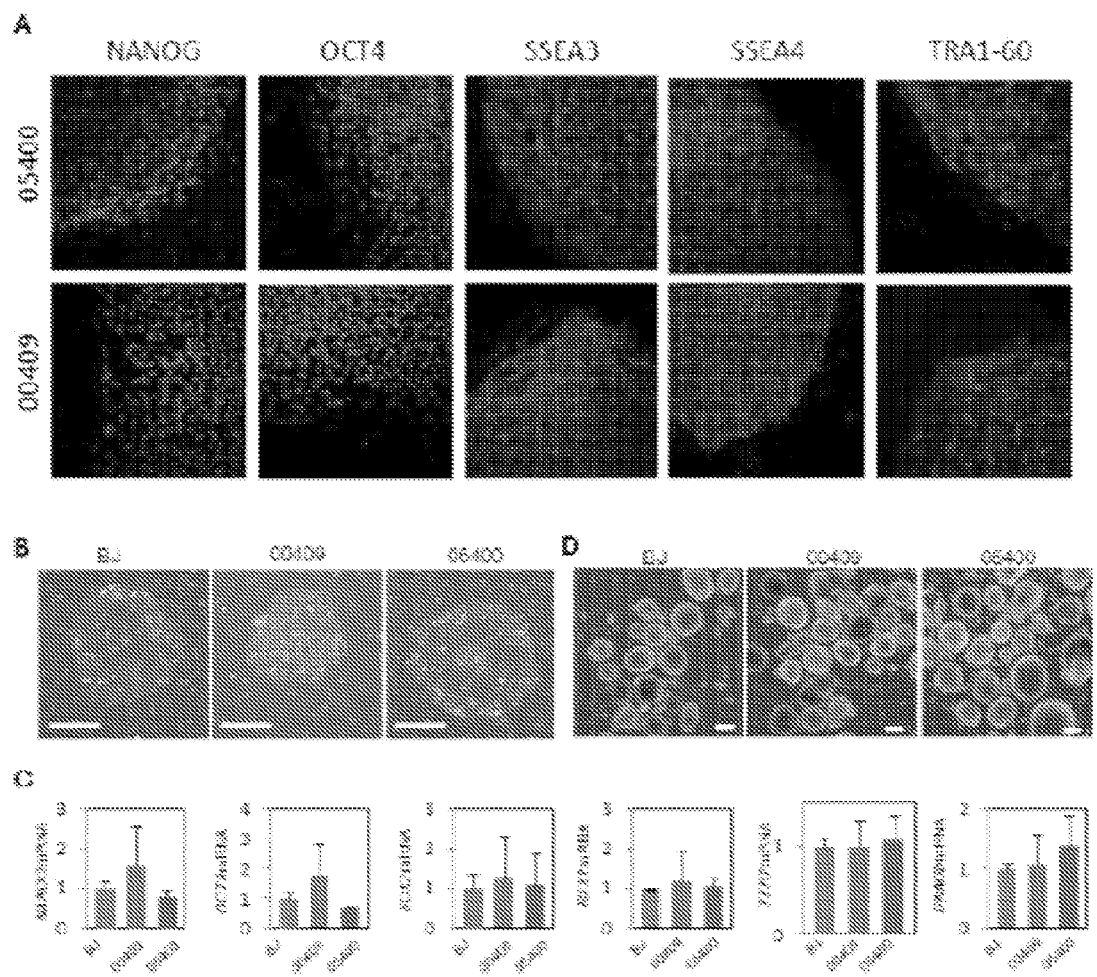
FIGS. 11A-11D show the pluripotency of 00409 and 05400 iPSCs (related to FIG. 6).
Figure 12:
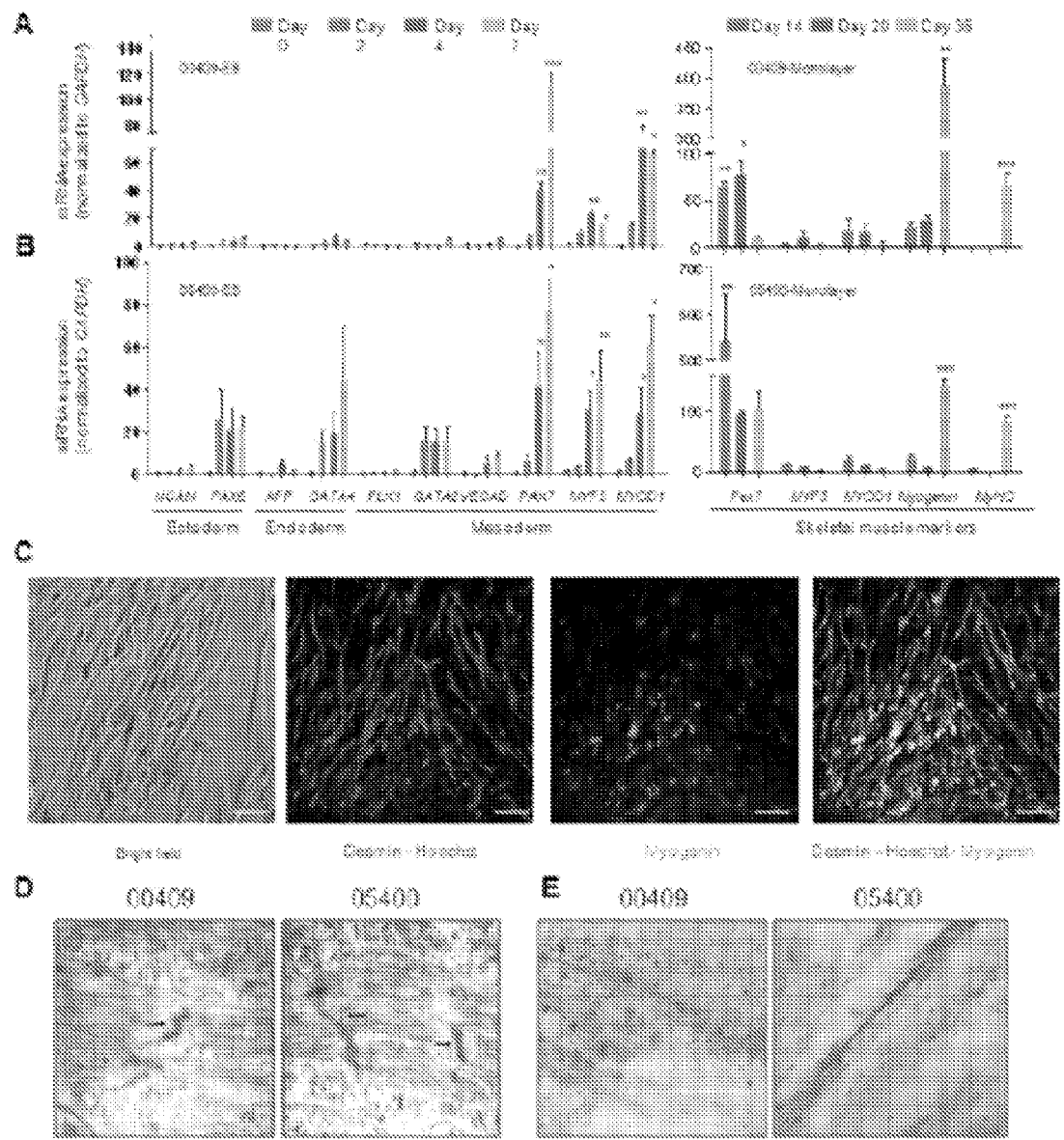
FIGS. 12A-12E show that treatment of 00409 and 05400 iPSCs with muscle promoting medium induces skeletal muscle differentiation (related to FIG. 6).
Figure 13:
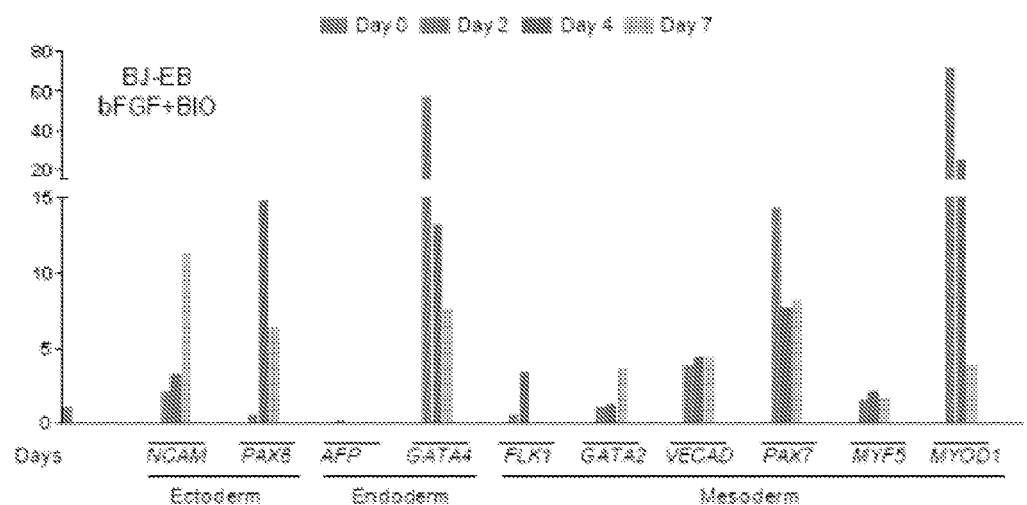
FIGS. 13A and 13B show the effect of combination of bFGF+BIO and bFGF+forskolin on EB differentiation (related to FIG. 6).
Figure 13:
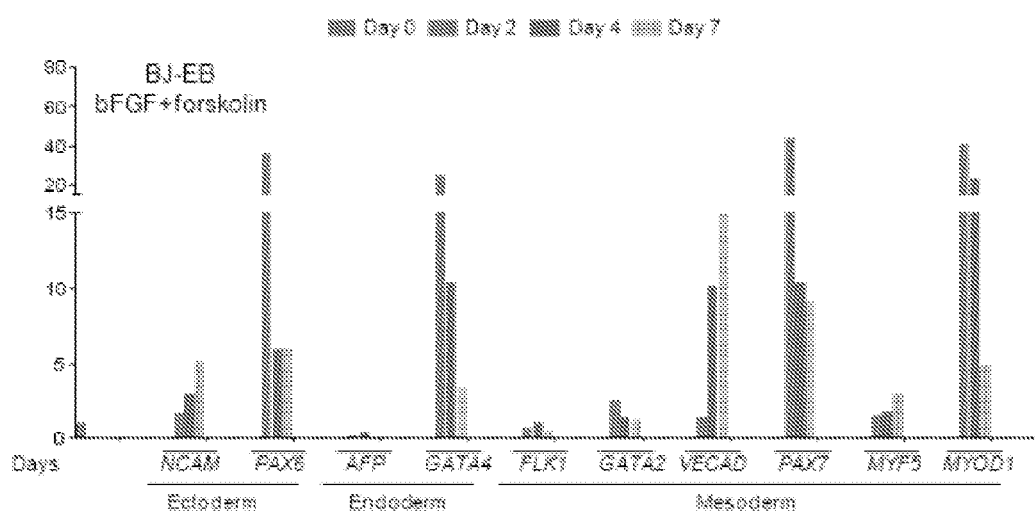

We tested the effects of muscle-promoting compounds on the differentiation of three different lines of iPSCs (00409, 05400, and BJ) derived from healthy human donors (FIGS. 11 and 12). Embryoid bodies (EBs) from BJ, 00409 or 05400 iPSCs were exposed for 7 days to a serum-free differentiation medium containing bFGF (10 ng/ml), BIO (0.5 μM) and forskolin (20 μM) (medium added at day 1, 3 and 5). We used BIO, rather than the GSKβ inhibitors found in the screen, since we tried several GSK3β antagonists and BIO had lower toxicity (data not shown). After 7 days, we measured the expression of a panel of markers specific for ectoderm, endoderm or mesoderm to quantify differentiation outcomes. The mesodermal markers GATA2, PAX7, MYF5, MYOD1 genes were significantly up-regulated after 2, 4 and 7 days of differentiation compared to the corresponding undifferentiated iPSCs lines (FIGS. 6A, 6B, and 13A), while ectodermal and endodermal genes were not significantly altered. These data suggest that this chemical mixture specifically favors the mesodermal lineage and promotes myogenic specification (FIGS. 6A, 6B, and 13A). Two-way combinations, such as bFGF+BIO or bFGF+forskolin, yielded significantly less potent myogenic induction as compared to the bFGF/BIO/forskolin "triple cocktail" (FIGS. 13A and 13B).

To determine whether the iPSC-derived cells undergo terminal skeletal muscle differentiation with bFGF/BIO/forskolin, EBs were plated on matrigel-coated dishes for further differentiation. Gene expression analysis of these cultures revealed that PAX7, MYOD1, and MYF5 expression remained increased after 36 days of culture. Expression of Myogenin and MyHC, two markers of late myogenic differentiation, increased after 20 days, and this increase became more significant after 36 days (FIG. 6B). At day 36, we observed many multinucleated myotubes in our cultures, which were positive for Desmin and Myogenin staining (FIG. 6C). Although iPSCs are known to differentiate spontaneously to cardiac cells, gene expression analysis revealed no increase in cardiac markers (NKX2.5 and GATA2) after 36 days of differentiation and no spontaneously beating cells were found in the treated cultures. In contrast, beating cells were observed in the untreated cells lines after 12-14 days (data not shown). Thus, the three compounds together induced a skeletal myogenic program, rather than a cardiogenic program.

Figure 7:
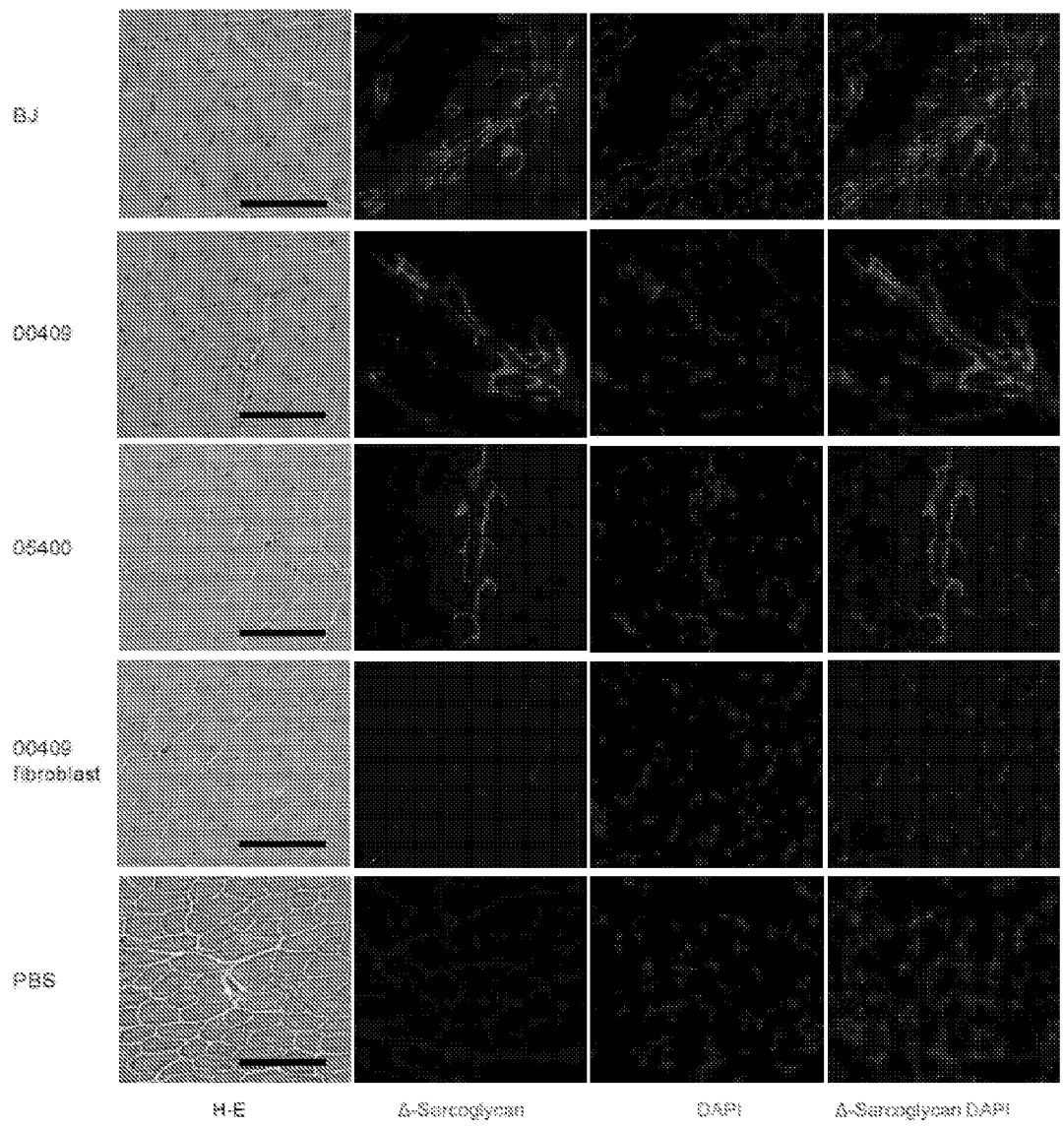
FIG. 7 shows engraftment of human iPSC-derived muscle progenitors into immune-compromised mice. Representative images of immunostaining and Hematoxylin/Eosin on tibialis anterior (TA) sections of injured-NSG mice injected with 1×10⁵ iPSCs at day 12 of differentiation. BJ, 00409, 05400 lines showed positivity for human δ-Sarcoglycan (red) protein indicating engraftment. No staining is observed in PBS injected mice and when a fibroblast line was transplanted. Scale bars represent 100 µM. n=3 per sample.

We further confirmed the skeletal muscle fate of iPSC-derived cells cultured in bFGF/BIO/forskolin by electron microscopy (EM) and immunogold staining with anti-human skeletal muscle Myosin, heavy and light chain antibodies (sk-Myosin-HL-Chains). EM analysis of BJ iPSC-derived cells harvested from culture after 36 days revealed the presence of distinct sarcomere structures, which stained positively for sk-Myosin-HL-Chains (FIGS. 6D and 6E). Similar results were obtained in 00409 and 05400 iPSCs (FIGS. 12C, 12D, and 12E).

iPSCs-Derived Muscle Progenitors can Engraft into Skeletal Muscle In Vivo:

To determine whether myogenic specification using the bFGF/BIO/forskolin cocktail could generate or expand engraftable muscle progenitors from human pluripotent cells, we assessed the ability of myogenic cells derived from human iPSCs to support muscle regeneration in vivo. BJ, 05400 or 00409 iPSCs were differentiated by treatment with bFGF/BIO/forskolin and transplanted into immunodeficient mice after 12 days of differentiation. This time point was chosen because expression of the satellite cell specific transcription factor PAX7 reaches its peak at 12 days (FIG. 6B). iPSC-derived cells were transplanted directly into the limb muscle of NOD/SCID/IL2Rγ −/− (NSG) mice that had been pre-injured by cardiotoxin injection 24 hours before transplantation. The contralateral muscles of these recipient mice were injured but injected with only PBS. One month after transplantation, muscles were harvested and analyzed for engraftment by immunostaining with human muscle specific δ-Sarcoglycan antibody. PBS-injected muscle showed no detectable staining for human δ-Sarcoglycan (FIG. 7). Human δ-Sarcoglycan$^+$ fibers were also absent when the 00409-derived fibroblast cell line was transplanted (FIG. 7). By contrast, transplantation of myogenic progenitors derived from any of the three iPSCs lines (BJ, 05400 or 00409) yielded significant engraftment of cells that showed clear reactivity for human δ-Sarcoglycan (FIG. 7). In addition, no tumor formation was observed in the injected muscles (data not shown). These studies confirm that the iPSC-derived progenitor cells generated by treatment with bFGF/BIO/forskolin maintain myogenic commitment and support regenerative muscle formation after in vivo transplantation.

Discussion

In this study, we took advantage of chemical genetic approaches available in zebrafish to reveal conserved mechanisms controlling the specification and expansion of myogenic progenitor cells. In the process, we defined new approaches to promote the expansion of mouse satellite cells and specify myogenic differentiation of human iPSCs. While many prior studies have employed chemical genetics in whole zebrafish embryos to interrogate development and disease, this approach requires manual manipulation of embryos and often requires time-consuming readout by whole mount in situ hybridization. Some laboratories have screened whole embryos using high-speed pipetting and imaging, but the three-dimensional structure of the embryo makes this approach rather difficult. In comparison to screening using whole zebrafish embryos, the culture-based screening system described here takes one sixth the time and uses one tenth of the embryos. Such throughput enables screening of significantly larger chemical libraries and increasing the speed of conventional chemical screening on mammalian cell lines. Transgenic zebrafish with a fluorescent reporter known to label a particular cell type in vivo can be used and images can be automatically captured and stored by imaging cytometers such that the cells do not need to be fixed or scored immediately. Recently, a zebrafish explant system with some similarities to our embryo culture system identified compounds that could expand angiogenic progenitors (Huang et al., 2012). Our system enables the combination of reporters of different colors to simultaneously interrogate multiple different developmental states or lineages.

One remarkable aspect of this screening system is that it appears to support critical developmental transitions in the absence of the normal spatial and temporal information available in the embryo. While some cell lineages may be difficult to derive from zebrafish blastomere cells, disassociating embryos at later stages could be used to study the desired tissue. Ultimately, we predict that similar zebrafish cultures systems will prove highly useful in screens for compounds and pathways affecting development in many different organ systems.

Another noteworthy attribute of the zebrafish embryo culture system is its ability to identify critical pathways that influence tissue specification and progenitor cell expansion in analogous systems across species. The chemicals found in the zebrafish system expand postnatal muscle satellite cells from mice and specify myogenic differentiation from human pluripotent cells. These chemicals identified in our screen proved useful in addressing two of the more vexing challenges in the production of mammalian muscle precursors for experimental applications and, perhaps ultimately, for cell therapy. Indeed, one of the major obstacles in using purified skeletal muscle satellite cells for cell therapy is their very low frequency in adult tissue. High numbers of engraftable cells are required for functional recovery of skeletal muscles throughout the body in genetic muscle disorders, and efforts to expand purified satellite cells in culture while maintaining their engraftment potential have been largely unsuccessful (Montarras et al., 2005). Here, we show that mouse muscle progenitors treated with the adenylyl cyclase activator forskolin have enhanced proliferation in culture. These data are consistent with a previous report showing that activation of cAMP signaling in transgenic mice expressing an activated from of cAMP response element binding protein (CREB) increases the in vitro proliferation of primary myoblasts (Stewart et al., 2011). Forskolin does not inhibit satellite cell differentiation in vitro, and forskolin-treated muscle progenitor cells differentiate normally after removal of the compound. Forskolin-treated progenitor cells also retain most phenotypic characteristics of freshly isolated satellite cells. It is possible that forskolin mimics activation of a natural G-protein coupled receptor in the genesis or maintenance of muscle progenitors. When transplanted into pre-injured mdx muscle, forskolin-expanded satellite cells engrafted to generate Dystrophin-expressing myofibers. Forskolin treatment dramatically increased the proliferation of muscle progenitors isolated from dystrophic mdx mice, which exhibited defective ex vivo expansion under control conditions. Thus, forskolin treatment may be useful to enhance the ex vivo expansion of human dystrophic satellite cells for autologous therapy or to improve the efficiency of cell replacement therapies for muscle disorders.

The capacity of forskolin to expand functional satellite cells may also explain the enhanced myogenesis observed in zebrafish blastomeres and human iPSCs upon forskolin exposure. During culture, some pluripotent cells likely differentiate to form skeletal muscle progenitors and forskolin may act to increase the proliferation of these myogenic cells by activating cAMP signaling, thereby enriching the muscle-forming capacity in the culture. Given prior difficulties in obtaining robust skeletal muscle differentiation from pluripotent cells, most previous studies have relied on transgenic modification (Darabi et al., 2012; Tedesco et al., 2012). By applying insights obtained from our zebrafish embryo culture screen, we identified a novel chemical cocktail that successfully enabled myogenic differentiation of iPSCs into mature myofibers in vitro and in vivo in the absence of genomic modification or transcription factor overexpression. A screen to find such chemical inducers of muscle development using iPSCs would have been highly reagent- and labor-intensive, particularly as myogenic differentiation in the human system requires ~36 days. In contrast, the zebrafish muscle differentiation protocol takes only 1-2 days, enabling the completion of a small-scale screen in about one week.

One remarkable aspect of the myogenic protocol defined here is the selectivity with which the skeletal muscle fate is specified during culture. Simultaneous inhibition of GSK3β and activation of cAMP and bFGF pathways during EB formation is sufficient to specifically promote commitment of these cells to skeletal muscle differentiation, and our marker analysis indicates that alternative fates, including cardiac and neural lineages, are relatively rare in cultures exposed to the triple cocktail. Interestingly, prior studies indicate that cAMP signaling is increased at discrete times during embryonic muscle differentiation and promotes muscle regeneration and metabolic adaptation in satellite cells (Carlsen, 1975; Chen et al., 2005; Le Peuch et al., 1979; Zalin and Montague, 1974). Myogenesis of muscle stem cells can also be induced by Wnt activation (Brack et al., 2008; Polesskaya et al., 2003), and bFGF-mediated activation of PI3K-AKT pathway has likewise been reported as a potent mediator of muscle differentiation (Stitt et al., 2004). The data presented herein unexpectedly shows that pathways can cooperate uniquely during muscle differentiation, enabling ex vivo myogenic differentiation, and generation of engraftable myogenic progenitors, which mix with host muscle upon transplantation into damaged tissue and are indistinguishable by hematoxylin and eosin staining from the regenerated mouse muscle fibers. These results, together with the absence of teratoma formation and the ability to achieve myogenic specification of iPSCs by giving solely exogenous factors, shows that iPSC-derived myogenic cells can be applied to regenerative cell therapy for the treatment of musculoskeletal diseases. In any event, the findings reported are highly beneficial to understanding normal myogenesis and for in vitro studies of musculoskeletal and metabolic disease in a variety of experimental settings.

REFERENCES

1. Barberi, T., Bradbury, M., Dincer, Z., Panagiotakos, G., Socci, N. D., and Studer, L. (2007). Derivation of engraftable skeletal myoblasts from human embryonic stem cells. Nature Medicine 13, 642-648.
2. Brack, A. S., Conboy, I. M., Conboy, M. J., Shen, J., and Rando, T. A. (2008). A temporal switch from notch to Wnt signaling in muscle stem cells is necessary for normal adult myogenesis. Cell Stem Cell 2, 50-59.
3. Carlsen, R. C. (1975). The possible role of cyclic AMP in the neurotrophic control of skeletal muscle. J Physiol 247, 343-361.
4. Cerletti, M., Jang, Y. C., Finley, L. W., Haigis, M. C., and Wagers, A. J. (2012). Short-term calorie restriction enhances skeletal muscle stem cell function. Cell Stem Cell 10, 515-519.

5. Cerletti, M., Jurga, S., Witczak, C. A., Hirshman, M. F., Shadrach, J. L., Goodyear, L. J., and Wagers, A. J. (2008). Highly efficient, functional engraftment of skeletal muscle stem cells in dystrophic muscles. Cell 134, 37-47.

6. Chen, A. E., Ginty, D. D., and Fan, C. M. (2005). Protein kinase A signalling via CREB controls myogenesis induced by Wnt proteins. Nature 433, 317-322.

7. Cuenda, A., and Cohen, P. (1999). Stress-activated protein kinase-2/p38 and a rapamycin-sensitive pathway are required for C2C12 myogenesis. J Biol Chem 274, 4341-4346.

8. Darabi, R., Arpke, R. W., Irion, S., Dimos, J. T., Grskovic, M., Kyba, M., and Perlingeiro, R. C. (2012). Human ES- and iPS-derived myogenic progenitors restore DYSTROPHIN and improve contractility upon transplantation in dystrophic mice. Cell Stem Cell 10, 610-619.

9. Darabi, R., Gehlbach, K., Bachoo, R. M., Kamath, S., Osawa, M., Kamm, K. E., Kyba, M., and Perlingeiro, R. C. (2008). Functional skeletal muscle regeneration from differentiating embryonic stem cells. Nature Medicine 14, 134-143.

10. de Jong, J. L., Davidson, A. J., Wang, Y., Palis, J., Opara, P., Pugach, E., Daley, G. Q., and Zon, L. I. (2010). Interaction of retinoic acid and scl controls primitive blood development. Blood 116, 201-209.

11. Draper, B. W., Stock, D. W., and Kimmel, C. B. (2003). Zebrafish fgf24 functions with fgf8 to promote posterior mesodermal development. Development 130, 4639-4654.

12. Fan, L., and Collodi, P. (2006). Zebrafish embryonic stem cells. Methods Enzymol 418, 64-77.

13. Fisher, M. E., Isaacs, H. V., and Pownall, M. E. (2002). eFGF is required for activation of XmyoD expression in the myogenic cell lineage of Xenopus laevis. Development 129, 1307-1301.

14. Gros, J., Manceau, M., Thome, V., and Marcelle, C. (2006). A common somitic origin for embryonic muscle progenitors and satellite cells. Nature 435, 954-958.

15. Groves, J. A., Hammond, C. L., and Hughes, S. M. (2005). Fgf8 drives myogenic progression of a novel lateral fast muscle fibre population in zebrafish. Development 132, 4211-4222.

16. Hinits, Y., Osborn, D. P., and Hughes, S. M. (2009). ifferential requirements for myogenic regulatory factors distinguish medial and lateral somitic, cranial and fin muscle fibre populations. Development 136, 403-414.

17. Huang, H., Lindgren, A., Wu, X., Liu, N. A., and Lin, S. (2012). High-throughput screening for bioactive molecules using primary cell culture of transgenic zebrafish embryos. Cell Reports 2, 695-704.

18. Ju, B., Chong, S. W., He J, Wang X, Xu Y, Wan H, Tong Y, Yan T, Korzh V, and Z., G. (2003). Recapitulation of fast skeletal muscle development in zebrafish by transgenic expression of GFP under the mylz2 promoter. Dev Dyn 227, 14-26.

19. Le Peuch, C. J., Ferraz, C., Walsh, M. P., Demaille, J. G., and Fischer, E. H. (1979). Le Peuch C J, Ferraz C, Walsh M P, Demaille J G, Fischer E H. Calcium and cyclic nucleotide dependent regulatory mechanisms during development of chick embryo skeletal muscle. Biochemistry 18.

20. Lu, J., Tan, L., and Li P, G. H., Fang B, Ye S, Geng Z, Zheng P, Song H. (2009). All-trans retinoic acid promotes neural lineage entry by pluripotent embryonic stem cells via multiple pathways. BMC Cell Biol 10, 57.

21. Mauro, A. (1961). Satellite cell of skeletal muscle fibers. J Biophys Biochem Cytol 9, 493-495.

22. Metzger, H., and Lindner, E. (1981). The positive inotropic-acting forskolin, a potent adenylate cyclase activator. Arzneimittelforschung 31, 1248-1250.

23. Mizuno, Y., Chang, H., Umeda, K., Niwa, A., Iwasa, T., Awaya, T., Fukada, S., Yamamoto, H., Yamanaka, S., Nakahata, T., et al. (2010). Generation of skeletal muscle stem/progenitor cells from murine induced pluripotent stem cells. FASEB J 24, 2245-2253.

24. Montarras, D., Morgan, J., Collins, C., Relaix, F., Zaffran, S., Cumano, A., Partridge, T., and Buckingham, M. (2005). Direct isolation of satellite cells for skeletal muscle regeneration. Science 309, 2064-2067.

25. Polesskaya, A., Seale, P., and Rudnicki, M. A. (2003). Wnt signaling induces the myogenic specification of resident CD45+ adult stem cells during muscle regeneration. Cell 113, 841-852.

26. Rocheteau, P., Gayraud-Morel, B., Siegl-Cachedenier, I., Blasco, M. A., and Tajbakhsh, S. (2012). A subpopulation of adult skeletal muscle stem cells retains all template DNA strands after cell division. Cell 148, 112-125.

27. Schnapp, E., Pistocchi, A. S., Karampetsou, E., Foglia, E., Lamia, C. L., Cotelli, F., and Cossu, G. (2009). Induced early expression of mrf4 but not myog rescues myogenesis in the myod/myf5 double-morphant zebrafish embryo. J Cell Sci 2009 Feb. 15; 122(Pt 4):481-8 122, 481-488.

28. Seale, P., Sabourin, L. A., Girgis-Gabardo, A., Mansouri, A., Gruss, P., and Rudnicki, M. A. (2000). Pax7 is required for the specification of myogenic satellite cells. Cell 102, 777-786.

29. Seamon, K. B., Padgett, W., and Daly, J. W. (1981). Forskolin: unique diterpene activator of adenylate cyclase in membranes and in intact cells. Proceedings of the National Academy of Sciences of the United States of America 78, 3363-3367.

30. Sherwood, R. I., Christensen, J. L., Conboy, I. M., Conboy M J, Rando T A, Weissman I L, and A J., W. (2004). Isolation of adult mouse myogenic progenitors: functional heterogeneity of cells within and engrafting skeletal muscle. Cell 119, 543-554.

31. Sicinski, P., Geng, Y., Ryder-Cook, A. S., Barnard, E. A., Darlison, M. G., and Barnard, P. J. (1989). The molecular basis of muscular dystrophy in the mdx mouse: a point mutation. Science 244, 1578-1580.

32. Stewart, R., Flechner, L., Montminy, M., and Berdeaux, R. (2011). CREB is activated by muscle injury and promotes muscle regeneration. PLoS One 6, e24714.

33. Stitt, T. N., Drujan, D., Clarke, B. A., Panaro, F., Timofeyva, Y., Kline, W. O., Gonzalez, M., Yancopoulos, G. D., and Glass, D. J. (2004). The IGF-1/PI3K/Akt pathway prevents expression of muscle atrophy-induced ubiquitin ligases by inhibiting FOXO transcription factors. Mol Cell 14, 395-403.

34. Tedesco, F. S., Gerli, M. F., Perani, L., Benedetti, S., Ungaro, F., Cassano, M., Antonini, S., Tagliafico, E., Artusi, V., Longa, E., et al. (2012). Transplantation of genetically corrected human iPSC-derived progenitors in mice with limb-girdle muscular dystrophy. Sci Transl Med 4, 140.

35. Thisse, B., Pflumio, S., Fürthauer, M., Loppin, B., Heyer, V., Degrave, A., Woehl, R., Lux, A., Steffan, T., Charbonnier, X. Q., et al. (2001). Expression of the zebrafish genome during embryogenesis (NIH RO1 RR15402). ZFIN Direct Data Submission (http://zfin org).

36. Weinberg, E. S., Allende, M. L., Kelly, C. S., Abdelhamid, A., Murakami, T., Andermann, P., Doerre, O. G., Grunwald, D. J., and Riggleman, B. (1996). Developmental regulation of zebrafish MyoD in wild-type, no tail and spadetail embryos. Development 122, 271-280.
37. Wright, D. E., Cheshier, S. H., Wagers, A. J., Randall, T. D., Christensen, J. L., and Weissman, I. L. (2001). Cyclophosphamide/granulocyte colony-stimulating factor causes selective mobilization of bone marrow hematopoietic stem cells into the blood after M phase of the cell cycle. Blood 97, 2278-2285.
38. Wu, Z., Woodring, P. J., Bhakta, K. S., Tamura, K., Wen, F., Feramisco, J. R., Karin, M., Wang, J. Y., and Puri, P. L. (2000). p38 and extracellular signal-regulated kinases regulate the myogenic program at multiple steps. Mol Cell Biol 20, 3951-3964.
39. Zalin, R. J., and Montague, W. (1974). Changes in cyclic AMP, adenylate cyclase and protein kinase levels during the development of embryonic chick skeletal muscle. Cell 2, 103-108.
40. Zetser, A., Gredinger, E., and Bengal, E. (1999). p38 mitogen-activated protein kinase pathway promotes skeletal muscle differentiation. Participation of the Mef2c transcription factor. J Biol Chem 274, 5193-5200.
41. Zheng, J. K., Wang, Y., Karandikar, A., Wang, Q., Gai, H., Liu, A. L., Peng, C., and Sheng, H. Z. (2006). Skeletal myogenesis by human embryonic stem cells. Cell Research 16, 713-722.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A method of producing a skeletal myogenic cell, the method comprising culturing a pluripotent stem cell with at least two of: (i) a GSK3 pathway inhibitor; (ii) a compound that increases intracellular levels of 3',5'-cyclic adenosine monophosphate (cAMP); and (iii) a FGF pathway activator, and wherein the GSK3 pathway inhibitor is a GSK3β inhibitor, the compound that increases intracellular levels of cAMP is an adenylyl cyclase activator and is forskolin, and the FGF pathway activator is a phosphatidylinositide 3-kinase (PI3K) and mTOR activator and is bFGF, thereby producing a skeletal myogenic cell.

2. The method of claim 1, wherein the pluripotent stem cell is an induced pluripotent stem (iPS) cell.

3. The method of claim 1, wherein the GSK3β inhibitor is BIO, the adenylyl cyclase activator is forskolin, and the PI3K/mTOR activator is bFGF.

* * * * *

UNITED STATES PATENT AND TRADEMARK OFFICE
CERTIFICATE OF CORRECTION

| | |
|---|---|
| PATENT NO. | : 9,771,560 B2 |
| APPLICATION NO. | : 14/384514 |
| DATED | : September 26, 2017 |
| INVENTOR(S) | : Leonard I. Zon et al. |

It is certified that error appears in the above-identified patent and that said Letters Patent is hereby corrected as shown below:

In the Specification

At Column 1, Lines 19-23:
"This invention was made with government support under grant nos. 5P30 DK49216-19, 5R01CA103846-10, DP2OD004345 and DK31036 awarded by the National Institutes of Health. The government has certain rights in the invention."

Should be replaced with:
--This invention was made with government support under Grant Nos. DK049216, DK031036, OD004345, and CA103846, awarded by the National Institutes of Health. The Government has certain rights in the invention.--

Signed and Sealed this
Twenty-second Day of August, 2023

Katherine Kelly Vidal
*Director of the United States Patent and Trademark Office*

SEQUENCE LISTING

```
<160> NUMBER OF SEQ ID NOS: 44

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atggaaactc tattaaagtg aacctg                                          26

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tagacctcat actcagcatt ccagt                                           25

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tctaatcgaa gggccaaatg                                                 20

<210> SEQ ID NO 4
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 4
tgtgagggct gtgtctgttc                                           20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agcttggtgg tggatgaaac                                           20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccctcttcag caaagcagac                                           20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctagaccgtg ggttttgcat                                           20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgggttaagt gcccctgtag                                           20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agtgatcgga aatgacactg ga                                        22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
gcacaaagtg acacgttgag at                                            22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcaaccccta ctatgccaac c                                             21

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cagtggcgtc ttggagaag                                                19

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cagcccaaag tgtgtgagaa                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgtgatgttg gccgtgttat                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tggtatcgtg gaaggactca                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttcagctcag ggatgacctt                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgtgctcaga atcaagttcg                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtcaggttcc gactccacat                                               20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcctgaagaa ggtcaaccag                                               20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccatcagagc agttggaggt                                               20

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgccacaacg gacgactt                                                 18

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 22
cgggtccagg cttcgaa                                                    17

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agatgtgtct gtggccttcc                                                 20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agctggcttc ctagcatcag                                                 20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ttcattgggg tcttggacat                                                 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aacgtccact caatgccttc                                                 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ataagtcgaa ggtgcgtcgt                                                 20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
```
ggcaacatct gaagccattt                                          20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgtgcaccaa catctacaag                                          20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gcgttcttgg ctttcaggat                                          20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tccaacatcc tgaacctcag                                          20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gactggatgt tctgggtctg                                          20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gtggaggaag ctgacaacaa                                          20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
caggttttct ttccctagct                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tggacacgtc tgtgctcttc                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gtcttggcgt cttctcgaac                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ttgtcggaga cggagaagcg                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ttgtcggaga cggagaagcg                                              20

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Phe Met Arg Phe
1

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Phe Gln Phe Met Arg Phe
1               5

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Tyr Met Arg Phe
1

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Leu Pro Leu Arg Phe
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Tyr Phe Met Arg Phe
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Pro Leu Arg Phe
1               5
```